United States Patent [19]

Dresdner, Jr. et al.

[11] Patent Number: 5,357,636
[45] Date of Patent: Oct. 25, 1994

[54] FLEXIBLE PROTECTIVE MEDICAL GLOVES AND METHODS FOR THEIR USE

[76] Inventors: Karl P. Dresdner, Jr., 235 W. 48th St., Apt. #18N, New York City, N.Y. 10036; Kenneth H. Dangman, 400 Riverside Dr., Apt. #1A, New York City, N.Y. 10032; Edward A. Jazlowiecki, 15 Sachems Trail, West Simsbury, Conn. 06092

[21] Appl. No.: 906,829

[22] Filed: Jun. 30, 1992

[51] Int. Cl.$^5$ .................. A41D 13/10; A41D 19/00
[52] U.S. Cl. ............................ 2/161.7; 2/167; 2/168; 2/169
[58] Field of Search ............... 2/161 R, 168, 167, 169, 2/164, 159, 161.6, 161.7, 161.8, 16, 21; 128/292, 306, 307, 842, 844; 604/349; 427/2

[56] References Cited

U.S. PATENT DOCUMENTS

| | | |
|---|---|---|
| 2,541,103 | 2/1951 | Sander . |
| 3,633,216 | 1/1972 | Shonholtz .................... 2/168 |
| 4,526,828 | 7/1985 | Fogt et al. . |
| 4,771,482 | 9/1988 | Shlenker .................... 2/161 R |
| 4,901,372 | 2/1990 | Pierce ........................ 2/167 |
| 4,919,966 | 4/1990 | Shlenker .................... 2/159 X |
| 4,935,260 | 6/1990 | Shlenker .................... 2/159 X |
| 5,003,628 | 4/1991 | Miyake et al. . |
| 5,019,604 | 5/1991 | Lemole . |
| 5,024,852 | 6/1991 | Busnel et al. ............... 2/161 R X |
| 5,031,245 | 7/1991 | Milner . |
| 5,045,341 | 9/1991 | Shlenker .................... 2/167 X |
| 5,128,168 | 7/1992 | Shlenker et al. ............ 2/167 X |
| 5,130,159 | 7/1992 | Shlenker et al. ............ 2/167 X |

FOREIGN PATENT DOCUMENTS

| | | |
|---|---|---|
| WO91/10409 | 7/1991 | PCT Int'l Appl. . |
| 9014048 | 11/1990 | World Int. Prop. O. ........... 2/21 |

OTHER PUBLICATIONS

Stecher, et al., "Nonoxynol", 1968 8th ed., The Merck Index, p. 745.
Maki, "Lister Revisted: Surgical Antisepsis and Asepsis", 1976, New England Journal of Medicine, 294(3): pp. 1286-1287.
Viljanto, "Disinfection of Surgical Wounds Without Inhibition of Normal Wound Healing", 1980, Arch., Surg., 115, pp. 253-256.
Rodeheaver, et al., "Bactericidal Activity and Toxicity of Iodine-Containing Solutions in Wounds", 1982, Arch. Surg., 117, pp. 181-186.

(List continued on next page.)

*Primary Examiner*—Clifford D. Crowder
*Assistant Examiner*—Amy B. Vanatta

[57] ABSTRACT

A flexible protective medical glove containing a non-liquid antiseptic composition and methods for its use are disclosed. The glove comprises a thin inner layer and a thin outer layer of material; preferably the outer layer is a more elastic and less plastic layer than the inner layer. A compartment between the layers of the glove is capable of providing a non-liquid antiseptic composition which comprises an antiseptic in a non-liquid composition. The non-liquid antiseptic composition may also contain a surface-active agent, an algesic agent, a colorant, a vasoconstrictive agent, an odorant, or a viscosity-modifying agent. An object puncturing the glove wall can become coated with the non-liquid antiseptic composition and can automatically transfer some of the antiseptic composition from the glove onto the hand and into a hand wound should the object cause a wound; useful as an immediate preventative antiseptic treatment to help to decontaminate the hand and hand wound of infectious pathogens that may have been transferred there by the object. The treatment can help to protect a gloved individual such as a surgeon, a medical doctor, a health care worker, a law enforcement officer, a dentist or any worker whose work may place them at some risk of becoming contaminated through the hands by an infectious pathogen including the AIDS virus or hepatitis B virus.

20 Claims, 7 Drawing Sheets

OTHER PUBLICATIONS

Simmons, et al., "CDC Guidelines for the Prevention and Control of Nosocomial Infections" (Guideline for hospital environmental control), Am. Journal of Infection Control, 1983, 11[3], pp. 91–120.

Simmons, et al., "CDC Guidelines for the Prevention and Control of Nosocomial Infections" (Guideline for prevention of surgical wound infections), Am. Journal of Infection Control, 1983, 11[4], pp. 133–143.

Hicks, et al., "Inactivation of HTLV-III/Lav-Infected Cultures or Normal Human Lymphocytes By Nonoxynol-9 in Vitro", 1985, Dec. 21/28, The Lancet, pp. 1422–1423.

Harvey, "Antiseptics and Disinfectants; Fungicides; Ectoparasiticides", 1985, In: The Pharmacological Basis of Therapeutics; 7th ed., Chapter 41, pp. 959–979.

Weiss, et al., "HTLV-III Infection Among Health Care Workers", 1985; The Journal of the Am. Med. Assoc., vol. 254, No. 15; pp. 2089–2093.

Rietmeijer et al., "Condoms as Physical and Chemical Barriers Against Human Immunodeficiency Virus," 1988, The Journal of the Am. Med. Assoc., 295[12], pp. 1851–1853.

Newsom, et al., "What is in the Surgeon's Glove?", 1988, Journal of Hospital Infection, 11[supplement A], pp. 244–259.

Bartlett, "Testing for HIV Infection: Recommendations for Surgeons", 1988, Am. College of Surgeons Bulletin, 73[3], pp. 4–10.

Gerberding, et al., "Risk of Exposure of Surgical Personnel to Patients' Blood During Surgery at San Francisco General Hospital", 1990, The New England Journal of Medicine, 322[25] pp. 1788–1793.

Monteflori, et al., "Effective Inactivation of Human Immunodeficiency Virus With Chlorhexidine Antiseptics Containing Detergents and Alcohol", 1990, Journal of Hospital Infection, 15, pp. 279–282.

Speller, et al., "Acquired Immune Deficiency Syndrome: Recommendations of a Working Party of the Hospital Infection Society", 1990, Journal of Hospital Infection, 15 pp. 7–34.

Sanders, et al., "Outer Gloves in Orthopaedic Procedure", 1990, The Journal of Bone and Joint Surgery, Inc., 72-A[6], pp. 914–917.

Closs & Tierney, "Theatre Gowns: A Survey of the Extent of User Protection", 1990, Journal of Hospital Infection, 15, pp. 375–378.

Mandlebort, et al., "A Survey of Exposure, Practices and Recommendations of Surgeons in the Care of Patients with Human Immunodeficiency Virus", 1990, Surgery—Gynecology & Obstetrics, vol. 171, No. 2, pp. 99–106.

Henderson, et al., "Risk of Occupational Transmission of Human Immunodeficiency Virus Type 1 (HIV-1) Associated with Clinical Exposures", 1990, Annals of Internal Medicine, vol. 113, pp. 740–746.

Beekmann, et al., "Risky Business: Using Necessarily Imprecise Casualty Counts to Estimate Occupational Risks for HIV-1 Infection", 1990, Infection Control Hospital Epidemiology, 11[7], pp. 371–379.

Bloomfield, et al., "Evaluation of Hypochlorite-Releasing Disinfectants Against the Human Immunodeficiency Virus (HIV)", 1990, Journal of Hospital Infection, 15, pp. 273–278.

Johnson, et al., "Efficacy of Glove Combinations in Reducing Cell Culture Infection After Glove Puncture With Needles Contaminated With Human Immunodeficiency Virus Type 1", 1991, Infection Control and Hospital Epidemiology, 12[7], pp. 435–438.

Panlilio, et al., "Blood Contacts During Surgical Procedures", 1991, Journal of American Medical Association, 265[12], pp. 1533–1537.

Gross, "Many Doctors Infected with AIDS Don't Follow New U.S. Guidelines", 1991, The New York Times, vol. CXL . . . No. 48, 696, p. 1.

Orentlicher, "HIV-Infected Surgeons: Behringer v. Medical Center", 1991, The Journal of American Medical Associations, 266[8], pp. 1134–1137.

Zanowiak, "Skin Infections: The Role of OTC Therapy", Jun. 1991, U.S. Pharmacist pp. 40–47.

Mast, "Factors Predicting Infectivity Following Needlestick Exposure to HIV: A Invitro Model", 1991, Clinical Research, 39(1): p. 58A.

Wright, "Mechanisms of Glove Tears and Sharp Injuries Among Surgical Personnel," 1991, Journal of American Medcical Association, 266(12): 1668–1671.

Boscia, Peterson, Szpalski, Panlilio & Gerberding, Letters to the Editor: "Surgery, AIDS, and Hepatitus B", 1991, Journal of American Medical Association, 266(10: 1360–1362.

Belkin, L. "Fear of Disease Changing How Doctors Work", Apr. 7, 1992, A1, B2, New York Times.

Assoc. Press, "Teen-Agers and AIDS: The Risk Worsens", Apr. 14, 1992, C3, New York Times–Medical Science Section.

Remington's Pharmaceutical Sciences: 1965, "Suspensions", pp. 455–459; Medicated Applications pp. 525–556; Antimicrobial Drugs, pp. 1228–1252.

Remington's Pharmaceutical Sciences: 1990, "Antimicrobial Drugs", pp. 1163–1241.

FLEXIBLE PROTECTIVE MEDICAL GLOVES AND METHODS FOR THEIR USE

FIELD OF THE INVENTION

The present invention is a flexible protective medical glove that relates to the thin-walled medical glove that doctors, health care workers and other workers can wear on one or both hands as a physical barrier form of protection. In particular the present invention is a glove containing an antiseptic composition other than a liquid antiseptic composition within the glove wall;:the non-liquid antiseptic composition comprises an antiseptic in a non-liquid composition; for example, the composition may comprise a powder, a paste, a foam, a gel, a coating, a solid layer, a semi-solid foam, a putty or a state of matter that lacks the ability to flow like a liquid.

No useful medical glove is puncture-proof; when an individual wears a conventional medical glove, the thin glove wall can readily become punctured by an object and the hand underneath the glove may become wounded. If the object is contaminated with an infectious pathogen, then the hand and the hand wound may become contaminated and the individual may suffer a systemic pathogenic infection. A glove in accordance with the present invention can be used to help to prevent the hand and the hand wound from a contamination that might cause a systemic infection; the invention is urgently needed for example for use in medical work environments that may harbor the AIDS virus, the hepatitis B virus, or other infectious pathogens. When an object punctures a glove in accordance with the present invention, the object can contact and can then become coated with some of the antiseptic composition. If the object also causes a wound to the hand, then some of the antiseptic composition coating the object may be transferred to the hand and deposited into the hand wound, thereby helping to provide an immediate and automatic antiseptic treatment of the contaminated hand and hand wound. In general, the non-liquid antiseptic composition used in the present invention, lacking the ability to flow like a liquid can not leak from a glove wall puncture. For some embodiments of the present invention, manual massage of the gloved hand may be used as a means for causing extrusion of the non-liquid antiseptic composition from the glove wall puncture to increase the dispersion of the non-liquid antiseptic composition onto the hand and into hand wound as an additional treatment.

BACKGROUND OF THE INVENTION

In general, latex gloves are worn during a medical procedure to provide a physical barrier between the patient's body or tissues and the hands, wrist and arm regions of a health care practitioner such as a physician, nurse, phlebotomist and the like. The gloves must be flexible so that the manual dexterity of the health care practitioner or worker is not significantly decreased. The gloves are usually well-fitting and comfortable so that glove wear does not cause hand fatigue or discomfort.

Disposible sterile and nonsterile latex medical gloves are available. Sterile latex medical gloves are also known in the field as surgical gloves; they are sterilized at the glove factory; are made available typically as a pair in a specific size and are sealed in a sterile package. Surgical gloves are most often used for sterile field surgery to prevent a transfer of an infectious pathogen to a surface of a surgical wound from a surgeon's hands. Nonsterile latex medical gloves are also known in the field as examination gloves; they are used during nonsterile procedures; are made available usually in a size that can suitably fit either hand and are often packaged in bulk, for example in quanities of 50 per box. Non-sterile procedures include the medical examination of human body surfaces, body invaginations and body orifices; nonsterile medical gloves are also worn for protecting the hands of medical, research or hospital workers from contact with hazardous substances and surfaces. Examples of hazardous substances and surfaces include but are not limited to the following examples: biological waste products such as feces and urine, soiled wound dressings, garments or other materials, syringe needles, other medical devices, irritating or toxic liquids or chemicals, biological toxins, radioactive substances, and infectious pathogens. For the present invention, the term "infectious pathogens" is meant to include but is not limited to the following pathogens: viruses, bacteria, fungi, yeasts, rickettsia, prions, multicellular parasites, the spores of infectious pathogens, and the like.

At least three kinds of glove wall failure are known currently plague the currently known types of medical gloves. First, about two percent of standard latex gloves have inherent microscopic perforations after manufacturing that can be easily be permeated by small infectious pathogens such as a virus. Secondly, during their use, medical gloves may acquire additional perforations, small tears or small punctures which may go unnoticed but could provide a pathway for infectious pathogens to contact the hands of the glove wearer, particularly when the glove is contacted by bloody contaminated body fluids containing the infectious pathogen. If an infectious pathogen contacts human skin, the individual may eventually become systemically infected with the pathogen. Thirdly, if the glove is accidentally punctured by an object that is contaminated with an infectious pathogen, a gloved hand may become contaminated with an infectious pathogen. When a glove wall is punctured, the glove puncturing object may have a sharp edge like a hypodermic needle, suture needle, or scapel blade but an object with blunt edges can also puncture a glove wall. When the currently available medical gloves are worn on the hands, the gloves are not designed nor have the capacity to protect the hands when a glove is punctured by an object that is contaminated with an infectious pathogen.

The prevalence of vital disease caused by infectious pathogens in the human population has created an urgent need for more protective medical gloves that retain their medical utility. Currently, the most feared infectious pathogen is the human immunodeficiency virus (HIV). When a human is infected with HIV, a gradual destruction of the human immune system results over several years and this leads to Acquired Immune Deficiency Syndrome (AIDS), an illness which is generally ultimately fatal. In general, antiviral medical treatments are of limited utility. Vaccines are of limited utility because the HIV surface proteins mutate quickly and immunologically resistant strains of HIV evolve. Thus there is no known medical cure for HIV infection. A person who tests positive for HIV antibodies knows that they have been exposed to and probably harbor HIV in their body. Hepatitis B virus (HBV) is another virus that can lethally infect a human. There is an effective anti-HBV vaccine, but the vaccination treatment is a prolonged and expensive process. Better medical gloves could help to lessen the chance of vital infection. Likewise, better medical gloves would be useful to lessen the chance of infection from any infectious pathogen.

Medical gloves are commonly made from elastomeric materials such as latex rubber or plastic. Materials for a glove may also be obtained from a plant fiber such as cotton, from an animal secretion such as silk, from an animal tissue such as the skin or intestine, from a mineral or from a metal. The material(s) used to manufacture a medical glove should be flexible and should be capable of being made into a fiber or a thin sheet.

A second pair of gloves may be worn over the first pair of gloves to increase the thickness of their physical barrier protection. Multiple pairs of medical gloves can be worn provided that fine dexterous hand work can still be done. However, if two or more pairs of gloves are worn, the medical work by the gloved hand can become difficult and tiring.

Thick-walled work gloves have been constructed using the same materials that can be used to make thin-walled gloves. However, thick-walled gloves are inflexible and this property has generally limited their use by most medical doctors, health care workers, skilled workers and the like workers. A number of thick-walled work gloves have been developed to protect a hand from a serious cut or from a puncture wound by an object. For example, thick-walled cut-resistent gloves have been developed to protect the hands in animal slaughter houses where meat is manually cut (See U.S. Pat. No. 4,526,828 and PCT WO 91/10409). However, a puncture-resistant glove has not been developed that is also flexible to the degree needed by skilled medical personnel and the like who must use there hands skillfully and require protective gloves.

A glove in accordance with the present invention is relatively thin-walled and flexible so that the glove can be comfortably worn and easily used by medical personnel and the like workers as are conventional medical gloves. In addition, like a conventional medical glove, the present invention is capable of becoming punctured by an object.

The present invention has important, novel additional functions. Generally when an object punctures a glove in accordance with the present invention, the glove by a number of processes can immediately and automatically begin to help to protect the hand and any hand wound beneath the glove from becoming infected with an infectious pathogen should the object have been contaminated with an infectious pathogen.

A recent study of accidental blood contact during hospital surgical procedures in burn, trauma, orthopedic, general, gynecology, and plastic surgical services concluded that surgical gloves are an important means for preventing a substantial percentage of the blood contacts with the hands (Panlilo et al, 1991). Blood and body fluids can be contaminated with infectious pathogens such as HIV (also sometimes known as the AIDS virus) and the Hepatitis B virus. Because many substances or material objects can temporarily harbor an infectious pathogen, medical workers are made aware of the risks of becoming contaminated from contacting soiled objects and body fluids from infected individuals. Medical workers are advised to wear medical gloves in any environment which may contain infectious pathogens (Panlilo et al., 1991).

The United States Center For Disease Control (U.S. CDC) has issued guidelines for the prevention and control of nosocomial infections, for hospital environment control, and for control of surgical wound infections (See publications by Simmons, B. P., 1983). The U.S. CDC has reported that a clean wound (a wound that is initially pathogen-free) has only a 1 to 5 percent average risk of becoming infected whereas a contaminated wound (a wound exposed to an infectious pathogen) has a 15 to 17 percent average risk of becoming infected. Furthermore, it was found that a dirty wound (a wound exposed to biological or environmental liquid and solid waste which may be contaminated with an infectious pathogen) has more than a 27 percent average risk of becoming infected. Therefore, an infection is much more likely to occur in a dirty or contaminated wound than in a clean wound. Surgeons have administered an antiseptic solution directly into a wound as an irrigation solution (See also Maki, D. C, 1976). Furthermore the U.S. CDC guidelines advise doctors and health care workers to wash their hands with an antiseptic detergent to reduce the microbial (infectious pathogen) contamination on their hands before they wear medical gloves. Thus the cleaning of a wound and antiseptic decontamination of the hands are established treatment means for decreasing the risk of infection in a wound. The U.S. CDC has also suggested that antiseptics are more effective antimicrobial agents than soap and water, but has pointed out that frequent exposure of the skin with an antiseptic is often more irritating than skin exposure to soap and water. Thus, prolonged or repeated skin exposure to antiseptic compositions is ill-advised.

In 1987, the U.S. CDC issued the recommendation that medical examination gloves be worn as a "Universal Precaution". To adhere to the Universal Precaution Guidelines, doctors and other medical personnel are expected: (1) to assume that each patient is infected with human immunodeficiency virus (HIV) and thus to wear a new pair of gloves with each new patient, and (2) to remove their gloves and to wash their hands immediately if their hands appear to have become contaminated with blood or other body fluids (See Bartlett, J. G., 1988).

Although medical workers are well aware of the utility of an antiseptic in the prevention of skin infection and wound infection, medical glove wearers may not always be able to comply with the proposed U.S. CDC guidelines in a competent manner. It may be inconvenient or impossible for a glove wearer to immediately remove a damaged or contaminated glove during surgery or during a stressful medical emergency. Such a delay in glove removal may be dangerous for the glove wearer. The time delay may permit the blood circulation of the glove wearer to become more contaminated with an infectious pathogen. Delayed disinfection of the hand or hand wound with an antiseptic may be an ineffective means for preventing the systemic spread of an infectious pathogen in an individual. The glove wearer may delay glove removal and decontamination of the hand or hand wound with an antiseptic because the glove puncture was not perceived; the the wound may not be not felt immediately or bleeding from the wound may be so minor that it is not immediately noticed. It is thus a serious problem that some medical glove wearers may unwittingly delay a medical treatment of their gloved hands when a hand has become injured by a pathogen-contaminated object.

There has been an obvious increase in the wearing of medical gloves in many health care work environments following adoption of the Universal Precautions Guidelines and following the epidemic growth of AIDS in the human population. Because it is not known with certainty exactly which work environments can harbor an infectious pathogen such as HIV, medical gloves are now routinely worn by many medical or public workers whenever they suspect they may be at risk of any kind of accidental infection by any infectious pathogen. The present invention may be usefully worn in many work environments and during many kinds of work. The work environments and kinds of work in which gloves in accordance with the present invention may be used include but are not limited to the following examples: hospitals, medical clinics, private doctor offices, emergency medical work, medical ambulance work, fire rescue work, medical practice areas involving AIDS patients, surgery, gynecology, human fertility work, urology, general medicine, pathology, epidemiology, microbiology, neurology, orthopedics, radiology, ontology, nursing, dentistry, podiatry, psychiatry, psychiatric hospitals, hospices, other medical practices and specialties, kidney dialysis centers, diagnostic medical imaging-testing and operations facilities, hospital emergency waiting rooms, emergency hospital ambulatory care, clinics for drug rehabilitation, donor organ and tissue preservation banks and labs, blood banks, blood testing and related analytical chemistry labs, sperm banks, sperm testing labs, basic and clinical medical research labs, medical instrument cleaning, sharpening and repair facilities, hospital patient rooms, hospital operating rooms, cleaning and maintenance work, hospital laundries, hospital cafeterias, other hospital patient food service work, hospital morgues, funeral homes and related work areas that study or handle dead human bodies and tissues, medical and public waste or garbage collection areas, disposal areas and containers for human blood and disposible medical utensils, work with blood products, urine products or any human body products, hospital trash and other disposible waste areas which might contain medical waste, work with sharp contaminated objects such as needles, syringes, wires, catheters, and intravenous sets, plastic and glass tubes and pipettes, glass slides, scalpel blades, and the like; disposible medical instruments and work areas involved in surgical instrument handling, repair and cleaning, clothing and medical assist areas; areas of medical garbage removal and medical sanitation work, medical work in nursing or retirement homes, and cleaning or industrial operations in any building where there may be any risk of a pathogenic infection. Surgical gloves and/or examination gloves in accordance with the present invention may also be used in animal medicine and during general work with animals in research, on farms or ranches with animals, in veterinary and animal husbandry practices and pet stores, in work with zoo animals, and in similar work where there may be some risk of contact with an infectious pathogen. Gloves in accordance with the present invention may also provide useful protection from physical contact with infectious pathogens that may exist in potentially infectious, nonmedical technical areas, scientific areas and other work areas including but not limited to the following examples: industrial, military, or other research work that involves work with infectious pathogens used in molecular biology or molecular genetics, recombinant molecular genetics, fermentation and vaccine production; the facilities include any government, military, commercial, industrial, or biotechnological production, research and testing areas. Medical gloves in accordance with the present invention are also useful protective hand wear in areas or in work which may include but is not limited to the following examples: public and business building maintenance work and cleaning, outdoor public areas work, restaurant work, sports clubs, spas, health clubs, massage parlors, building rehabilitation and clean-up work; guard work in jails, prisons, and other crimminal confinement facilities. Gloves in accordance with the present invention may be useful during travel in public or private vehicles used to provide surface, underground, water, underwater, air, aerospace or even outer space transport conceivably may harbor infectious pathogens.

Conventional medical gloves are often worn to protect the hands of an individual from coming into physical contact with an infectious pathogen that infects another individual. Gloves in accordance with the present invention can provide superior protection for the glove wearer compared to conventional medical gloves when the glove wearer is within possible contact of individuals who are at risk of being infected with an infectious pathogen. Individuals who at risk of being infected with an infectious pathogen include but are not limited to the following examples: a person infected with the AIDS virus, a person infected with hepatitis B virus or other viruses, a person with a bacterial infection, a hospital patient, a health care patient, an intravenous drug user, a prostitute, a gang member, a homeless person, a mentally-ill person, a person suspected of or engaged in criminal activity, a captured or convicted or imprisoned criminal; an illegal immigrant, an immigrant from a known HIV-infested population, a new immigrant, a homosexual or bisexual individual, a sexually promiscuous individual, and a chronically-ill, elderly or incapacitated person who is at an increased risk of harboring an infectious pathogen. In addition, according to researchers based upon a U.S. survey of more than 11,000 students, it is believed that one in five American teenagers are at higher risk for acquiring AIDS because they have had sexual contact with several partners (four or more persons) during their teenage years (See *The New York Times*, Medical Science Section C3, dated Apr. 14, 1992 by Associated Press). Thus the risk among teenagers for acquiring AIDS may increase as more and more teenagers become carriers of the AIDS virus.

A glove in accordance with the present invention may also usefully protect an individual under other circumstances. Animals, plants, soil, water, the air, and various forms of environmental pollution are capable of supporting colonies of infectious pathogens which may infect an individual. Thus workers in many nonmedical environments can also become contaminated with an infectious pathogen. Such nonmedical workers include but are not limited to the following workers: law enforcement workers, police, state trooper, national guard, military personnel, traffic police, transit police, jail and prison workers, park workers and park cleaners, sanitation workers, city morgue workers, hospital morgue workers, funeral home workers, and cemetery workers, waste and water treatment facility workers, street cleaners, sewer workers and other municipal workers, persons cleaning public bathrooms and portable toilet maintainance workers.

In addition, flexible protective medical gloves in accordance with the present invention can be used by any doctor, dentist, health care worker and the like or other individual who choses to continue working after they have tested seropositive with an infectious pathogen such as for example HIV or hepatitis B virus (See News York Times article by Jane Gross, dated Aug. 18, 1991). It is particularly important for infected medical personnel to wear protective medical gloves so that they do not transmit their infection to another person.

If an object cuts, or otherwise penetrates a thin medical glove wall while it is being worn on a hand, the physical barrier protection provided by the glove is immediately lost. Such an accident to a glove while it is being worn may also wound the hand and this wounding may expose the blood circulation of the individual to the surface of the glove-puncturing object; becoming wounded is particularly traumatic and serious if the surface of the glove-puncturing object may be contaminated with an infectious pathogen such as HIV.

Medical personnel know that wearing a conventional medical glove can not adequately protect a hand from a glove-puncturing object contaminated with HIV. HIV contamination to a gloved individual can take place if a syringe needle contaminated with AIDs-tainted blood punctures the glove and wounds the hand. A variety of medical objects have caused an instant HIV inoculation to the hands of health care workers wearing standard surgical or examination gloves (See Henderson et al., 1990; Beekman et al., 1990; Panlilio et al., 1991).

For the present invention, the term glove wall puncture is broadly defined to encompass a glove wall puncture caused by any object or by any process. A glove wall puncture may be caused by any physical object capable of cutting, biting, abrading, puncturing, stabbing, crushing, or otherwise physically penetrating the glove wall. When such objects are contaminated with an infectious pathogen, they can act as a carrier for the transfer of the infectious pathogen to the hand and the hand wound. Alternatively, the glove wall puncture may be caused in the absence of a solid physical object, for example by any process that helps to cause a hole in the glove. Processes that may help to cause a hole in a glove include but are not limited to the following: a chemical reaction with the glove wall material, a solvent dissolution of the glove wall, a change in the ambient gas pressure or liquid pressure on a glove wall surface, passage of a powerful electrical shock through the glove wall, a thermal melting or burning of the glove wall, or a low temperature freezing followed by fragmentation of the glove wall. In the forementioned examples, the process helping to or actually causing the glove wall puncture may not actually transfer an infectious pathogen to the hand or to the hand wound. In general a glove wall puncture always creates the access means through the glove wall for an infectious pathogen from the exterior surface of the glove to then contact the hand or a hand wound.

Health care workers and medical doctors in particular, know that hand wounding is a common accident, one that they often experience a number of times each year in their work environments because conventional medical gloves are not puncture-resistant and because this is a common risk in their work environments, particularily with sharp objects (Panlilio et al., 1991; see especially Wright et al., 1991). For the present invention, the term "hand" is broadly defined to encompass all portions of an arm and a hand that may be covered by a glove in accordance with the present invention; thus use of the term "hand" for some embodiments of the present invention may refer to the fingers, all surfaces of the hand, the wrist, the forearm, and may refer even to the surfaces of the arm up to the armpit and the shoulder.

Health care workers and other professionals who care for patients with AIDS know that they may become infected with the AIDS virus (HIV) from their work with AIDS patients. It is clear that as a result of the AIDS epidemic, medical doctors and health care workers now work with increased anxiety and fear of contracting AIDS (See "Fear of Disease Changes How Doctors Work, New York Times dated Apr. 7, 1992, page 1, by Lisa Belkin). Medical workers know that an accidental hand wound during their professional work may infect them with HIV and shorten their lives (Gerberding and Schecter, 1991). Each time a gloved hand is wounded by an object contaminated with blood or other body fluids, the wounded medical worker must psychologically deal with the possibility that the wound was contaminated with HIV, and that they are at some generally-unclear risk of acquiring an HIV infection. Thus, there is clearly an urgent need for a more protective medical glove than is currently available, that can provide superior protection for the glove wearer hand when their hand is wounded by an object that may be contaminated with an infectious pathogen such as HIV.

Some medical doctors and health care workers have indicated they would not disclose if their hand was wounded or injured during work by an object possibly contaminated with HIV nor would they disclose to their co-workers if their blood were to test positive for antibodies to HIV antigens because such disclosure would reveal to their co-workers that they might have a systemic HIV infection which could threaten their employment in health care (See Orentlicher, D., 1991; and New York Times article by Jane Gross, dated Aug. 18, 1991). Thus, there is a tendency for HIV infections to go unreported by medical workers and this would suggest that data gathered to estimate the incidence of accidental glove punctures among health care workers would be underestimated.

As mentioned, medical personnel work in environments having sharp medical instruments and needles which can readily puncture a standard medical glove on a hand and cause a hand wound (See Gerberding and Schecter, 1991). The reported incidence of accidental skin punctures to hospital surgical personnel in three major municipal hospitals (in San Francisco, Albuerque, and Atlanta) has averaged 2 to 5 injuries per 100 procedures (Panlilio et al., 1991; Gerberding et al., 1990; Gerberding and Schecter, 1991). These hospitals have also reported that occupational exposure to blood occurs often in surgical settings (Gerberding et al., 1990; Gerberding and Schecter, 1991; Panlilio et al., 1991). Accidental blood contact between a patient having HIV and workers in other more casual (nonsurgical) medical settings has been predicted to increase in view of the epidemic spread of HIV infection in the United States and in the World (Gerberding et al., 1990).

Three known factors that can affect the risk of a medical worker becoming infected with an infectious pathogen are (1) the prevalence of blood-borne infection in the patient population under treatment by the medical worker, (2) the frequency and types of hazardous exposure that the medical worker is subjected to, and (3) the risk of infection that accompanies each exposure to the medical worker (Gerberding and Schecter, 1991). It is thought unlikely that medical personnel can control the first two factors and still remain valid health care workers. It is one object of the present invention to help to lower the worker's risk from the third factor, namely a glove in accordance with the present invention may be used to try to help to lower the risk of infection that accompanies each hazardous exposure to a medical worker's hand.

The risk of systemic HIV infection to an individual wounded on a hand from a single hollow needle stick has recently been estimated to average roughly 0.4 percent (1 occurence in 250 events). This risk estimate was calculated from observations of documented needlestick wounds that were contaminated with blood from patients having an advanced stage of HIV infection during which their blood had an elevated HIV titer (Beckman et al., 1990; Henderson et al., 1990). This estimate is an underestimate because some hand injuries will not be reported and this study therefore underscores the real risk that medical workers experience.

An analysis of the risk of infection that accompanies each exposure of a hand and a hand wound to an infectious pathogen has been conducted, based upon an in vitro study of glove wall punctures by needles. The study found that the risk was influenced by several variables. An important variable was the volume of infectious blood transferred by the needlestick (See Mast and Gerberding, 1991). Other important variables included (1) the titer of the infectious pathogen in the contaminating blood, (2) the needle type and size, and (3) the depth of skin penetration by the pathogen contaminated object. Other observations have shown that wearing a standard medical glove on the hand can reduce the volume of blood transferred to the hand wound by about 50 percent (See Gerberding and Schecter, 1991). When two pairs of standard medical gloves were worn on the hand, the contamination of the hand wound by blood was further reduced to between 20 to 40 percent, (Gerberding and Schecter, 1991; Mandelbrot et al., 1990). Thus, studies have found that wearing two standard gloves on a hand can reduce, but does not adequately protect, a hand when it is wounded by a blood-tainted needle. The hand can become contaminated with a substantial fraction of the foreign blood, infectious pathogens or other substances present on the glove-puncturing blood-tainted needle. In view of the (a) incomplete protection that conventional gloves can provide, (b) the frequency of accidental hand wounds by gloved health care workers, and (c) the increasing incidence of HIV infection in the human population, it is likely that the probability of a health care worker becoming infected with HIV during work from HIV contamination of a hand wound will increase. The medical profession is concerned about their risk of HIV infection from a medical glove puncture and would like their risk to be reduced (See Orentlicher, 1991).

To have medical utility, a protective medical glove should retain the flexibility and the comfortability characteristics of conventional medical gloves. The prior art has not disclosed a flexible protective medical glove having a wall that is capable of storing a non-liquid antiseptic composition which comprises an antiseptic. The prior art has not disclosed the uses for a flexible protective medical barrier glove having a wall that stores a non-liquid antiseptic composition which comprises an antiseptic. When a glove puncture is caused by an object, the present invention can provide a non-liquid antiseptic composition capable of contacting and coating the object puncturing the flexible glove; useful as a treatment means for the hand and the hand wound that may occur when the flexible glove is punctured and/or the hand is wounded by the object puncturing the flexible glove; and particularily useful when the object may be contaminated with an infectious pathogen.

Related additional prior art is described below, but is not identical to the present invention. In view of the prior art, the subject matter of the present invention as a whole would not be obvious to persons of ordinary skill in the art pertaining to the subject matter of the present invention at the time of the invention.

A protective gel composition has been disclosed (U.S. Pat. No. 5,019,604 issued May 28, 1990 to G. M. Lemole) for coating the skin prior to covering the hands with standard surgical gloves. In one example, the composition contains lanolin, liquid silicone, polypropylene glycol monoleate, polytetrafluoroethylene powder in microspherical form, zinc oxide powder, anti-bacterial agents and antiviral agents with a preferred agent being nonoxynol-9. The composition forms a water repellent coating on the skin to prevent the skin contacting body fluids such as blood and blood products that may penetrate the gloves and otherwise expose the skin to harmful microbial and vital infections. The use of a protective gel to continuously contact the skin with chemicals may be irritating to the hands. After glove removal, the gel coating the skin must be washed off. Some individuals may also find that the number of steps required to use and remove the gel is time consuming or disagreeable. Use of the gel composition between two gloves was not suggested.

Use of antiseptic-coated gloves has been disclosed in a study of surgical hand hygiene (*J. Hospit. Infect.* 1988, 11 Supp. A:244–250 by Newsom et al.). Gloves were coated with solid cetylpyridinium chloride and surpressed skin flora counts after prolonged operations in comparison to standard gloves, but the solid antiseptic coating may cause hand irritation after prolonged contact. Use of such antiseptic between two gloves was not suggested.

Use of the antiseptic 4.0% chlorhexidine gluconate detergent formulation containing 4.0% isopropyl alcohol (Hibiclens/Hibiscrub) and the antiseptic 0.50% chlorhexidine gluconate in 70.0% isopropyl alcohol with emollients (Hibistat/Hibisol) as a skin treatment has been disclosed (*J. Hospital Infection*, 1990, 15:279–282 by Montefiori DC et al.). This antiseptic composition was found to inactivate HIV in experimental cell cultures after 15 seconds when used at 1:100 and 1:5 dilutions. Use of such antiseptic between two gloves was not suggested.

A sterile glove has been disclosed in which the antibacterial agent zeolite is immobilized in a plastic film on one or both surfaces of the glove; useful for handling food, for work in a kitchen or for medical purposes (U.S. Pat. No. 5,003,638 issued Apr. 2, 1991 by T. Miyake and T. Yamamoto). According to the Merck Index (8th Edition), zeolite is a hydrated dust or powder of alkali aluminum silicate. An immobilized thin layer of antibacterial agent can not help to prevent a hand wound infection.

A glove has been disclosed which was made by first immobilizing an anti-microbial agent into rubber and by then solidifying the mixture into a glove (U.S. Pat. No. 5,031,245, issued Jul. 18, 1991 by Milner, R.). The glove was reported to be an improved barrier to HIV. A non-ionic, sparingly water-soluble antimicrobial agent that does not coagulate natural rubber latex such as chlorophene, dichloroxylenol, hexachloraphane was used; diphenyl derivatives may be halogenated and used such as 0.1% to 10% by wt. 2,4,4'-trichloro-2'-hydroxyphenyl ether, diacetylaminoazotoluene, triclocarban and triclosan. The surface of the glove was dusted with a powder containing an anti-microbial agent such as chlorhexidine digluconate and cyclodextrin. The antiseptic dust on the glove surface contacts the hand while the glove is worn and may irritate the skin.

A multilaminar hybrid glove has been disclosed having at least an outer rubber layer, an inner rubber layer and at least one intermediate (cotton or Kevlar plastic) material layer layer impregnated with a gel containing 4 percent nonoxynol-9; regions of the glove may be protected with an armor of fungicide-coated, puncture-resistant Kevlar plastic fabric (*Infect. Control Hospital Epidemiol.* 1991, 12(7): 435–438 by Johnson et al., 1991). In vitro tests found that the glove with Kevlar resisted some needlestick punctures. In vitro tests found that the glove reduced the transfer of HIV from a solid needle tip to a culture dish by chemical inactivation of the virus on the needle when the needle contacted the gel containing nonoxynol-9 in the cotton layer. Results using "hollow" syringe needles were not obtained and the authors indicated they could not predict such results without additional study. The authors disclosed that their gloves were too stiff and too thick-walled to function on the dominant hand of a surgeon; they suggested that thinner, more surgically acceptable intermediate gloves were needed; but these three-layer gloves containing nonoxynol-9 gel antiseptic were not flexible enough for the needs of a medical worker performing manual skilled work.

The present invention is directed toward providing novel flexible protective medical glove designs and methods for their use. A glove in accordance with the present invention can provide a non-liquid antiseptic composition treatment to a hand when the glove wall is punctured. The subject matter of the present invention as a whole has not been made obvious nor has it been suggested by the prior art for medical gloves or for antiseptic compositions used on the hands. The flexible protective medical gloves comprising the present invention are provide a major improvement in medical glove protection technology because the present invention may be useful as an automatic means for helping to protect a hand from becoming infected by a glove-puncturing object when the object is contaminated with an infectious pathogen. Use of the gloves does not constantly expose the hands to a potentially irritating antiseptic. The non-liquid antiseptic composition in the gloves can not flow from a glove wall puncture as a liquid could. However, for some embodiments of the present invention the non-liquid antiseptic composition may be capable of automatically expanding following a glove wall puncture so that non-liquid antiseptic composition is expelled from the glove wall puncture onto the hand and into a hand wound should one occur.

SUMMARY OF THE INVENTION

It is an object of the present invention to provide a flexible protective medical glove having a thin flexible glove wall comprising at least an outer glove layer of a first material having a thickness of between about 1 mil (1 mil is one-thousandth of an inch) to about 40 mils and at least an inner glove layer of a second material having a thickness of between about 0.3 mils to about 30 mils wherein the first material and the second material form at least the walls of a compartment storing a non-liquid antiseptic composition or at least some of the material components capable of comprising the non-liquid antiseptic composition. The compartment(s) storing the non-liquid antiseptic composition, or its components in some separate fashion, may become mixed together to some degree during a glove wall puncture. Thus the present invention has the capability to provide some non-liquid antiseptic composition in the compartment along at least some portion of the glove wall puncture. As a result of a glove wall puncture a suitable amount of the non-liquid antiseptic composition is formed. The compartment(s) generally has a thickness of less than 100 mils; it is expected that the compartment(s) may become temporarily compressed during glove wear so that compartment(s) thickness is capable of varying; in addition, the compartment(s) in some portions of the glove may be expanded due to glove design, or during the wearing of a glove to a thickness exceeding 500 mils. At the back end of a glove where the hands are first inserted, the compartment(s) may be open or may be closed. Alternatively, the glove compartment may be optionally capable of being opened or closed using for example a zip-lock sealing mechanism or other sealing seam mechanism, to allow the glove wearer to increase or reduce the amount of non-liquid antiseptic composition in the glove. Preferably the compartment(s) is closed. A glove in accordance with the present invention can be as flexible a conventional medical glove; this is important because glove flexibility permits a gloved hand to easily and adequately perform delicate, dexterous and complex hand work including for example, the hand work of a surgeon, a medical doctor, a dentist, a laboratory worker, a health care worker, a law enforcement worker, a hospital worker and like workers. It is envisioned that the glove wall could be constructed from almost any material or combination of materials provided that at least the surface of the inner glove layer and at least the surface of the outer glove layer are not liquid permeable. Most preferably at least the inner and the outer glove wall layers are made of thin flexible layers of rubber and/or plastic materials.

The non-liquid antiseptic composition comprises an antiseptic in a non-liquid composition. Preferably the antiseptic comprises at least one of the following antiseptics: povidone-iodine, elemental iodine, sodium iodide, potassium iodide, sodium hypochlorite, nonoxynol-9, and chlorhexidine gluconate. For the present invention the antiseptic composition is termed a "non-liquid antiseptic composition" to distinguish its physical properties from the physical properties of a liquid antiseptic compositions. Once formed, the non-liquid antiseptic composition behaves as a non-liquid meaning that the complete antiseptic composition is incapable of flowing like a liquid from a glove wall puncture. For the present invention, the term "non-liquid antiseptic composition" is not meant to imply that any of the components which comprise the non-liquid antiseptic composition are necessarily non-liquid. Rather, the final assembled or activated, non-liquid antiseptic composition will have the inability to flow like a liquid. Thus, one or more liquids may be used to form the non-liquid antiseptic composition, such as for example ethanol, water, isopropanol, or a mixture thereof. Preferably the non-liquid antiseptic composition further includes at least one surface active agent. The non-liquid antiseptic composition may also contain one or more of the following substances: an organic silicone, an organic solvent, a salt, an acid, a base, a pH buffer, a preservative that can help to stabilize the antiseptic activity, a metal ion chelator, a catalyst, a sticky chemical additive, a gelling agent, a thickening agent, a hardening or stiffening agent, a humectant, an emulsifier, a viscosity-modifying agent that may be used to increase the coating of the glove puncturing object by the the liquid antiseptic composition, a chemical scent that can help to increase the smell or render the odor of the liquid antiseptic composition more pleasant, a gas generation system, a foaming agent that can help to better mix the non-liquid antiseptic composition with the contaminants on the hand and in the hand wound containing infectious pathogen, glycerin, a soap, a detergent, a pain-causing agent (algesic), a coloring agent, and/or a vasoconstricting agent.

The present invention also provides a new method for protecting a gloved hand from an infectious pathogen in the event of glove damage while the glove is being worn.

It is another object of the present invention to also provide methods for the use of the present invention. Gloves in accordance with the present invention, like standard medical gloves, can provide a useful thin physical barrier form of protection to the hands. It is an object of the present invention to minimize contact between the hand and the non-liquid antiseptic composition to reduce unnecessary irritation of the hand by the antiseptic, until such time that the wall of the glove is punctured by an object, and then antiseptic is needed to contact the hand. For some embodiments of the present invention, when an object punctures a glove wall of the invention, the present invention has the capability to automatically begin a non-liquid antiseptic composition treatment of the hand or the hand wound should a wound occur.

The treatment of non-liquid antiseptic composition from the glove should be capable of inactivating, killing, and/or otherwise destroying the infectious pathogen that the non-liquid antiseptic composition may contact. The non-liquid antiseptic composition should be capable of disabling the contacted infectious pathogen so that the infectious pathogen from the object is no longer a danger to the hand and the hand wound of the contaminated individual. For the present invention, the term "infectious pathogan" has a broad meaning intended to encompass known and to be discovered pathogenic microorganisms which would include prions and viruses as well as the biochemical cofactors or molecular fragments that can be synthesized or released by an infectious pathogen or by other biological cells or that may arise by other biosynthetic means that could be considered to be infective; the term is intended to include biochemical cofactors and chemical fragments including but not limited to the following examples of infective materials as well as their related biochemical machinery: deoxyribonucleic acids (DNA), ribonucleic acids (RNA, mRNA, tRNA and the like), protein cofactors, and the enzymes that act upon DNA, RNA, mRNA, tRNA and like nucleic acids in any form or conformation which may alter the potency of a pathogenic infection. The non-human proteins that help HIV to inhibit the human immune system are considered for the present invention to be protein cofactors and are considered relevant infective materials. Some of these proteins may affect the binding of HIV to human cells. Damage to these proteins by the non-liquid antiseptic composition may have anti-infective utility. Thus, the term "infectious pathogen" for the present invention is broadly defined to include at least the following infectious pathogens in any of their physical forms: viruses, bacteria, yeasts, molds, algae, other fungi, multicellular parasites, rickettsia, prions, the spores of infectious pathogens, and includes any of the biochemical molecular fragments of an infectious pathogen (i.e., DNA, the various RNA molecules, associated DNA and RNA enzymes and associated proteins) that could contribute to the infectivity of an infectious pathogen. For some embodiments of present invention, it is a preferred object that the non-liquid antiseptic composition has potent antiviral or viricidal activity against the human immunodeficiency virus (HIV), and/or the Hepatitis B virus.

An object of the present invention is to help to protect the hand and a hand wound from becoming infected by a glove puncturing object that is contaminated with an infectious pathogen should the object puncture the glove wall and contact or wound the hand. When the glove wall is punctured by an object, the object may then wound the hand and come into contact with the blood circulation of the individual. In passing through the glove wall, the object can become coated with non-liquid antiseptic composition and can carry some non-liquid antiseptic composition along with the infectious pathogen contamination that may be present on the object, to the hand and into the hand wound; useful as a automatic and immediate non-liquid antiseptic composition treatment to the hand and the hand wound that may help to immediately provide a protective treatment to the gloved individual so that the individual does not acquire a systemic infection from the infectious pathogen on the glove-puncturing object.

In one embodiment according to the present invention, the glove is comprised of a liquid-impermeable outer layer of a first material and a liquid-impermeable inner glove layer of a second material wherein the first material and the second material form the walls of a compartment(s) capable of containing a non-liquid antiseptic composition; the compartment(s) contain or may store the non-liquid antiseptic composition. The glove also has the capability to provide a coating to at least a portion of the object puncturing the glove wall; the coating comprising the non-liquid antiseptic composition; the coating on the object providing a means for automatically and immediately transfering some of the non-liquid antiseptic composition onto the hand and into the hand wound resulting from the object puncturing the glove while the glove is being worn; the non-liquid antiseptic composition transferred to the hand and the hand wound having the capability to provide a treatment of non-liquid antiseptic composition to the hand and the hand wound which may have become contaminated with an infectious pathogen transferred from the glove-puncturing object. It is desirable that the non-liquid antiseptic composition have some capability to dissolve into or become liquified upon contact with the hand or upon contact with the glove-puncturing object or upon contact with hand fluids or blood of the hand wound due. The glove has the additional capability of treating the hand and the hand wound with the non-liquid antiseptic composition when the object punctures the glove wall, when the object contacts the hand, if and when the object wounds the hand and whether or not the object actually contaminates the hand and the hand wound with the infectious pathogen. The non-liquid antiseptic composition automatically and immediately transferred by the glove-puncturing object from the glove to the hand and the wound on the hand, may be useful by beginning to help to protect the hand, the hand wound, and thus the systemic circulation of an individual by killing, inactivating and/or otherwise destroying without undue delay the infectious pathogen that may have contaminated the hand and the hand wound as a result of a glove-puncture by an object that may be contaminated with an infectious pathogen.

In a second embodiment according to the present invention, the glove can provide a non-liquid antiseptic composition such as a foam, a paste, a gel, an ointment or other greasy composition which is capable of optionally being redistributed within the compartment(s) of the glove by the manual application of pressure to the glove wall compartment(s) in order to force the non-liquid antiseptic composition in the compartment(s) to accumulate near the glove wall having the hole should one be caused by a glove-puncturing object. As a result, the non-liquid antiseptic compostion can then optionally be forcibly extruded from the punctured glove wall having the hole onto the hand and into the hand wound; the additional non-liquid antiseptic composition contacting the hand and the hand wound may be used to help to provide additional protection to the hand, the hand wound, and the systemic circulation of an individual from an infectious pathogen that may have contaminated the hand and the hand wound when the glove-puncturing object contacted the hand and caused a hand wound. A hand wound is defined for the present invention as at least a degree of damage to the skin that increases the probability that an individual can become infected by an infectious pathogen. A hand wound may or may not cause bleeding of body fluids or blood from the individual.

In another embodiment according to the present invention, the glove contains a non-liquid antiseptic composition which may also contain a pain-causing chemical (algesic agent) such as a potassium salt, formic acid, bradykinin or substance P. One object of the pain-causing chemical is to provide enhanced pain sensation at the hand wound to better warn the glove wearer that they may have suffered a hand wound.

According to another embodiment of the present invention, the glove contains a non-liquid antiseptic composition which may also contain a colored substance such as a dye or an opacifier that can help to visually signal when and where a glove wall has been punctured or damaged; useful particularily for distracted, preoccupied, or overly-stressed individuals needing to wear a medical glove.

According to another embodiment of the present invention, the glove contains a non-liquid antiseptic composition which may also contain a chemical capable of producing a distinctive chemical smell or odor which can be either bad smelling or pleasant smelling. A sudden release of the distinctive chemical odor from a glove puncture can be a useful means for increasing a glove wearer's awareness that a glove may be damaged.

According to another embodiment of the present invention, the glove contains a non-liquid antiseptic composition which may also contain a vasoconstricting agent; preferably a catecholamine such as epinephrine or norepinephrine. An object of the vasoconstricting agent is to reduce blood flow in the hand wound area as a means for limiting the systemic dispersion of the infectious pathogen away from the hand wound by the blood circulation or by the lymphatic circulation of the individual.

According to another embodiment of the present invention, the glove contains a non-liquid antiseptic composition which may also contain a viscosity-modifying agent that can be used to alter the physical properties of the liquid antiseptic composition; this additive can be particularly useful as a means for influencing the thickness of the coating of non-liquid antiseptic composition that can form on the object that punctures the glove wall.

According to another embodiment of the present invention, the non-liquid antiseptic composition may have adhesive properties that allow the non-liquid antiseptic composition to coat or "gum-up" the surfaces of the object that contact the composition as the object punctures the glove;useful so that the contamination including infectious pathogen on the object is less readily spread from the glove-puncturing object when the object contacts the hand or causes a hand wound.

According to another embodiment of the present invention the glove wall has a plurality of glove layers that can act as a structural connection which reconfigures the compartment storing the non-liquid antiseptic composition into a plurality of compartments capable of storing the non-liquid antiseptic composition; useful as a means for selectively partitioning the non-liquid antiseptic composition in the glove wall.

According to another embodiment of the present invention, the glove wall comprises a sponge-like wall structure capable of acting as a structural connection which reconfigures the compartment storing the non-liquid antiseptic composition into a plurality of compartments capable of storing the non-liquid antiseptic composition; the outer and inner surfaces of the glove wall can be coated with a liquid-impermeable coating of a rubber or a plastic material. The actual number of pore-sized compartments, the degree of segmentation of the glove wall into the compartments, and the volume of each subcompartment are not critical limitations for the present invention and may be highly variable.

According to another embodiment of the present invention, the compartment storing the non-liquid antiseptic composition is subdivided into a number of smaller compartments as a means for controlling the distribution and capacity for redistribution of the non-liquid antiseptic composition within the glove wall. Each smaller compartment may be connected to another small compartment by at least one hole so that the non-liquid antiseptic composition can be dispersed between the compartments if desired using a pressure gradient. Some of the subdivided compartments may be closed.

According to another embodiment of the present invention, the compartment storing the non-liquid antiseptic composition is subdivided into a plurality of closed compartments as a means for controlling the distribution or thickness of the non-liquid antiseptic composition within the glove wall.

According to another embodiment of the present invention, the compartment of the glove storing the non-liquid antiseptic composition is connected to an additional compartment of non-liquid antiseptic composition using a tube with an opening whose aperature can be varied as desired or closed entirely.

The subject matter which we regard as our invention is more particularily pointed out and distinctly claimed in the concluding portion of this specification. Other features and advantages are inherent in the protective glove and method claimed and disclosed for its use or will become apparent to those skilled in the art from the following detailed description in conjunction with the accompanying diagrammatic drawings.

DETAILED DESCRIPTION OF THE INVENTION

Figure 1A:
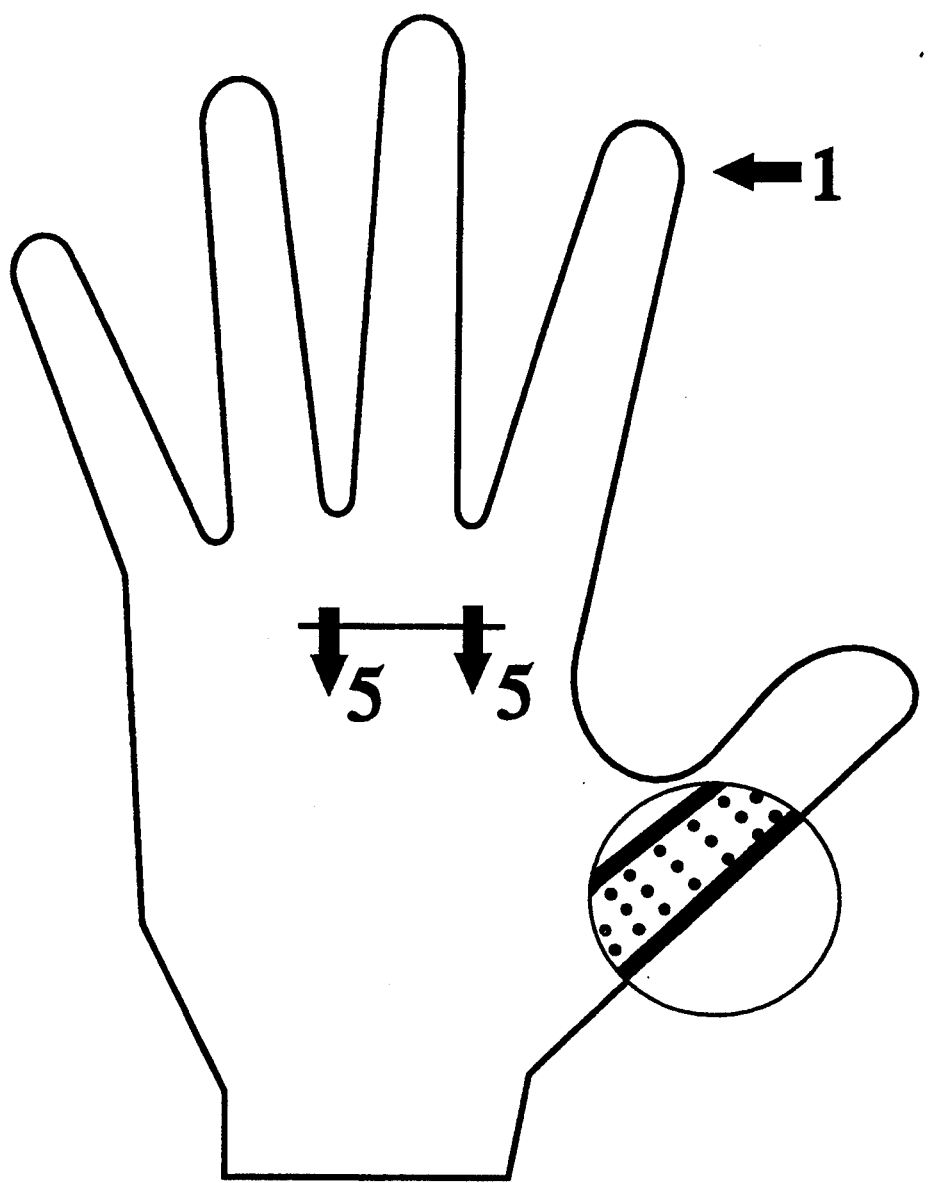
FIG. 1A is a perspective view and a partial enlarged view illustrating a glove containing a non-liquid antiseptic composition between an outer layer of a first material and the inner layer of a second material in accordance with the present invention.

FIG. 1A illustrates a glove in accordance with the present invention; the glove indicated generally at 1 is composed of flexible materials forming a liquid-impermeable wall having the capability to provide a non-liquid antiseptic composition treatment to a hand and to a hand wound underneath the glove while the glove is being worn when the wall of the glove is punctured and/or when the hand is wounded by an object that may be contaminated with an infectious pathogen.

It is an object of the present invention to provide a glove having any conceivable arm length, up to and including a glove having an arm length that can protect the entire arm of an individual up to about the shoulder region of the individual. Whereas the normal length of the glove is between about 8 inches and about 12 inches, the arm-length long glove may be up to 36 inches in length.

A glove in accordance with the present invention can have elastic walls so that one size of the glove may be worn on several different sized hands as can a conventional medical examination glove. Alternatively, a glove in accordance with the present invention can be made available in a number of different sizes as are some conventional medical surgical gloves, so that the glove does not need to be substantially stretched or unduly stressed by the glove wearer in order for the glove to closely fit their hand.

Figure 1B:
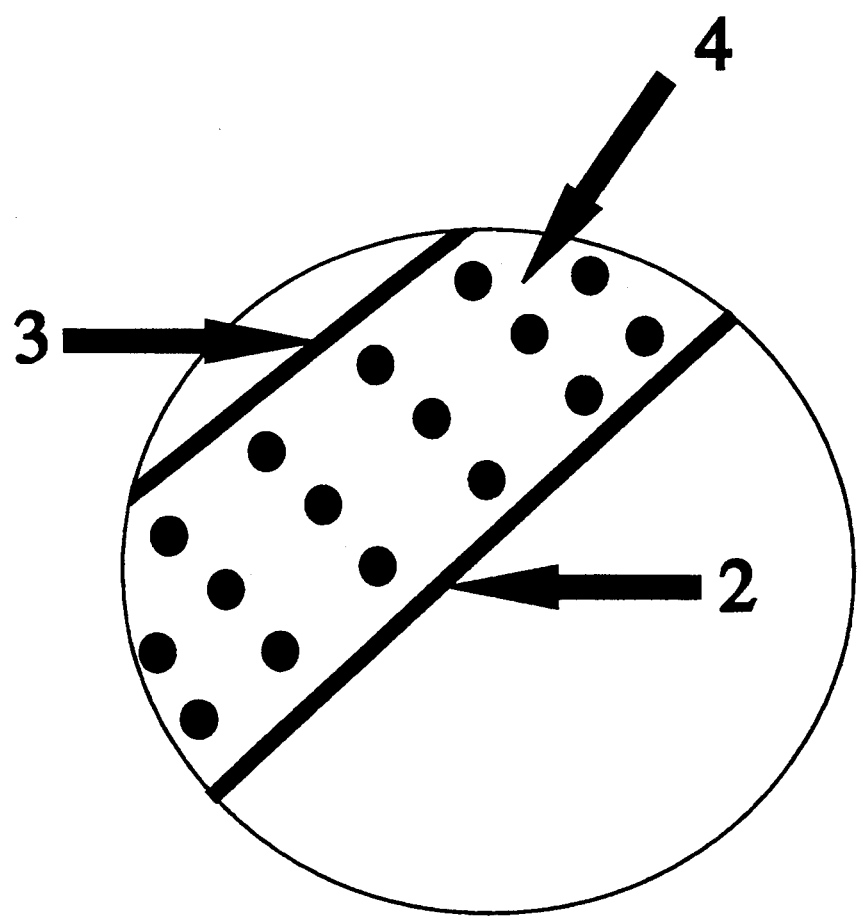
FIG. 1B is a partial enlarged view of the section of a glove wall shown circled in FIG. 1A.

FIG. 1B is an enlarged view of a representative section of the glove wall shown circled in FIG. 1A. FIG. 1B illustrates that the glove wall comprises an outer layer 2 of a first material and an inner layer 3 of a second material. Together the first material and the second material can be used to form the walls of a compartment 4 that is capable of containing or storing a non-liquid antiseptic composition.

A glove in accordance with the present invention contains or is capable of containing a non-liquid antiseptic composition in compartment 4. Not depicted in the figures is the feature that compartment 4 for some embodiments of the present invention can optionally be configured into any shape or size within reasonable limits of utility. Furthermore, compartment 4 may be subdivided into a plurality of compartments; each of these may be termed a subcompartment for the present invention. A variety of open, porous, partly closed, and/or closed additional partitions or walls within the compartment may be used to form the subcompartments. The non-liquid antiseptic composition is symbolized in all figures by stippling the area in the figure with dots. The non-liquid antiseptic composition comprises an antiseptic in a non-liquid composition. For some embodiments of the present invention, the antiseptic may be used in a solid form and may be the only ingredient comprising the non-liquid antiseptic composition. For example, a powder of sodium iodide or potassium permanganate might be used as a non-liquid antiseptic composition.

It is another object of the present invention to provide a flexible glove wall capable of providing a physical barrier means of protecting the hand while the glove is being worn by an individual. The glove can provide a useful physical barrier until a portion of the glove wall is punctured by an object. When a glove in accordance with the present invention is to be worn on the hand of a person such as a surgeon, a medical doctor, health care worker, or other worker, the glove wall needs to be flexible so that the the gloved hand can easily and adequately perform delicate, dexterous and complex work without causing the hand to become tired.

It is another object of the present invention to provide the method of using a flexible protective medical glove in accordance with the present invention wall on a hand of an individual to protect the hand in the event that an object that may be contaminated with an infectious agent punctures the glove, comprising the steps of:

(a) using the glove initially as a liquid-impermeable physical barrier to infectious pathogens; during which the glove can be used to permit the hand to perform a delicate, dexterous and complex type of work that includes the type of work performed by a surgeon, a medical doctor, a dentist, a laboratory worker, a hospital health care worker, a law enforcement worker, and a hospital worker; and during which the glove can be used to store a non-liquid antiseptic composition in the glove wall;

(b) using the glove to coat a portion of an object that may puncture the glove wall with the non-liquid antiseptic composition while the object punctures the compartment in the glove storing the non-liquid antiseptic composition;

(c) using the object puncturing the glove to transfer a portion of the non-liquid antiseptic composition coating the object from the glove to the hand and into the hand wound; and (d) using the non-liquid antiseptic composition that is transferred to the hand and into the hand wound to help to kill, inactivate, and to otherwise destroy any infectious pathogen transferred to the skin and into the hand wound by the glove-puncturing object.

It is another object of the present invention to provide a flexible protective medical glove that can be worn to protect an individual from an infectious pathogen; such a glove is particularily useful for a worker who ordinarily needs to wear a pair of standard medical or standard surgical gloves in order to protect their hands during their work. Gloves in accordance with the present invention can provide antiseptic chemical protection in addition to the barrier protection provided by conventional medical gloves. Thus, the present invention should be useful for medical personnel such as doctors, surgeons, dentists, laboratory workers, health care workers, and other hospital workers; the gloves should be particularily useful for medical personnel and other individuals who care for or may come into potentially infectious contact with AIDS infected or Hepatitis B infected patients.

Figure 2A:
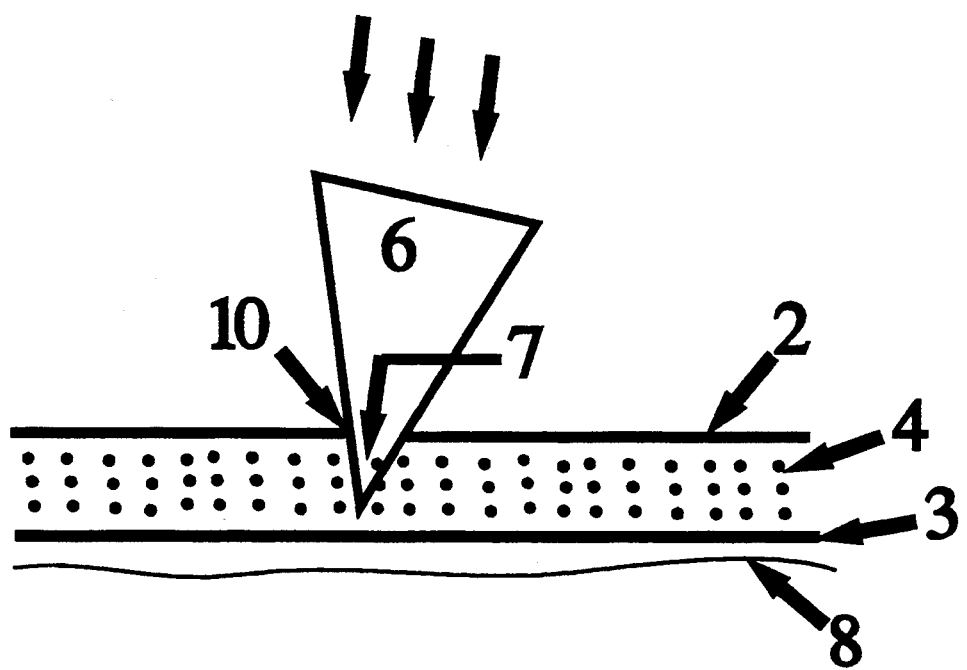
FIG. 2A is an enlarged sectional view of a glove wall taken along line 5—5 in FIG. 1A, illustrating one edge of an object which is puncturing a glove in accordance with the present invention; in this example, the object is puncturing the glove wall along line 5—5 and the non-liquid antiseptic composition in the glove wall is in the process of coating the object.
Figure 2B:
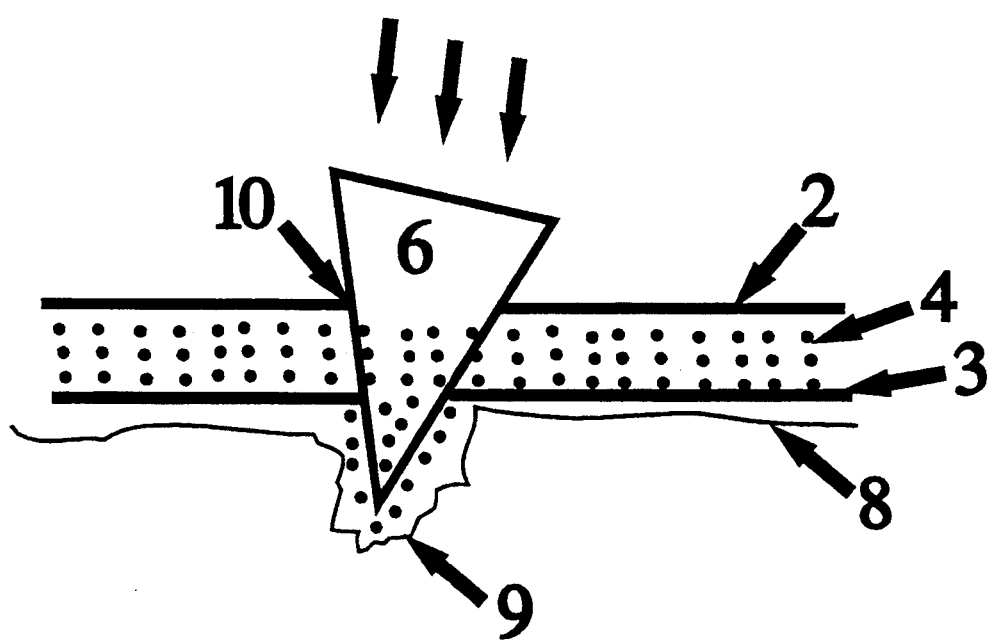
FIG. 2B illustrates the situation of FIG. 2A at a later point in time, after a portion of the glove-puncturing object has fully punctured the glove wall and has then wounded the hand; in the process the non-liquid antiseptic composition coating or smearing on the glove-puncturing object has been transferred to the hand and hand wound as an immediate automatic antiseptic treatment to the hand and to the hand wound.
Figure 2C:
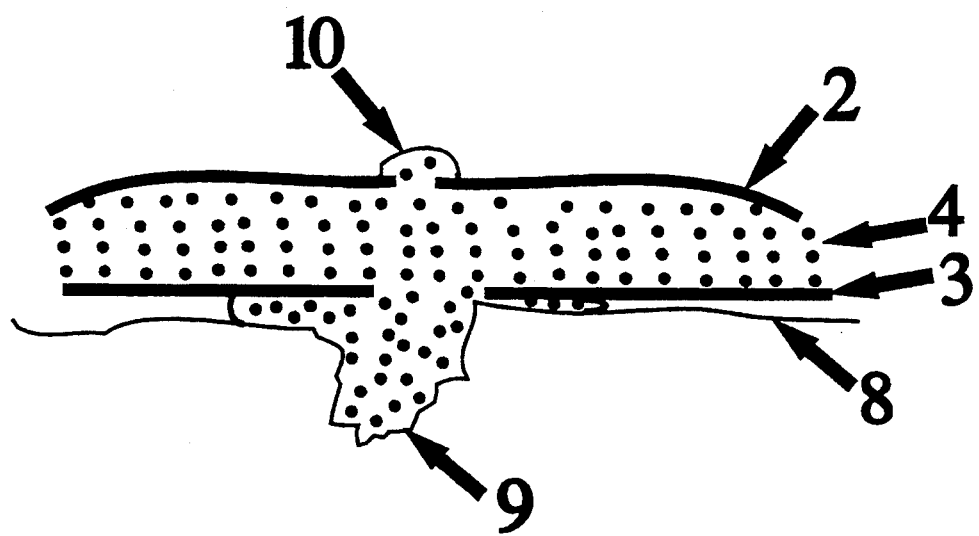
FIG. 2C illustrates the situation of FIG. 2B at a later point in time, following either the optional application of external manual pressure to the damaged glove or for some embodiments of the present invention after glove damage has occurred and initiated internal gas production by the non-liquid antiseptic composition and created an internal positive pressure within the compartment that can expand or expell some forms of the non-liquid antiseptic composition from the glove out of the hole caused by the glove-puncturing object; the result is both useful for increasing the amount of non-liquid antiseptic composition in the glove wall near the glove puncture hole, and is useful for extruding or expelling a suitable amount of non-liquid antiseptic composition from the glove wall through the glove wall puncture hole and onto the hand and into the hand wound.

FIG. 2A, FIG. 2B, and FIG. 2C illustrate the function of the present invention when an object causes a glove puncture while the glove is being worn on a hand. In most instances, a glove in accordance with the present invention is thin-walled like a standard medical examination glove or like a standard surgical glove. Thus, a glove wall of the present invention is capable of being punctured by an object when it contacts the glove wall with sufficient force. For the present invention, the definition of a glove-puncturing object is meant to include objects capable of puncturing, tearing, penetrating, cutting, abrading, shredding, chopping, biting, or otherwise disrupting the physical integrity of the glove wall. The wounding of a gloved hand is a common accident with health care workers. The glove puncturing object may be blunt or sharp edged. Typical objects that may cause an accidental glove puncture include the following objects: hypodermic syringe needles, suture needles, other needles, glass fragments, sharp metal fragments, scapel blades, mechanical devices, surgical instruments, medical instruments, blunt forceps, glass slides, glass capillary tubes, and accessory medical objects such drill tips, chisels, saws, wires and other glass objects. The edge of the glove-puncturing object depicted in FIG. 2A, FIG. 2B, and FIG. 2C is sharp. However, a sharp object is depicted here only for illustrative purposes and is not meant to be a limiting example. The glove puncturing object may be a blunt-edged object. For any glove-puncturing object, the interactions between glove-puncturing object 6, glove layer 2, glove layer 3, non-liquid antiseptic composition 4 and hand 8 as illustrated in the figures, are expected to be similar as will become readily apparent from the following detailed description of these interactions.

FIG. 2A illustrates a cross-section of a glove wall along Line 5—5 as shown in FIG. 1A. A glove-puncturing object 6 is shown puncturing a glove on a hand 8 at a glove wall puncture 10. Object 6 may be contaminated with an infectious pathogen. In addition, object 6 may be contaminated with blood, other body fluids, other solids and mixtures therof. The contamination of the glove-puncturing object 6 has not been depicted in these figures. The three arrows in FIG. 2A indicate the direction of motion for object 6. The contact angle of object 6 with the glove wall is not critical for function of the present invention.

It is another object of the present invention to provide a coating 7 of non-liquid antiseptic composition on the puncturing portion of object 6. When object 6 punctures outer glove layer 2 and contacts compartment 4 storing the non-liquid antiseptic composition, the contact may provide object 6 with a coating 7 of non-liquid antiseptic composition.

It is another object of the present invention to transfer a portion of coating 7 from object 6 for example, to the space between inner glove layer 3 and hand 8. In FIG. 2B, object 6 is puncturing inner glove layer 3 and thus has completely punctured the glove wall. If the non-liquid antiseptic composition is an essentially dry solid, a granular, a crystalline, a powder or the like dry composition, then coating 7 of non-liquid antiseptic composition on object 6 may deposit some of the dry composition in a small portion of the space between inner glove layer 3 and hand 8. Fluid matter on object 6 may cause the dry non-liquid antiseptic composition to adhere to some degree on object 6. If the non-liquid antiseptic composition contains in part some liquid and/or the antiseptic is solvated to some extent, as occurs with a number of non-liquid compositions such as foams, pastes, gels, ointments, greases, bases and the like compositions, then coating 7 is more likely to smear, stick, film or provide an even or more complete coating on the puncturing surfaces of object 6; preferable as a means for allowing a portion of the non-liquid antiseptic composition to be transferred on object 6 from compartment 4 to the space between inner glove layer 3 and hand 8.

It is another object of the present invention to have the capability to transfer a portion of coating 7 to hand wound 9, should a hand wound occur when the glove is punctured by object 8. Depending upon the depth of penetration of object 6 into hand 8, the hand wound 9 may have a shallow or a deep depth and variable bleeding. Prior to contacting the gloved hand, object 6 may have been contaminated; the contamination may include an infectious pathogen, blood, other body fluids, other solids and mixtures thereof. The infectious pathogens transferred from object 6 to hand 8 or hand wound 9 can cause a hand infection and/or a systemic infection in a human. As mentioned above, it is known that the risk of an infection in the gloved individual may be significantly lowered by immediately treating the potentially contaminated hand and the hand wound with an antiseptic. If object 6 contamination includes HIV virus or Hepatitis B virus, then contamination of hand 8 or hand wound 9 by object 6 can be very dangerous. Thus, a particularily important capability of a glove in accordance with present invention is to use the glove puncturing object 6 to transfer some of the non-liquid antiseptic composition from the glove to the hand and into hand wound as a preventative antiseptic treatment at the same time that object 6 may be contaminating the hand and a hand wound with an infectious pathogen. Providing an immediate treatment of non-liquid antiseptic composition to the hand and to the hand wound may be critical to help to prevent the establishment of a pathogenic systemic infection in individuals.

It is another object of the present invention as illustrated in FIG. 2C, to optionally enable the glove wearer or any other individual observing the gloved hand to more quickly see puncture site 10. To accomplish this objective, the non-liquid antiseptic composition may contain a colorant. The colorant may consist of one or more dyes and/or one or more opacifiers or any combination therein. Some examples of the colorants that may be used in the liquid antiseptic composition include but are not limited to one or a combination of the more than one of the following dyes: FD&C Yellow No. 5, FD&C Yellow No. 6, D&C Yellow No. 10, FD&C Red No. 40, FD&C Red No. 40, D&C Red No. 28, D&C Red No. 30, D&C Red No. 33, FD&C Blue No. 1, FD&C Blue No. 2., FD&C Green No. 3, D&C Green No. 5, yellow iron oxide, black iron oxide, red iron oxide brown iron oxide and mixtures thereof. Any suitable dye may be used. The colorant may be combined with one or more of the following opacifiers: white titanium dioxide, white calcium carbonate, white zinc sulfate, white zinc oxide, yellow iron oxide, black iron oxide red iron oxide brown iron oxide and mixtures thereof. Other acceptable opacifiers may be used.

Optionally, after a glove has been punctured by an object, another object of the present invention is to provide a smaller hole in outer glove layer 2 than in inner glove layer 3, after the glove-puncturing object has been removed from the glove wall at puncture 10. The relatively larger hole in inner glove layer 3 can help to promote a relatively larger transfer of non-liquid antiseptic composition from the glove to the hand and hand wound than from the glove to the outer surface of the glove wall. In other words, the difference in outer and inner glove layer puncture holes may be used to direct the non-liquid antiseptic composition toward the hand where it is needed to provide a treatment and may help reduce antiseptic contamination of the external surface of the glove. External antiseptic contamination of a doctor's gloves may be undesirable for example around medical patients or for a surgeon during internal surgery when the internal tissues of patient's body should not be exposed to an antiseptic.

Whether or not the glove-puncturing object is known to be contaminated with an infectious pathogen, it is another object of the present invention to provide a prophylactic treatment of non-liquid antiseptic composition to the hand and to the hand wound when a glove wall puncture 10 is caused by any object. The non-liquid antiseptic composition transferred to the hand and the hand wound can contact the hand and can dissolve or liquify in the hand wound. An immediate and nondelayed mixing of the antiseptic composition with any biological or infectious pathogen contamination that may be present in hand wound 9 may be useful for effective disinfection by inactivating, killing and/or otherwise destroying any infectious pathogen transferred to the hand wound. Thus, use of gloves in accordance with the present invention is envisioned as a particularily important preventative measure when there is any anticipated risk that the glove wearer could become exposed through the hands to HIV hepatitis B virus.

For some embodiments of the present invention the glove may be designed so that the non-liquid antiseptic composition in compartment 4 is capable of some redistribution. Providing the present invention with the capability for some redistribution of the non-liquid antiseptic composition may help meet the needs of the glove wearer following an accidental glove wall puncture. When the risk of infectious pathogen contamination to hand 8 and hand wound 9 has been perceived, then reflex glove massage by the gloved individual may be a particularily effective method of using a glove in accordance with the present invention to mobilize additional non-liquid antiseptic composition onto the hand and into the hand wound where it can be useful. Optionally, the glove wearer can massage (rub or apply constant pressure) to the glove wall near the puncture wound to force the non-liquid antiseptic composition in compartment 4 to accumulate near the glove wall having the hole (the hole in glove wall puncture 10). The thickness of compartment 4 in the glove wall in FIG. 2C is expanded compared to its thickness in FIG. 2B to illustrate the point that a local accumulation of the non-liquid antiseptic composition may occur in compartment 4 near glove wall puncture 10 as a result of glove massage. The local accumulation of non-liquid antiseptic composition in the glove wall can be further massaged or pressured by a hand or other means to force the non-liquid antiseptic composition in compartment 4 to become expelled, moved or extruded from the puncture hole in the glove, onto the hand and into the hand wound. This redistribution of the non-liquid antiseptic composition is only feasible when for example the non-liquid antiseptic composition is in a distensible or moldable state such as a foam, gel, paste, ointment, grease, putty, base and the like combinations of gas, liquid, and/or solids.

For some embodiments of the present invention, the non-liquid antiseptic compositions may be capable of providing a gas with antiseptic properties; examples of such antiseptic gases include but are not limited to the following gases: oxygen, chlorine, fluorine, bromine, iodine, chlorine dioxide, ozone, other halogen-oxygen compound gases, aldehyde gases, ethylene oxide, propylene oxide, propiolactone, sulfur, and the like and mixtures thereof. The antiseptic gas may be formed before, during or after the act of glove puncture by an object, or for example at the discretion of the glove wearer. The gas may be formed or provided by from the combination and/or chemical reaction and/or decomposition of a substance or substances(s) present in compartment 4 which may be singular or multicompartmental. Gas-producing substances may readily diffuse to the hand and hand wound treatment area through the glove puncture hole caused by the glove-puncturing object.

For some embodiments of the present invention, a dry solid antiseptic composition may be provided in compartment 4. Effective massage and/or redistribution of a dry solid antiseptic composition in compartment 4 may be difficult.

It is envisioned that for some embodiments of the present invention, a combination of substances in the glove or at the treatment area(s) may provide during the use of the present invention suitable antiseptic gases and/or non-liquid antiseptic compositions that are capable of being dispersed from the glove puncture. Dispersion may be accomplished by glove massage or other manually applied pressure or chemical generation of pressure and/or expanding antiseptic composition volume within compartment 4 may expell the non-liquid antiseptic composition from the glove wall puncture to the hand to inactivate or kill infectious pathogens that may be present on the hand or in the hand wound or other treatment areas. Treatment areas include but are not limited to the following: any surfaces of the glove puncturing object including the inner barrel of the syringe needle, any surfaces of the glove and/or its compartment(s), and any portions of the hand(s) and/or any hand wounds that may be present or may form while a glove in accordance with the present invention is being worn by an individual.

To make a glove in accordance with the present invention which has an outer glove layer and an inner glove layer of similar elasticity and similar plasticity, similar materials forming these glove layers may be used and may comprise: (a) a structural material selected from the group consisting of latex rubber, cis-1,4-polyisoprene, cis-polybutadiene, neoprene rubber, nitrile rubber, silicone rubber, polychloroprene rubber, another halogenated rubber, a case-hardened rubber, another butadiene rubber, a cross-linked rubber, isobutylene-isoprene 1. butyl rubber, butadiene-acrylonitrile 1. nitrile rubber, styrene-butadiene rubber, ethylene-propylene copolymer, ethylene-propylene diene terpolymer, polyisobutylene, chlorosulphonated polyeten, ester-type urethan rubber, polychlormethyloxyran epichlorhydrin rubber, epichlorhydrin copolymer with ethyleneoxydichlormethyloxyran copolymer, another suitable rubber, cellulose acetate plastic, vinyl plastic, polyethylene plastic, polypropylene plastic, polyvinyl chloride plastic, polyvinyl acetate plastic, polystyrene plastic, polymethyl methyl-acrylate plastic, polyacrylonitrile plastic, vinyllite plastic, saran plastic, polytetrafluoroethylene plastic, polytrifluoro-chloroethylene plastic, polycaprolactam plastic, polyester plastic, urea formaldehyde plastic, polyurethane plastic, isotactic polypropylene plastic, nylon plastic, rayon plastic, polyamide plastic, phenolic plastic, silicone plastic, another suitable plastic, silk fiber, suitable fiber from an animal secretion, cotton fiber, cellulose fiber, another suitable plant fiber, wool fiber, another suitable animal fiber, animal hair, animal skin, animal intestinal tissue, animal connective tissue, another suitable animal tissue, metal fiber, mineral fiber, another suitable synthetic fiber, and mixtures thereof; and (b) optionally a colorant selected from the group consisting of titanium oxide, an iron oxide, a dye and mixtures thereof. If structural materials are used that can form liquid permeable layers, then the wall structure may be coated or embedded with a liquid-impermeable material to make the glove structure layer liquid-impermeable.

Alternatively, to make a glove in accordance with the present invention having an inner glove layer of lower elasticity and higher plasticity than the outer glove layer, the first material (which is used for the outer glove layer) may comprise an elastic structural material selected from the group consisting of latex rubber, cis-1,4-polyisoprene rubber, cis-polybutadiene rubber, neoprene rubber, nitrile rubber, silicone rubber, polychloroprene rubber, another halogenated rubber, a case-hardened rubber, another butadiene rubber, a cross-linked rubber, isobutylene-isoprene 1. butyl rubber, butadieneacrylonitrile 1. nitrile rubber, styrene butadiene rubber, ethylene-propylene copolymer, ethylene-propylene diene terpolymer, polyisobutylene, chlorosulphonated polyeten, ester-type urethan rubber, Polychlormethyloxyran epichlorhydrin rubber, epichlorhydrin copolymer with ethyleneoxydichlormethyloxyran copolymer, another suitable rubber and mixtures thereof; and optionally a colorant selected from the group consisting of titanium oxide, an iron oxide, a dye and mixtures thereof. The second material (used for the inner glove layer) may comprise: a plastic structural material selected from the group consisting of cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polycaprolactam plastic, polytrifluorochloroethylene plastic, nylon plastic, rayon plastic, polyester plastic, urea formaldehyde plastic, polyurethane plastic, isotactic polypropylene plastic, polyamide plastic, phenolic plastic, silicone plastic, another suitable plastic, silk fiber, another suitable fiber from an animal secretion, cotton fiber, another suitable plant fiber, wool fiber, another suitable animal fiber, animal hair, animal skin, animal intestinal and connective tissues, metallic fiber, mineral fiber, chemically-modified natural fibers, chemical-modified synthetic fibers another synthetic fiber, and mixtures thereof; and a colorant selected from the group consisting of titanium oxide, an iron oxide, a dye and mixtures thereof. Materials obtained from animal intestinal tissues and animal connective tissue may comprise the intestinal wall, ligaments, tendons and fascia and like tissue obtained from slaughtered farm or ranch animals including the following animals: cow, bull, sheep, steer, horse, chicken, goat, mink, rabbit, and pig. It is imagined that almost any animal may provide suitable raw materials for the glove.

Optionally the colorants may be homogeneously mixed with the glove wall structural materials to color the materials and/or to opacify the materials. Alternatively, optionally one or more colorants or opacifiers and mixtures thereof may be printed onto the glove wall or may color the wall with a design or pattern or cartoon figure that renders the glove wall opaque or colored in a more pleasing or useful decoration. The design or pattern may have an appealing look or look non-threatening to help the patient of the glove wearer, or glove wearer feel less anxious, less frightened, and amused or calmed; this optional visual effect of the present invention is particularily useful for calming children and nervous or frightened patients of a gloved medical doctor or other health care worker. Such coloration may also be useful in general when gloves are worn by other individuals who may come into contact with other individuals, or who may be engaged in distasteful work activities requiring glove wear. The design on the gloves may in addition have a positive impact on the glove wearer or provide written instructions or reminders to a gloved worker of a procedure for example. Glove coloration or opacity can also be used to make a glove in accordance with the present invention have the coloration appearance of a conventional medical glove. For example, the coloration and/or opacification of the glove wall can be used to obscure the presence of the non-liquid antiseptic composition contained within a thin-walled glove of the present invention.

A glove in accordance with the present invention can contain a non-liquid antiseptic composition, or is suitably capable of providing an antiseptic in a non-liquid composition as the glove is punctured by an object. The then-formed non-liquid antiseptic composition is not capable of flowing like a liquid from compartment 4 from the glove puncture hole. However, the contact between the non-liquid antiseptic composition and (1) a hand, (2) a glove-puncturing object, and/or (3) an artificial or biological substance in or from the hand wound may cause an alteration(s) in the non-liquid state of the non-liquid antiseptic composition. After contact, the non-liquid antiseptic composition may become capable of liquifying or softening to the extent that the composition or the new mixture following contact which includes the non-liquid antiseptic composition might then have the capability to flow like a liquid or the non-liquid antiseptic composition may dissolve in blood or other biological liquid. The dissolution may be useful for improving contact between the antiseptic and infectious pathogens.

The non-liquid antiseptic composition comprises one or more antiseptics in a non-liquid composition. As mentioned previously, the non-liquid antiseptic composition may contain one or several liquid substances as components in the composition. The liquid(s) provided in the composition may have a number of functions for some embodiments of the present invention including an antiseptic function, or a solvent or a dispersant function useful during preparation of the non-liquid antiseptic composition or during use of the present invention. Low molecular weight liquids are particularily useful during the formation of the composition to help to solvate and to properly disperse/mix the colloids and polymers added to form the non-liquid antiseptic composition.

For the present invention, the non-liquid antiseptic composition may take on one or more of the following forms during the use of the present invention: a foam, a gel, a paste, a magma, an ointment, a gas, a solid, a microscopic dust, a powder, as crystalline powder, an aerosol, a non-liquid emulsion, a multiple phase emulsion, a base including the following conventional dermatological bases (an oleaginous ointment base, an absorption ointment base, an emulsion ointment base, and a water-soluble ointment base), a grease, a putty, a non-flowable cream, and the like other soft, deformable gas/liquid/solid combination formulations.

The non-liquid antiseptic composition has the property that its final non-liquid state, during or as a result of a glove puncture within a glove in accordance with the present invention, is incapable of flow like a liquid. (See Remingtons Pharmaceutical Sciences: 1965—pages 456-457 and 525-556).

Oleaginous base ointments may include the following: (1) fats and fixed oil bases such as benzoinated lard optionally stiffened with beeswax or synthetic cetyl esters wax (also known as carats bases); (2) optionally hydrocarbon bases such as petroleum Jelly or petrolatum NF of any color (i.e., bleached white or yellowed) stiffened with wax or other known stiffening agents, mineral oil stiffened with heavy hydrocarbon waxes (i.e, waxes of about 1300 molecular weight is sold by E.R.Squibb & Co. as Plastibase or Jelene); or (3) optionally silicones such as for example Dow Corning 200 stiffened with wax or other stiffening agents.

Absorption bases are hydrophilic and may be comprised of lanolin and petrolatum and/or animal sterols (for example cholesterol, oxycholesterol and/or other suitable wool fat fractions) and petrolatum. The stiffness and thermal stability of an absorption base can be increased by the inclusion of waxes, stearyl alcohol and like substances. Wool alcohols can be prepared by treating wool fat with alkali and separating the fraction containing cholesterol and other alcohols. A base made with wool alcohol and wax easily absorbs water and this hydrophilicity may enhance the antiseptic activity of antiseptic(s) used in absorption bases. The addition of water to an absorption base may improve the bases's emolliency (softness).

Emulsion bases are solid emulsions to which it is possible to incorporate additional water. Optionally, the emulsion base may contain wetting agents, dispersing agents, emulsifiers, penetrants, emollients, humectants, detergents, hardeners, preservatives and the like to modify the properties of the base. Surface active agents may, for example, be ionic (cationic or anionic compounds, for example soaps), zwitterionic, polyionic, or nonionic surface active agents which contain hydroxy groups and ether linkages (polyhydric alcohol anhydrides and polyoxyethylene chains) to provide hydrophillic activity. For example, polyoxyethylene glycol 400 (PEG 400), a Tween, Span 40, Polysorbate 80, polyoxyl 40 stearate, and the like are frequently used examples of nonionic surface active agents. Water soluble ointment bases may comprise an aqueous phase of 10 to 80 percent, an emulsifying agent, and an oleaginous phase of 20 to 90 percent. A humectant, for example, glycerin, propylene glycol, or a polyethylene glycol may be added to the aqueous phase to stabilize the water content of the ointment base. The humectant can also improve the dispersion of the non-liquid antiseptic composition when it comes into contact with aqueous media on the hand and in the hand wound (such as for example sweat, serum, and blood) should a wound occur. The addition of certain alcohols, for example stearyl alcohol, cetyl alcohol, fatty acid esters of sorbitan or mannitan, alkyl alcohols ($C_{20}$-$C_{30}$) can be added to emulsion base formulas to help to stabilize the aqueous content of the emulsion. Stearyl alcohol is a solid that also contributes to the hardness of the ointment base. The oleaginous phase (also known as the non-aqueous phase) may comprise a petrolatum, fats, waxes, organic alcohols, polyglycol esters, and the like water-insoluble molecules. The emulsifier for an oil-in-water emulsion may be an alkali soap, alkyl sulfate, amine soap, polyglycol ester, alkyl aryl sulfate, quaternary ammonium compound and the like. One suitable method of preparation of an ointment base is to separately heat (for example with use of a steam bath) the aqueous phase(s) with its additives and the non-aqueous phase(s) until each phase is in a suitably softened, melted or liquid state, and until each phase has attained approximately the same temperature. The heating may be used to attain a temperature of between about 25 and 200 ° C., preferably between about 45 and about 95 degrees centigrade. Preferably the aqueous and non-aqueous phases may be then mixed at about the same temperature, until a smooth creamy mixture is obtained. Stirring may be continued while the mixture cools as desired before it is added to a glove.

Optionally, some non-liquid antiseptic compositions may not contain a liquid component. These non-liquid antiseptic compositions may comprise a mixture of non-liquid antiseptics and additives. For example, the composition may appear for example as a dry powder or as a paste. Pastes tend to be stiffer, less greasy and more liquid absorptive than ointments. Pastes may contain starch, a pectin, zinc oxide, calcium carbonate, and/or talc in the base and are useful as a means for absorbing secretions and their contaminants from acute wounds.

For the present invention, the non-liquid antiseptic composition should ideally have the following six properties: (1) does not retard wound healing; (2) has a low sensitization index; (3) has a low index of irritation; (4) has good storage stability; (5) has a minimum number of ingredients; and (6) is easy to compound or make. However, to some extent most antiseptic compositions do interfere with cell wound healing, do sensitize the skin and do irritate the skin. It follows then that the design of a glove that can provide a non-liquid antiseptic composition and that can comply with the above six criteria may either not be possible or may not be suitable if the glove then can not function adequately to help to rapidly kill infectious pathogens such as HIV or hepatitis B virus on contact. Thus, some side effects of the present invention may need to be tolerated by the glove wearer in order to lower their risk of squiring a dangerous possibly lethal infection such as HIV or hepatitis B virus from a glove puncture by an object contaminated with HIV or hepatitis B virus.

For the present invention, the term antiseptic is meant to include but not be limited to the following: antimicrobial agents, antibiotics, chemotherapeutic agents, any antiseptics, antiviral agents, viricidal agents, bacteriocidal agents, antifungal agents, antiparasitic agents, and the like. The words antiseptic, disinfectant, and germicide all connote an agent which can kill microbes or infectious pathogens upon contact and thousands of chemical compounds are known which have antiseptic properties (For some examples see Remingtons Pharmaceutical Sciences: 1985, 1990 and Harvey, 1985).

The antiseptic used in some embodiments of the present invention may be selected from the group consisting of chlorhexidine gluconate, chlorhexidine acetate, chlorhexidine hydrochloride, chlorhexidine, other chlorhexidine salts, other hexamethylenebis biguanides, octoxynol, nonoxynol-9, methanol, ethanol, isopropanol, allyl alcohol, rubbing alcohol NF, sodium hypochlorite, potassium hypochlorite, calcium hypochlorite, magnesium hypochlorite, sodium dichloroisocyanurate, sodium perborate NF, sodium hydroxide, potassium hydroxide, magnesium hydroxide, calcium hydroxide, ammonia, ammonium hydroxide, lithium hydroxide, barium hydroxide, silver hydroxide, other metal hydroxides, sodium tetradecyl sulfate, sulfur dioxide, pentationic acid, colloidal sulfur, sulfurated potash, sublimed tyrothricin, hexachlorophene, hypochlorous acid, other chlorophors, acetic acid, hydrochloric acid, sulfuric acid, sodium acetate, aluminum acetate, acetarsone, aluminum subacetate, cadmium sulfide, selenium sulfide, other metal sulfides, bacitracin, calomel, chiniofon, creosote, diiodohydroxyquin, eucalyptol, eucalyptus oil, glycobiarsol, gramicidin, hexyl resorcinol, methylene blue, peppermint oil, phenylethyl alcohol, phenyl salicylate, methyl salicylate, pine tar, pine oil NF, pine oil emulsion, tertiary terpene alcohols, secondary terpene alcohols, alpha-terpineol, borneol, fenchyl alchol, o-methylchavicol, polymixin B sulfate, colistin, chloramphenicol, tetracycline, erythromycin, gentamycin, mafenide acetate, neomycin sulfate, sulfisoxazole diolamine, sulfacetamide sodium, gentamycin sulfate, amphotericin B, tobramycin, a penicillin, a cephalosporin, salicylic acid, trichloroacetic acid, benzoic acid, pyrogallol NF X, pyrogallic acid, sodium benzoate, boric acid, sodium borate, lactic acid, sodium lactate, chloramine, chloramine T, silver nitrate, ammoniacal silver nitrate solution, eugenol, elemental iodine, sodium iodide, potassium iodide, calcium iodide, ammonium iodide, silver iodide, colloidal silver iodide in gelatin, silver lactate, ferrous iodide, mercuric iodide red, mercuric oxide red, strontium iodide, lithium iodide, magnesium iodide, zinc iodide, silver iodide, selenium iodide, thymol iodide NF X, dithymol diiodide, iodinated derivatives of thymol, other iodide salts, povidone-iodine, iodoform, iodinated organic compounds, iodol, iodopyrrol, other iodophors, chlorinated lime, bromide salts, sodium bromide, merbromin NF, other bromophors, other brominated chemicals, sodium fluoride and other fluorinated chemicals and fluorophors, Lysol, Nonidet P40, phenyl mercuric acetate, potassium mercuric iodide, proflavine hemisulfate, 3,6-diaminoacridine bisulfate, formaldehyde, glutaraldehyde, parsformaldehyde, butyl hydroxybenzoate, mercurous chloride, iodochlorhydroxyquin, zinc nitrate, zinc sulfate, cadmium sulfate, thimerosal NF, zinc oxide, zinc acetate, zinc chloride, silver nitrate, silver sulfadiazine, hydrogen peroxide, urea hydrogen peroxide, hydrogen peroxide carbamide, benzoyl peroxide, calcium peroxide, magnesium peroxide, barium peroxide, strontium peroxide, sodium peroxide, potassium perchlorite, sodium perchlorite, calcium perchlorite, magnesium perchlorite, zinc perchlorite, zinc peroxide, zinc carbonate, zinc hydroxide, zinc sulfate, succinyl peroxide, succinchlorimide NF IX, N-Chloro-succinimide, potassium permaganate, sodium chlorate, potassium chlorate, phenol, sodium phenolate, domiphen bromide, salicylic acid, bismuth-formic-iodide, bismuth subgallate, bacitracin zinc, sodium lauryl sulfate, carbamide peroxide, sodium borate, oleic acid-iodine, piperonyl butoxide, sodium peroxyborate monohydrate, ammonium ichthosulfonate, eucalyptol, menthol, Witch Hazel, camphor, tannic acid, camphorated phenol, phenol glycerin, chloroxylenol, 4-chloro-3,5-xylenol, chloroquinaldol, nalidixic acid, zinc phenol-sulfonate, zinc sulfocarbolate, hydroxynalidixic acid, pipemidic acid, norfloxacin, norfloxacin hydrochloride, other quinolones, 8-hydroxyquinoline sulfate, sodium phenolate, thyme oil, o-cresol, m-cresol, metacresylacetate, p-cresol, cresol NF, 4-chloro-m-cresol, 4-chloro-S,5-xylenol, saponified cresol solution NF, methylphenol, ethyl phenol, other alkyl phenols, o-phenyl phenol, other aryl phenols, bis-phenols, phenyl-mecuric chloride, phenylmecuric borate, resorcinol, resorcinol monoactetate NF, orthophenylphenol, chloroxylenol, hexyl-resorcinol, parachlorophenol, paratertiary-amylphenol, thymol, chlorothymol NF, menthol, butylparaban, ethylparaben, methylparaben, propylparaben, triclosan, bithionol NF, o-benzyl-p-chlorophenol, hexachlorophene, poloxamer 188, benzalkonium chloride where the alkyl groups attached to the nitrogen represent any alkyl from $CH_3$ to $C_{18}H_{37}$, methylbenzethonium chloride, cetrimonium bromide, abikoviromycin, acetylenedicarboxamide, acetyl sulfamethoxypyrazine, triclobisonium chloride, undecoylium chlorideiodine, coal tar solution, furazolidone, nifuroxime, nitrofurazone NF, nitromersol NF, oxychlorosene, sodium oxychlorosene, parachlorophenol NF, camphorated parachlorophenol NF, phenylmercuric nitrate NF, gentian violet USP, hexamethyl-para-rosaniline chloride, rosaniline chloride, pentamethylpararosaniline chloride, methylrosaniline chloride, tetramethylpararosaniline chloride, nonylphenoxypolyethoxyethanol, methoxypolyoxyetheneglycol 550 laurate, oxyquinoline benzoate, p-triisopropylphenoxypolyethoxy-ethanol, halazone NF, dichloramine-T, benzethonium chloride, econazole, cetylpyridinium chloride, methylbenzethonium chloride, cetyldimethylbenzylammonium chloride, dichlorobenzalkonium chloride, domiphen bromide, triclocarban, clotrimazole, ciclopirox olamine, undecylenic acid, miconazole, tolnaftate, acriflavine, euflavine, 3,6-diamino-10-methylacridium chloride, 3,6-diamino-acridine, acid acriflavine, 5-aminoacridine hydrochloride monohydrate, malachite green G, dodecyltrimethylammonium bromide, tetradecyltrimethylammonium bromide, dequalinium chloride BP, dibromopropamidine isethionite, hexadecyltrimethylammmonium bromide, chloroazodin NF X, N-chloro-p-toluenesulfonamidosodium, 4-[(dichloroamino)sulfonyl]-benzoic acid, methenamine, methenamine mandelate, methenamine hippurate, octoxynol 9, phenazopyridine hydrochloride, 9-aminoacridine hydrochloride, bismuth tribromophenate, p-tert-butylphenol, cetyldimethylethylammonium bromide, chlorothymol, cloflucaban, clorophene, cloroxine, 8-hydroxyquinoline, merbromin, mercuric oxide yellow, ammoniated mercury, p-tert-pentylphenol, phenylmercuric acetate, phenylmercuric nitrate, propylene oxide, zinc pyrithione, zinc bacitracin, chlortetracycline hydrochloride, calcium chlortetracycline, oxytetracycline hydrochloride, beta-propiolactone, acyclovir, acyclovir sodium, amantadine hydrochloride, cytarabine, idoxuridine, interferon, gamma interferon, ribaviron, rifampin, suramin, trifluridine, vidarabine, zidovudine, methisazone, tumor necrosis factor, ampligen, ansamycin, (E)-5-(2-bromovinyl-2'-deoxyuridine, butylated hydroxytoluene, castamospermine, dextran sulfate, dideoxycytidine, dideoxyadenosine, dideoxyinosine, Peptide-T, dihydromethylpyridinylcarbonyloxyazidodideoxythymidine, ganciclovir, 2'-fluoro-2'-deoxy-5-iodo-ara C, phosphonoformate, rimantadine hydrochloride and the like and their derivatives and mixtures thereof. For optimal antiseptic activity, nonoxynol-9 is bufferred to a pH between about 5.0 and about 4.0; preferably the pH may be about 4.5 in a non-liquid antiseptic composition containing nonoxynol-9.

The non-liquid antiseptic composition may be designed to be capable of specifically killing, inactivating and/or otherwise destroying a particular infectious pathogen. Alternatively, the non-liquid antiseptic composition may be designed to have a broad spectrum antiseptic activity against infectious pathogens. Preferably, a glove in accordance with the present invention contains an antiseptic formulation capable of at least inactivating or killing HIV or Hepatitis B virus. Preferably the antiseptic used in the glove is selected from the group consisting of povidone-iodine, elemental iodine, sodium iodide, potassium iodide, sodium hypochlorite, nonoxynol-9, and chlorhexidine gluconate and mixtures; antiseptics of known effective viricidal and antiviral activity.

The inclusion of a metal ion chelator such as EDTA, EGTA, NTA, HEDTA or other ion chelator at a concentration of between about 5 micromolar to about 5000 micromolar, in the non-liquid antiseptic composition may be useful to help preserve the activity of the antiseptic by chelating ions (cations or anions) which may chemically inactivate the antiseptic. Other preservatives which may be added to the non-liquid antiseptic composition include a pH buffer to stabilize the pH, such as for example a pH buffer of ascorbic acid and ascorbate salts, a phosphate buffer, an amino acid buffer, a GOOD Buffer, sulfate buffers, a zwitterionic pH buffer, other pH buffer systems; free radical scavengers, metal ion chelators and reducing agents such as dithiothreitol (DTT) may also be useful. Antiseptics whose activity is stabilized by a metal ion chelator or pH buffer include at least the following antiseptics: hydrogen peroxide, benzoyl peroxide, other peroxide antiseptics, sodium hypochlorite, potassium hypochlorite, sodium dichloroisocyanurate, hypochlorous acid, iodine, sodium iodide, potassium iodide and other halogen-releasing antiseptics. The term halogen is meant to include any of the halogens: fluorine, chlorine, iodine, and bromine in any of their their elemental states, isomorphic forms, or reduced forms.

For the present invention the term non-liquid antiseptic composition is meant to include the following non-liquid physical states for the antiseptic composition: powdered solids of any powder grain size, foam, non-liquid cream, gel, jelly, paste, cerate, ointment, emulsion base, plaster, putty, glycerogelatin, and any other non-liquid states forms that may be suitably used in the present invention (See Remington's Pharmaceutical Sciences, 1965: Chapter 37—pages 525-556, and pages 455-459. In any of these physical states the non-liquid antiseptic composition may comprise a mixture(s) of liquids and solids and for some embodiments of the present invention, may also include a gaseous component.

Gas producing substances in suitable liquids or in non-liquid compositions may be used to produce a quantity of gas, the gas comprising in some embodiments of the present invention: (a) a gas useful for producing an expanding foam-state antiseptic composition; (b) a gas useful for increasing the gas pressure in the glove wall as a means for forcibly expelling the non-liquid antiseptic composition from the glove wall puncture; or (c) an antiseptic with the rapid diffusion rates inherent to gases. Gas-producing substances include the following chemical combinations: (1) the combination of a bicarbonate or carbonate compound with an acid to form carbon dioxide gas; (2) the combination of a peroxide or a perchlorite compound with a chemical catalyst such as for example, manganese dioxide to form oxygen gas; and (3) the combination of a halogen or halogenated compounds with an acid or oxidizing agent to form a halogen gas.

The bicarbonate compound may be selected from the group consisting of the following: sodium bicarbonate, potassium bicarbonate, calcium bicarbonate, magnesium bicarbonate, zinc bicarbonate, ammonium carbonate, tetramethylammonium bicarbonate, choline bicarbonate, tetraethylammonium bicarbonate, propylene carbonate, butylene carbonate, other alkyl ammonium bicarbonates, benzalkonium bicarbonate, alkylpyridinium bicarbonate, tetraphenylammonium bicarbonate and mixtures thereof. The carbonate compounds corresponding to the above mentioned bicarbonates may be substituted provided that additional acid is provided for the reaction with the carbonate. Bicarbonate and carbonate compounds release carbon dioxide gas when reacted with mineral or organic acids.

The peroxide compounds may be selected from the group consisting of the following: hydrogen peroxide, urea hydrogen peroxide, benzoyl peroxide, succinyl peroxide, barium peroxide, calcium peroxide, magnesium peroxide, sodium peroxide, strontium peroxide, zinc peroxide, other peroxide compounds and mixtures thereof. When exposed to fine metal powders or metal oxide catalysts such as manganese dioxide, the peroxides in aqueous solutions buffered at neutral pH or alkaline pH generally can release oxygen gas or can form hydrogen peroxide which subsequently releases oxygen gas. Urea hydrogen peroxide can decompose into oxygen gas and urea when exposed to an alcohol or an ether.

Halogens and halogenated compounds are capable of reacting in aqueous or aqueous/alcoholic solutions with an acid to release potent antiseptics in soluble and gaseous forms. The useful halogens include fluorine, chlorine, bromine and iodine. In general, a halogenated or halogen antiseptic can raise the halogen concentration in the mileau of a sample of infections pathogen to several parts per million (ppm) of halogen. The potent and potentially rapid antiseptic activity of a halogen against a virus, a bacteria or other infectious pathogens is generally held to be due to the high chemical reactivity of the halogen against the proteins of the infectious pathogen essential for its viability and reproduction.

A chlorine containing antiseptic compound such as sodium hypochlorite can react with a liquid acid such as an aqueous solution of hydrochloric acid to produce a mixture of hypochlorous acid, chlorine dioxide, and chlorine gas which as a combination form a rapid-acting, potent antiseptic mixture. A solution of 0.1–5 percent elemetal iodine, 0.1 to 10 percent iodide salt in an aqueous solutions containing 25 to 95 percent of a suitable alcohol becomes a more potent antiseptic when acidified to below pH 7, even more potent below pH 6.5. From the reaction of water with $I_2$ (elemental iodine) and iodide ion at pH 6.5 or lower pH, the reactive iodide compounds, HOI (hypoiodous acid) and HI (iodic acid) are formed in sufficient concentration as to provide rapid and potent antiseptic activity. In addition, iodide anion ($I^-$) can react with $I_2$ to form $I_3^-$, a soluble complex form of iodine that is useful as a reservoir of $I_2$ in solution.

The non-liquid antiseptic composition may contain a liquid selected from the group consisting of water, methanol, ethanol, isopropanol, propanol, allyl alcohol, butanol, isobutanol, sec-butanol, tert-butanol, benzyl alcohol, nonxynol-9, n-octyl alcohol, 2-octyl dodecanol, other liquid alcohols, glycerol, propylene glycol, other liquid glycols, 1,2,6-hexanetriol, other liquid triols, polyethylene glycol of between about 150 to about 700 molecular weight, other liquid polyethylene glycols, other liquid glycols, other liquid triols, urea, other liquid amides, acetone, methyl ethyl ketone, ethyl ketone, methyl isopropyl ketone, 2-pentanone, ethyl acetate, ethyl propionate, ethyl butyrate, ethyl valerate, methyl acetate, propyl acetate, isopropyl acetate, butyl acetate, sec-butyl acetate, tert-butyl acetate, amyl acetate, pentyl acetate, isopentyl acetate, benzyl acetate, 2-methoxyethanol, 2-methoxyethyl acetate, 2-ethoxyethanol, 2-ethoxyethyl acetate, other liquid ketones except methyl n-butyl ketone, other liquid esters, other liquid aldehydes, formic acid, other liquid organic acids including liquid carboxylic acids, mineral oil, silicone oil, other chemically derived oils, hexamethyl disiloxane, other liquid silanes, glycerol trioctanoate, decyl oleate, cetearyl isononanoate, other liquid soaps, other liquid detergents, dimethicone, other liquid silicones, perfluropolymethylisopropyl ether of about 1500 to about 6600 molecular weight, other liquid emulsifiers, olive oil, cottonseed oil, corn oil, soybean oil, wheat germ oil, linseed oil, pine oil, almond oil, macadamia oil, coconut oil, jojoba oil, peanut oil, persia oil, castor oil, other vegetable oils, other plant oils, cod liver oil, shark liver oil, mink oil, other animal oils, squalene, other liquid steroids, other suitable relatively non-toxic naturally occurring liquids, other suitable man-made liquids, and the like and mixtures thereof.

Suitable materials, suitable liquids and other suitable chemicals which may be used in the present invention are considered "suitable" for the present invention when these substances (1) can provide to some degree of suitable function for the present invention at some concentration and (2) at the concentration used, cause tolerable side-effects and tolerable toxicity to the human body as measured against the protective benefits of the present invention. For example, some of the more powerful non-liquid antiseptic compositions in the present invention may help to protect a gloved individual from acquiring a systemic HIV infection after a becoming injured on a hand by an HIV and blood-tainted needle. The process of using the present invention to protect the individual may temporarily impair the healing process in the needlestick wound because of the effects of the antiseptic composition. However, while the present invention may impair wound healing, this negative effect is minor and quite tolerable in view of the capability of the present invention to help to prevent a serious infection from occurring to a gloved individual after a glove wall puncture.

It may be useful to include at least one surface active agent in the non-liquid antiseptic composition to facilitate the coating of the glove-puncturing object with the non-liquid antiseptic composition. The surface active agent may be selected from the group consisting of dodecyldimethylamine oxide, lauryldimethylamine oxide, other similar oxides, stearic acid, dibutyl adipate, octyl stearate, octyl alcohol, sodium cetearyl stearate, isopropyl myristrate, palmitic acid, other fatty acids, stearyl alcohol, colloidal magnesium aluminum silicate, colloidal silicon dioxide, other mineral colloids, caprylic triglyceride, capric triglyceride, decyl-beta-D-glucopyranoside, cetostearyl alcohol, nonyl-beta-D-glucopyranoside, octyl-beta-D-glucopyranoside, magnesium stearate, calcium stearate, potassium stearate, aluminum stearate, zinc stearate, triethanolamine stearate, other stearates, sodium lauryl sulfate, heptyl-beta-D-glucopyranoside, hexyl-beta-D-glucopyranoside, dodecyl-beta-D-maltoside, decyl-beta-D-maltoside, sodium dodecylsulfate, sodium oleate, potassium laurate, sodium laurate, sodium lauryl sulfate, glycerol monostearate, propylene glycol monostearate, other fatty acid esters, bis(2-ethylhexyl)sodium sulfosuccinate, propylene glycol monolaurate, N-dodecyl-sulfatobetaine, octyl-beta-D-thiogluco-pyranoside, heptyl-beta-D-thioglucopyranoside, N-dodecyl-N,N-dimethyl-glycine, cetyl alcohol, N-decylsulfatobetaine, digitonin, 1,2,6-heaxanetriol, N-hexyadecylsulfatobetaine, N-tetradecylsulfatobetaine, dioctyl sodium sulfosuccinate, N,N,bis(3-D-gluconamidopropyl)-cholamide, sodium deoxycholate, N,N,bis(3-D-gluconamidopropyl)-deoxycholamide, glycerol monostearate, N-octylsulfobetaine, sodium taurodeoxycholate, sodium cholate, sodium taurocholate, sodium glycocholate, other steroids, cetyltrimethylammonium bromide, 3-[(3-cholamidopropyl)dimethyl ammonio]-1-propanesulfonate, 3-[(3-cholamidopropyl)dimethylammonio]-2- hydroxypropane-1-sulfonate, octanoyl-N-methylglucamide, nonanoyl-N-methylglucamide, decanoyl-N-methylglucamide, nonyl-N-methylglucamide, lecithin, lysolecithin, nonaethylene glycol monododecyl ether, nonaethylene glycol octylphenol ether, nonaethylene glycol octylcyclohexyl ether, heptaethylene glycol octylphenyl ether, heptaethylene glycol octylcyclohexyl ether, polyoxyethylene (10) monolauryl ether, polyoxyethylene (8) isotridecyl ether, polyoxyethylene (10) isotridecyl ether, polyoxyethylene (15) isotridecyl ether, polyoxyethylene (9) lauryl ether, polyoxyethylene (23) lauryl ether, octaethylene glycol monododecyl ether, nonaethylene glycol monododecyl ether, other ethers, polyethylene polypropylene glycol, sorbitan monopalmitate, sorbitan monooleate, sorbitan monostearate, polyoxyethylene sorbitan monolaurate, polyoxyethylene sorbitan monooleate, other sorbitans, polyoxyethylene-4-lauryl ether, polyethylene glycol 400 monostearate, polyoxyethylene-4-sorbitan monolaurate, Polyoxyethylene-20-sorbitan monooleate, polyoxyethylene-20-sorbitan monopalmitate, polyoxyethylene-20-sorbitan monolaurate, polyoxyethylene-40-stearate, dimethicone, simethicone, dimethylpolysiloxane, other siloxanes, sorbitan trioleate, sorbitan tristreate, propylene glycol monostearate, sorbitan sesquioleate, diphenyl-methylsilicone, lauryldimethylbenzylammonium chloride, a perfluropolymethylisopropyl ether of about 1500 to about 6600 molecular weight, acacia, type A gelatin, type B gelatin, egg yolk phospholipids, soybean phospholipids, other lipids, cholesterol, colloidal aluminum silicate, colloidal magnesium hydroxide, stearic acid, methylparaben, propylparaben, other suitable surface active chemical agents and the like and their derivatives and mixtures thereof.

The non-liquid antiseptic composition may contain an algesic agent that is capable of increasing the pain sensation that can be felt by a hand when the hand has been wounded by a glove-puncturing object, as a means for rapidly alerting the glove-wearing individual. The algesic agent may be selected from the group consisting of formic acid, acetic acid, citric acid, sodium hydrogen citrate, other acidic citrate salts, other organic acids, phosphoric acid, sodium hydrogen phosphate, sodium phosphate, potassium hydrogen phosphate, other acidic phosphate salts, other phosphate salts, hydrochloric acid, sulfuric acid, sodium hydrogen sulfate, sodium sulfate, other acidic salts, other mineral acids, sodium hypochlorite, potassium hypochlorite, other hypochlorite salts, bradykinin, substance P, bee venom, wasp venom, ant venom, other suitable algesic peptides, algesic proteins, algesic ionophores, potassium chloride, potassium citrate, potassium sulfate, potassium phosphate, potassium carbonate, potassium bromide, potassium iodide, potassium fluoride, potassium hydroxide, potassium nitrate, other potassium salts, other potassium containing chemicals, other algesic organic chemicals, other algesic salts, and the like and mixtures thereof. The above algesic agents may also be capable of providing an acidifying function for some embodiments of the present invention which can enhance the antiseptic acitivity by providing a source of protons, by lowering the pH of the composition or by other means.

The non-liquid antiseptic composition may also contain a colorant or colored substance as a means for providing a color signal to an individual when the glove wall has been punctured by the glove-puncturing object or is otherwise damaged to some extent; the colorant can be selected from the group consisting of the forementioned dyes, any other dyes, any iron oxide, titanium dioxide, any other opacifier, and mixtures thereof. The colorant in the non-liquid antiseptiuc composition, glove walls, or on the glove wall surfaces may not only absorb certain wavelengths of visible light and thus appear colored, but may be fluorescent, phosphorescent, or glow in the dark after exposed to light as a means of enhancing the coloration.

Using one or more of the forementioned colorants, coloration may also function as a form of glove wall decoration to give a glove in accordance with the present invention a more pleasant or interesting appearance. For some embodiments of the present invention, a colored design or print pattern is envisioned which comprises a pattern of small animals including such as teddy bears, lions, giraffes, monkeys, dogs, cats, mice, cows, chickens, pigs, sheep, elephants, birds or other animal facsimiles. Other figures decorating the glove may include clowns, toys, fire trucks, cowboys, dinosaurs, outdoor scenes and the like; in general any scene or object which is pleasing to children and other individuals is imagined to be a useful decoration for the present invention. Glove coloration may be more abstract in pattern as well, may include a camouflage pattern, or more simply color the glove a single color such as pink, purple, white, green, a pastel color, or any other color including a fluorescent color. Preferably glove wall coloration renders the glove wall opaque to help to mask the appearance of the liquid antiseptic composition within the glove wall In addition, printed diagrams, instructions expressions and any other information may be printed onto the glove wall. Printing may accompany the coloration and glove wall decorations or may appear alone on the glove wall. One object of glove wall coloration, decorations, and printing is to entertain and to distract the fears or other negative thoughts of the glove wearer or patients seen by the glove wearer. Such gloves should be particularly amusing to dental patients and other health care patients. For the present invention the method of achieving the coloration decoration and printing of the glove wall is not conceived to be limited to any particular artistic or commercial art methodology.

The non-liquid antiseptic composition may further contain a concentration of a vasocontricting agent, the concentration ranging from about 1 part vasocontricting agent per 200,000 parts of non-liquid antiseptic composition to about 1 part vasoconstricting agent per 2,000 parts of non-liquid antiseptic composition. Should a person using the present invention on a hand become wounded on that hand, then the presence of a vasoconstricting agent in the non-liquid antiseptic composition may be useful to help cause a reduction in blood flow in the hand wound and thereby may help to reduce the immediate dispersion of the infectious pathogen from the wound site by blood flow into the systemic circulation (i.e., the blood circulation, lymphatic circulation, interstitial serum circulation, or by other systemic fluid circulations) of an individual. Any suitable vasoconstricting agent may be selected. Some of the well known vasocontricting ethylamine compounds may be used or any other suitable group of vasoconstricting compounds may be used. Preferably the vasoconstricting agent is selected from the group consisting of epinephrine, norepinephrine, phenylephrine, ephedrine, metaraminol, methoxamine and mixtures thereof.

The non-liquid antiseptic composition can contain a viscosity-modifying agent such as a polymer or a highly-branched molecule of high molecular weight, useful as a means for increasing the viscosity of the non-liquid antiseptic composition so that the composition is prevented from flowing as a liquid until contact may be made with a hand or a hand wound as a result of a glove puncture. The viscosity-modifying agent may bind, associate, solvate with or otherwise complex with liquid solvent molecules in the antiseptic composition and can thereby lower the effective solvent concentration in the antiseptic composition. The final viscosity of the non-liquid antiseptic composition may exceed 5000 centipoise at normal glove temperatures which are generally expected to range between about 10° C. to about 42° C. However, some of the non-liquid antiseptic compositions used in the present invention may have a viscosity below 5000 centipoise; an example would be a foam-forming or foam-type, non-liquid antiseptic composition.

The non-liquid antiseptic compositions used in the present invention can be subdivided into two categories: Group A non-liquid antiseptic compositions do not ordinarily generate a gas during glove wall damage whereas Group B non-liquid antiseptic compositions are capable of generating some gas during glove wall damage. Both Group A and Group B non-liquid antiseptic compositions are defined for the present invention as being not capable of flowing like a liquid.

The non-liquid property of Group A antiseptic compositions for the present invention can be easily demonstrated by the following test. A sample of a Group A non-liquid antiseptic composition warmed to a temperature of 30° C. is placed in an open glass cylindrical tube 1.0 cm high and 1.0 cm in diameter standing on a glass plate in a sealed test chamber controlling the temperature to 30° C., the pressure to 1 atmosphere and the humidity to 50 percent relative humidity. The cylinder is lifted by a mechanical means and the sample is observed for at least five minutes. A liquid sample placed in the cylinder will begin to immediately leak out from the open cylinder bottom where it rests on the glass plate. In contrast for the present invention, a non-liquid antiseptic composition will not begin to leak out from the bottom of the cylinder. Five minutes after the cylinder is lifted, a liquid will increase its 1 cm sample diameter to more than three cm and will substantially flatten in height, whereas a non-liquid sample will not. Because gas production by a test sample of a Group B non-liquid antiseptic composition may cause the test sample diameter to expand in the testing chamber, the Group B antiseptic compositions should be tested only after gas production and associated volume expansion of the test sample have gone to completion. Powdered antiseptic compositions which are solids are clearly not liquids and do not need the above test to demonstrate that they are non-liquids.

The viscosity-modifying polymer or agent may be selected from the group consisting of xantham gum, gum acacia, gum tragacanth, agar, glycyrrhiza, polyvinylpyrrolidone polymers having an average molecular weight between about 500 to about 5000 grams/mole, cross-linked polyvinylpyrrolidone polymers, sodium alginate NF, pectin NF from citrus fruit or apple pomace, other plant gums, theobroma oil (also known as cacao butter or cocoa butter), cellulose, methyl cellulose (Methocel, trademark of Dow Chemical Co.) carboxymethylcellulose (CMC) sodium, hydroxyethyl cellulose (Cellosize, trademark of The Carbide and Carbon Chemicals Corp.), hydroxypropylmethylcelluloses designated Methocel 60, HG, Methocel HG65, Methocel HG70, Methocel HG90 (wherein the number refers to the approximate gel point of a 2 percent solution), other alkylated celluloses including ethylcellulose, hydroxyethyl cellulose, propylcellulose, microcrystalline cellulose (Avicel PH, trademark of FMC Corporation, Philedelphia, Pa.), other suitable chemically-modified celluloses, glycerol, propylene glycol, pyroxylin, polyethylene glycols of between about 150 to more than about 6000 molecular weight, polyethylene glycol 400, polyethylene glycol 4000, polyethylene glycol 4000, polyethylene glycol 6000, gelatin A, gelatin B, glycinerated gelatin, wool fat, beeswax, White petrolatum USP, Petrolatum NF (Petroleum Jelly with a melting point of 42°-60° C.), Plastibase (tradename "Plastibase" from E.R. Squibb & Co., also called Jelene: a combination of mineral oils and heavy hydrocarbon waxes with a molecular weight of about 1300), anhydrous lanolin USP, microcrystalline wax, cholesterol, white wax, hard paraffin wax, yellow soft paraffin wax, white soft paraffin wax, sodium lauryl sulfate, stearyl alcohol, carbowax polyethylene glycol 1000, carbowax polyethylene glycol 1500, carbowax polyethylene glycol 1540, carbowax polyethylene glycol 4000, carbowax polyethylene glycol 6000, other proteins, dimethicones including those more than 1000 centistokes in viscosity, simethicone, dtmethylpolysiloxane, perfluropolymethylisopropyl ethers of 1000 to more than 6600 molecular weight, starch, other alkylated starches, other chemically-modified starches, bentonite USP, sodium bentonite, potassium bentonite, calcium bentonite, magnesium bentonite, hydrogen bentonite, Voloclay bentonite (a combination of sodium bentonite, potassium bentonite, calcium bentonite, magnesium bentonite, and hydrogen bentonite), attapulgite (a hydrous magnesium aluminum silicate that is heat-activated), Veegum (a colloidal magnesium aluminum silicate), carbopol 934 at neutral pH (a trademark acidic polymer of B.F. Goodrich Chemical Co.), benzoinated lard, guar gum, agar, pulverized natural sponge, potato starch, corn starch, other vegetable starches, other plant cellulose fibers, other plant or mineral fibers or polymers, other synthetic polymers and mixtures thereof. It is useful to include the forementioned viscosity-modifying polymers when making compound non-liquid antiseptic compositions such as for example gels, foams, pastes, puttys, greases, and the like and mixtures thereof. The viscosity-modifying polymer help to prevent the antiseptic composition from flowing like a liquid from the glove punture in an uncontrolled manner. Certain polymers such as starch or povidone or other molecules may complex iodine or other antiseptics and buffer their free concentration in the non-liquid antiseptic composition. This effect may need to be taken into account when formulating the non-liquid antiseptic composition.

The non-liquid antiseptic composition may also contain a chemical odor or odorant that is capable of causing either a pleasant or an unpleasant (malodorous) smell. The chemical smell may be caused an aromatic oil, a perfume, an ester, a ketone, an aldehyde, an organic acid, a sulfide, an amine, a flower extract, a plant extract, an animal extract, a mineral extract, or any other suitable chemical. For example the composition may contain a pleasant scented volatile oil such as peppermint oil, menthol, oil of wintergreen, lemon oil and the like, or an unpleasant odor such as pyridine, putrescene, ammonia, vinegar, formaldehyde and the like. When the glove is damaged, the vapors of the chemical odor can freely diffuse from the compartment storing the non-liquid antiseptic composition into the air; useful as a means for further alerting the glove wearer or others that a protective glove has been damaged.

Figure 3:
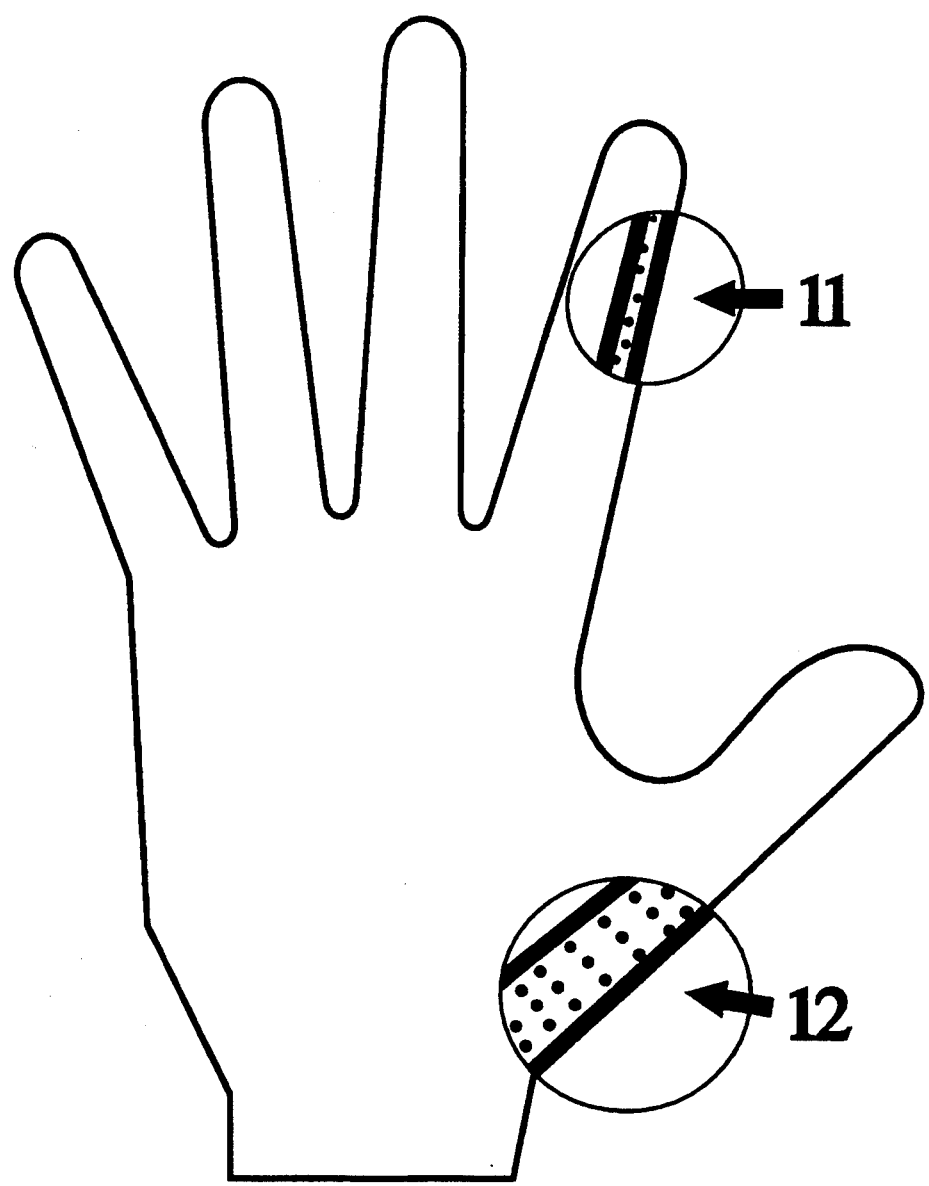
FIG. 3 illustrates a perspective view of a glove in accordance with the present invention, and a partial expanded view of a finger and a partial expanded view of the wrist area; the compartment storing non-liquid antiseptic composition is enlarged in the wrist area of the glove.

Another embodiment of the present invention can be seen by comparing the two partially enlarged sectional views of the glove encircled in FIG. 3: a finger wall sectional view 11 and a wrist wall sectional view 12. The thickness of compartment 4 storing the non-liquid antiseptic composition in wrist wall 12 is significantly increased by design compared to the thickness of the compartment in finger wall 12. The entire wrist area of the glove is expanded by design so that the glove can store additional non-liquid antiseptic composition in the wrist area.

By massaging the glove, the stored non-liquid antiseptic composition can be redistributed by the glove wearer; useful as a means for forcing the non-liquid antiseptic composition to redistribute to other regions of the glove needing additional non-liquid antiseptic composition such as the site of glove damage as depicted in FIG. 2D where an accumulation of the non-liquid antiseptic composition can help to increase the forced extrusion of non-liquid antiseptic composition from the glove during glove massage.

A glove in accordance with the present invention may cover the fingers, palm, back of hand, wrist, forearm or arm; any of these regions of the glove can be modified by design so that a portion of compartment 4 in the selected region may store additional non-liquid antiseptic composition.

Once a particular formulation of non-liquid antiseptic composition has been chosen, a two-layered glove or a multiple-layered glove with an intermediate compartment containing a non-liquid antiseptic composition in accordance with the present invention can be made optionally by several methods. One of the simplest ways to make a glove in accordance with the present invention is first to form the inner glove layer on a hand-shaped mold by one of the known methods used to form standard medical gloves. Any other suitable method for making a glove layer is also acceptable. Often the raw material used to make the glove layer is available in a liquified form which then permits the hand mold to be sprayed or dip coated with the liquid glove layer forming-material to a suitable thickness. The outer glove layers can then be formed on a second hand mold in the same manner. When making two-layered gloves or multiple-layered gloves in accordance with the present invention, the outer glove layer(s) may be made with a larger set of dimensions than the inner glove layer so that a suitably-sized compartment 4 for the non-liquid antiseptic composition is formed when the glove is assembled. After the glove wall layer materials have set, congealed, reacted, dried, cured or solidified sufficiently, the outer surface of the inner glove layer or the glove layers of multiple layered gloves between may be suitably coated with a selected amount of a non-liquid antiseptic composition. Often the non-liquid antiseptic composition can be temporarily liquified by melting it at a temperature above 42° C. (usually the melting temperature is above 55° C.); at such elevated temperatures, the antiseptic composition can then be readily poured, sprayed, painted, coated or otherwise administered conveniently onto the glove layer surfaces as desired. The outer glove layer(s) can then be sequentially slipped over the inner glove layer coated with the non-liquid antiseptic composition. While the composition is still melted, the extra non-liquid antiseptic composition can be removed from or added to the open end of compartment 4. The back open end of a glove in accordance with the present invention may be sealed to completely close compartment 4, or optionally compartment 4 may be left open. Note in multiple layered gloves which are not diagramed herein, compartment 4 may contain one of more of the substances which combined can form a functional non-liquid antiseptic compositionn for the present invention. Thus compartment 4 as defined for the present invention optionally may exist between only some or all glove layers situated between the outermost and innnermost layers comprising the glove wall. A reversible seal may be used at the open wrist end of the glove which comprises a zip-locking connection between the glove layers or any other suitable connecting device can be used. Alternatively, a glove in accordance with the present invention may have a simple structural design as has been described in FIG. 1A wherein inner glove layer 3 and outer glove layer 2 have no special structural material connections. However, it is usually a disadvantage to leave compartment 4 unclosed because the non-liquid antiseptic composition in compartment 4 may dry out or may accidently become squeezed out (extruded) from the glove compartment during prolonged glove storage or glove wear. In addition, if the non-liquid antiseptic composition is flammable, malodorous, contains a colorant, or is otherwise deemed unpleasant then sealing compartment 4 may be necessary. By definition, the sealing of compartment 4 brings the inner and outer glove layers or multiple layers of the glove wall into physical contact so they become structurally connected at least at one point.

A glue or any other connecting means or device may be used to seal or close compartment 4 at the open end of the glove layers. A glue can be used which is capable of suitably bonding rubber, plastic or any other glove layer materials forming the glove wall. The cured glue should not be solubilized nor weakened by contact with the non-liquid antiseptic composition. The preferred sealing glue may contain a silicone, an epoxy polymer, an epoxy resin, a cyanoacrylate, a cyanomethylacrylate, and the like, or any other effective glue or bonding agent that remains suitable in the presence of a particular non-liquid antiseptic composition. For example, one suitable commercially-available silicone rubber cement for bonding rubber to rubber or to plastic is Archer Brand Silicone Rubber Cement (Radio Shack, Fort Worth, Tex., 76102) which contains methyltriacetoxysilane (CAS 004253343), ethyltriacetoxysilane (CAS 017689779), polydimethylsiloxane, and silica (CAS 007631869).

Another alternative method of making a glove in accordance with the present invention is to first form each glove layer on a hand mold, and then slip (or slide) the outer glove layer(s) over the inner glove layer. Non-liquid antiseptic composition is melted at a temperature above 42° C. and then added to suitably fill compartment 4 by using a tube, by an injection method, by a spray means, or by any other method of addition of the non-liquid antiseptic composition into compartment 4. The glove may then be allowed to cool to 23° C. and/or the glove can then be sealed or left open at the glove end and then cooled to 23° C. The order of the steps of assembly of the present invention is generally not important.

Another alternative method for making the present invention is to first add the selected non-liquid antiseptic composition in a melted state (at above 42° C.) beginning with the inside of the chosen outermost glove layer. Then sequentially, the more inner glove layers can be inserted within the outer glove layer. These layers may optionally be coated with the non-liquid antiseptic composition. Before or after the glove has cooled to 23° C., the glove may optionally be sealed or left open at the glove end.

As mentioned, the non-liquid antiseptic composition may simply be a single powdered solid antiseptic substance. The powdered antiseptic could be simply sodium iodide, another iodide salt or another antiseptic which is a solid, defined herein as substances which are solid below 42° C. at normal atmospheric pressure and relative humidity. Generally a glove design in accordance with the present invention, that could be made rather simply and quickly by any individual, in anticipation of needing such a protective medical glove for an upcoming emergency situation, would be the use or wear of two standard medical gloves on each hand, having placed between the first and second glove on each hand, a suitable amount of a non-liquid antiseptic composition in between the gloves worn on each hand.

In general, no specific order and no specific process is envisioned for the steps of assembly of the present invention in any of its embodiments which may comprise the combination of the inner glove layer with optional intermediate glove layers and with the outer glove layer between which glove layers may be added some substances or all of the substances making up the non-liquid antiseptic composition, and optionally, the formation of one or a multiple number of structural connections between some or all of the glove layers of the glove wall of present invention.

Figure 4:
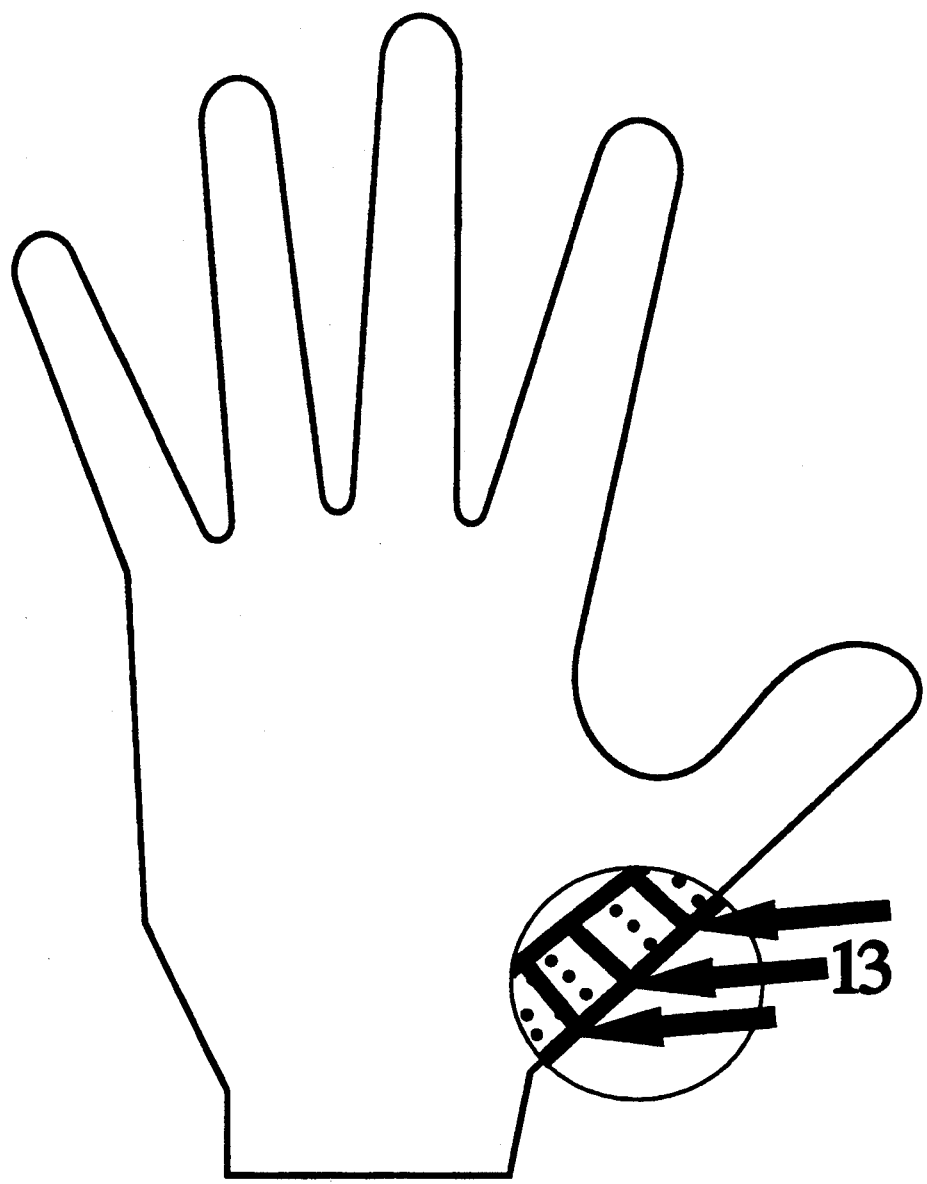
FIG. 4 illustrates a perspective view of a glove in accordance with the present invention with a partial expanded view of the glove wall; the glove has several structural connections between the innner layer and the outer layer of the glove.

Another embodiment of the present invention is illustrated in FIG. 4 in the encircled partially enlarged sectional view; the glove wall may have one structural connection, two structural connections, or a plurality of structural connection 13 (of a third material) in compartment 4 between the outer glove layer (first material) and the outer glove layer (second material). The third material forming a structural connection comprises:

(a) a structural material selected from the group consisting of latex rubber, cis-1,4-polyisoprene rubber, cis-polybutadiene rubber, neoprene rubber, nitrile rubber, silicone rubber, polychloroprene rubber, another halogenated rubber, a case-hardened rubber, another butadiene rubber, a cross-linked rubber, isobutylene-isoprene 1. butyl rubber, butadieneacrylonitrile 1. nitrile rubber, styrene-butadiene rubber, ethylene-propylene copolymer, ethylene-propylene diene terpolymer, polyisobutylene, chlorosulphonated polyeten, ester-type urethan rubber, polychlormethyloxyran epichlorhydrin rubber, epichlorhydrin copolymer with ethyleneoxydichlormethyloxyran copolymer, another rubber, cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polytrifluorochloroethylene plastic, nylon plastic, rayon plastic, polycaprolactam plastic, polyester plastic, urea formaldehyde plastic, polyurethane plastic, isotactic polypropylene plastic, polyamide plastic, phenolic plastic, silicone plastic, another plastic, another synthetic organic fiber, silk fiber, another suitable fiber from an animal secretion, cotton fiber, another plant fiber, wool fiber, another animal hair, leather, another animal fiber, animal skin, animal intestinal tissue, animal connective tissue, metallic fiber, mineral fiber, a glue comprising one or more of the forementioned structural materials, and mixtures thereof; and (b) optionally a colorant selected from the group consisting of titanium dioxide, a dye, an iron oxide and mixtures thereof.

Case hardened rubber may be used in the present invention when a surface of a rubber wall or structural element of the glove may need to have increased resistance to chemical solvents, to the antiseptic and to other substances provided in the present invention. Case-hardening rubber includes using processes that chemically cross-link and strengthen the rubber polymer molecules on the surface of the rubber. In general, synthetic elastomer structural materials may be formed by polymerizing monomeric molecules by an emulsion or solution polymerization process. It is known that the rubber polymers formed may additionally contain a curing agent such as sulfur or a peroxide to cross-link the rubber molecules. Sulfur may be used to crosslink diene containing elastomers while a peroxide is used to cross-link a saturated polymer. It is also known to use an accelerator such as for example an amine derivative, an aldehyde-amine condensation product, a thiazole, a dithiocarbamate, a guanidine derivative, a thiuram, a xantate or a xantogenate to promote the reaction between the sulphur and the rubber molecules because this reaction is otherwise quite slow. It is also known to use a metal oxide activator to make the accelerator more effective sometimes with an organic acid such as stearic acid. The rubber may further contain an antioxidant such as an amine or phenol derivative, a filler for reinforcement or for coloration. The rubber may contain a plasticizer or a softener such as an ester, an adipate, phthalate, silicate, stearate, phosphate, or mineral oil. The use of a plasticizer or softener in the non-liquid antiseptic composition may be used to help to maintain the softness or plasticity of the rubber glove wall, but an excess amount of the softener or the plasticizer may unsuitably modify the rubber wall properties particularily with latex rubber gloves. When the non-liquid antiseptic composition contains a softener such as mineral oil and a glove wall is rubber, preferably the rubber wall is made of solvent resistant rubber such as for example neoprene or a cross-linked rubber. A resin(s) or a rosin(s) may be added to make the rubber tacky or gummy. A typical rubber formulation may contain the following material composition: 100 parts of elastomers, 1-4 parts of fillers, 0.5-2 part of stearic oils, 2-5 parts of zinc oxide, 1-12 parts of plasticizing oils, 1-3 parts of accelerators, 0.5-4 parts of antioxidants, 0-10 parts of resins, and 1-3 parts of sulphur. Infared or ultraviolet light may be used to increase the case-hardening, cross-linking and related chemical production of the rubber used in the present invention.

It is another object of the present invention to provide a glove having a plurality of glove layers acting as a structural connection which reconfigures the compartment storing the non-liquid antiseptic composition into a plurality of compartments capable of storing the non-liquid antiseptic composition.

It is another object of the present invention to provide a glove having a plurality of glove layers acting as a structural connection which reconfigures the compartment storing the non-liquid antiseptic composition into a plurality of compartments (or subcompartments) storing some or all of the components capable of forming the non-liquid antiseptic composition. For some embodiments of the present invention, it is conceivable that the chemical composition of the non-liquid antiseptic composition may be more stable, potent or otherwise more suitable when some of the components of the composition are physically stored separately in the glove from the other substances of the antiseptic composition until as needed, namely when the glove wall may be punctured or otherwise damaged. Thus, any of the forementioned liquid or solid substances that may be used in the non-liquid antiseptic composition may be separately stored in the present invention; for example an antiseptic, a liquid, a viscosity modifying polymer, an algesic, a colorant, a vasoconstrictor, or any of other components or substances that may comprise the non-liquid antiseptic composition can be stored in separate compartments or locations within the glove wall as deemed desirable. Separate locations for the substances in the glove may for example be useful for enhancing the storage life of the glove, may increase antiseptic potency, may increase the antiseptic breadth of spectrum of antiseptic action, may lower the cost of manufacture, may permit the glove wall to have different, variable or regional flexibility properties or may allow the use of some substances in the antiseptic compostion which otherwise might not be possible. In the event of a puncture, the glove wall puncture can be useful as a means for bringing the components of the non-liquid antiseptic composition into contact or some state of mixture particularily at the puncture hole, on the glove-puncturing object, on the hand or in the hand wound should a wound occur, where the components may become mixed together and in some instances may perform a chemical reaction that can form a desired non-liquid antiseptic composition in part or whole; useful as a treatment of non-liquid antiseptic composition that may antiseptically help the hand and the hand wound that may have become contaminated with an infectious pathogen or other contaminant.

From a manufacturing standpoint, a plurality of parallel compartments between two glove layers can be made by a manufacturing process that can sequentially add the desired substances or materials to each subcompartment between the glove layers. The thin compartment which can lie in parallel between the glove's outer and inner layer can be further subdivided into thinner parallel compartments; for example a three layer wall is envisioned having an upper or outer compartment and a lower or inner compartment that are in parallel with the plane of the glove wall. It is envisioned that most often a glove puncturing object would first pass through the outer glove layer, then pass through the outer compartment, then pass through the inner compartment, and then finally pass through the inner glove layer before the object could contact and possibly wound the hand. The motion of the glove puncturing object is capable of transferring some outer compartment substances to mix to some degree with substances of the inner compartment where the mixture could function as a non-liquid antiseptic composition.

It is another object of the present invention to provide a glove having a plurality of glove layers acting as a structural connection which reconfigures the compartment storing the non-liquid antiseptic composition into a plurality of compartments (subcompartments) which macroscopically appear to the human eye (in a glove wall cross-section) to comprise a sponge. The size of each compartment storing the liquid antiseptic composition is not generally critical. Also, any of the compartments, which for the present invention may also be described as subcompartments when there is more than one per glove, may be microscopic in size or could have dimensions almost as large as the thickness of the glove wall. Conceivably the pores in the spongy wall could be as small as a few microns in diameter (a few millionths of a meter). The non-liquid antiseptic composition may be added before, as, or after the spongy wall is formed into its final form.

When the antiseptic composition is added before the sponge has cured to a solid .spongy matrix, the number and size of spongy compartments storing the antiseptic composition can be adjusted by varying the degree of mechanical agitation or ultrasonic energy applied, the temperature, or the amount of gas injected into the batch and subsequently removed by vacuum to form the foam sponge. The ratio of open to closed subcompartments in the glove can be increased by gradual empirical reduction of the ambient pressure to the hardening gloves. As the pressure falls and expands the subcompartments, the walls between neighboring subcompartments can randomly pop open at their thinnest/weakest points and can remain open to each other. Alternatively, elevated pressure can be used to minimize the size of the open compartments and their interconnectedness. Once the spongy glove wall has solidified or cured the porosity of the spongy glove wall is generally irreversible and only the desired percent saturation of the glove wall with the non-liquid antiseptic composition remains a optional variable to modulate. In a solid, melted or vapor form (at elevated temperatures and low pressures) the antiseptic composition can be added to the spongy glove wall. Preferably the spongy glove has a liquid impermeable coating or layer over at least the inner suface and outer surface of the glove wall to prevent exposure of the hand to the non-liquid antiseptic composition, to minimize the drying out of the solvated compositions, and so that the glove may serve as a physical barrier to liquids when the glove wall is intact. The liquid-impermeable (water-proof) coating, layer, or thin film barrier may comprise one or more of the aforementioned structural glove wall materials, such as for example the material composition used to make the spongy wall, and can be applied to the glove in any manner desired.

It is another object of the present invention to provide a glove having a plurality of structural connections that can be used to strengthen the glove wall and/or which can be used to significantly reconfigure compartment 4 storing the non-liquid antiseptic composition into a plurality of subcompartments storing the non-liquid antiseptic composition. Every subcompartment or only a portion/fraction of all of the subcompartments may be connected to at least one other adjacent subcompartment. Such connections allow a glove to be capable of being massaged to optionally redistribute the non-liquid antiseptic composition in the glove wall as desired as illustrated in FIG. 2C.

Alternatively for some embodiments of the present invention, each subcompartment may constitute a closed space. Such a glove wall structure can be used to provide gloves capable of expelling or extruding an expanding foam or other expanding non-liquid antiseptic composition during and after a glove wall puncture. In addition, it is important to note that such gloves may also be capable of generating in the local environments of the glove puncture as well as on the surfaces of the glove-puncturing object, hand, and hand wound area should a wound occur, a gaseous antiseptic or other chemical antiseptic; useful as an antiseptic treatment to a hand and a hand wound.

For example, for some embodiments of the present invention, the expulsion of a non-liquid antiseptic composition from some of the subcompartments can be automatically triggered. A glove puncture through several subcompartments of the glove wall can be designed to anticipate a passive combination and mixing of some of the non-liquid antiseptic components from the damaged subcompartments. The combination and mixing of the components can cause a physical or chemical reaction therein that may be capable of generating a positive pressure between normal atmospheric pressure and up to about three times atmospheric pressure; useful as an automatic means for forcing the expulsion of non-liquid antiseptic composition from the punctured subcompartments during the glove puncture by an object and thereafter for a period of time. More specifically for example, some of the subcompartments may contain one of the commonly used mineral or organic acids in a liquid solution form, at a acid concentration of between about 0.5 percent and about 100 percent; water would be the principal liquid diluent in the solution. Suitable acids for the above purpose would include the following: hydrochloric acid, sulfuric acid, phosphoric acid, acetic acid, formic acid, propionic acid, lactic acid, and the like. Alternatively, the acid may be a dicarboxylic or tricarboxylic acid such as oxalic acid, succinic acid, malic acid, maleic acid, citric acid, tartaric acid, malonic acid and the like. The physical state of the acid is not critical so long as the chemical is capable of providing protons to the remainder of the non-liquid antiseptic composition when mixing occurs as a result of a glove wall puncture. The remaining components of the non-liquid antiseptic composition would include a gas-releasing base such as for example a bicarbonate compound that can be situated in glove wall subcompartments adjacent to the subcompartments containing the acid. Bicarbonate chemicals are capable of producing carbon dioxide gas when contacted by an acid. Carbonate base compounds are also suitable although more acid is required: sodium carbonate, potassium carbonate, calcium carbonate, magnesium carbonate, strontium carbonate, barium carbonate, choline carbonate, ditetramethyammonium carbonate, ditetraethylammonium carbonate, propylene carbonate, butylene carbonate and other nontoxic carbonate compounds may be used. Combinations which may generate toxic salts such as barium chloride or strontium chloride should be avoided. The simple combination of the acid and gas-producing base chemicals is capable of generating various sized and various amounts of gas bubbles of carbon dioxide gas in the non-liquid antiseptic composition depending upon the substances present to stabilize the bubbles formed. In any case the gas production in the glove wall can provide a means for pressurizing the non-liquid antiseptic composition to cause it to expand in the vicinity of the glove wall puncture site and to become actively expelled wherever possible from the glove wall puncture hole onto the hand and into hand wound as a non-liquid foam or semi-gelatinous or creamy paste; useful as a prophylactic non-liquid antiseptic composition treatment to the hand and the hand wound should a wound occur by an object contaminated with an infectious pathogen.

Alternatively, for some embodiments of the present invention, a peroxide chemical compound may be used to produce a gas. Examples of sutable peroxides include but are not limited to the following examples: (a) hydrogen peroxide; (b) magnesium peroxide or sodium peroxide (metal peroxides); or (c) benzoyl peroxide or succinyl peroxide (organic peroxides); and mixtures thereof. The liquid solvent for the peroxide would be water when hydrogen peroxide, benzoyl peroxide or succinyl peroxide is employed. The liquid solvent, diluent, or suspending agent would be an anhydrous oil or non-reactive organic fluid when a metal peroxide is employed due to the instability of these compounds in water. A peroxide stabilizing additive may be included with the peroxide to prolong the stability of the peroxide during glove storage before glove use. Subcompartments adjacent to the subcompartment(s) containing the peroxide may store the other components of the non-liquid antiseptic composition such as for example a powdered metal oxide catalyst capable of safely catalyzing rapid chemical decomposition of the peroxide into oxygen gas. The catalyst may be manganese dioxide, other finely powdered metals and metal oxides or any suitable chemical agent that is capable of suitably and safely decomposing a peroxide during chemical contact with it. The contact of the peroxide with the catalyst is useful as a means for generating gas bubbles in the non-liquid antiseptic composition; the gas production is useful as a means for altering the ambient gas pressure of the mixture so that the local mixture expands as a foaming mixture from the glove wall puncture site. The foaming mixture can exit from the glove wall onto the hand and into hand wound as a foam, gel, paste or creme of non-liquid antiseptic composition which can be useful as a non-liquid antiseptic composition treatment to the hand and the hand wound should a wound occur. In addition, the high oxygen partial pressure in the mixture may provide antiseptic acitivity. A more than a 3 percent hydrogen peroxide solution may be used so that the final concentration of peroxide in the extruded non-liquid antiseptic composition is at least 3 percent. A 3 to 30 percent hydrogen peroxide concentration is known to have useful antiseptic activity. Well known combinations of metals with the forementioned acids can also produce hydrogen gas which can be used for the present invention to gas pressurize the non-liquid antiseptic composition as well. For some glove uses, a nonflammable gas such as carbon dioxide may be most preferable.

Alternatively, for some embodiments of the present invention, the combination of the subcompartment materials occurring during a glove puncture can be used to produce an antiseptic in a more suitable or potent form. For example, the mixing of glove subcompartments may be used as a means for locally activating/releasing a suitable amount of a halogen-containing antiseptic chemical. For example, a chlorine containing compound such as sodium hypochlorite can be brought into contact with a liquid acid such as hydrochloric acid to form a non-liquid (foam, paste, or gel) antiseptic composition containing suitable amounts of hypochlorous acid, chlorine dioxide, and chlorine gas; these chemicals are known to be rapidly acting, potent antiseptics. The expulsion of this non-liquid antiseptic composition from a glove puncture optionally can be further facilitated by adding a carbon dioxide gas generating system which is also activated by the glove wall puncture; useful as an extrusion means for a foam, gel, paste or other type of non-liquid antiseptic composition to help to provide an antiseptic treatment to the hand and hand wound.

For some embodiments of the present invention, similar to the forementioned approach, some subcompartments may contain an alcohol/water solution of elemental iodine with an iodide salt, and optionally a bicarbonate base compound, while other adjacent subcompartments contain a liquid acid solution. Saturated solutions of elemental iodine and a iodide salt may be used in aqueous solutions containing 25 to 95 percent of a suitable alcohol. Preferably about 70 to 90 parts of an alcohol, preferably ethanol or isopropanol, is used with 10 to 30 parts of water and 0.1 to 5 parts of elemental iodide and 0.1 to 10 parts of sodium iodide. When a glove puncture by an object brings the contents of several subcompartment together into contact by some mixture, acidified and reactive iodide compounds which are formed as a result including HOI (hypoiodous acid) and HI (hydriodic acid) from the reaction of water with $I_2$ (elemental iodine) can have rapid potent antiseptic activity. The iodide anion ($I^-$) in the mixture can react with $I_2$ to form $I_3^-$; and is known to be useful for forming a soluble complex form of iodine as a resevoir of $I_2$ in solution. Optionally the mixture may also contain a gas-producing system to produce a gas capable of forming a foam to extrude the non-liquid (foam, gel, paste or other non-liquid forms) of the antiseptic composition from the glove puncture onto the hand and into the hand wound should a wound occur; useful as an relatively immediate antiseptic treatment.

Another embodiment of the present invention is a glove wherein only a portion of the subcompartments of the glove are closed and wherein a portion of the subcompartments are open so that a suitable combination of the forementioned protective antiseptic processes and systems can be automatically and/or manually acted upon at the discretion of the glove wearer.

According to another embodiment of the present invention, the compartment of the glove storing non-liquid antiseptic composition is connected to one or more additional reservoir(s) of non-liquid antiseptic composition which optionally can be opened to release their contents. Accordingly a reservoir may be incorporated by design anywhere on the glove. Preferably an additional reservoir of non-liquid (foam, gel, or paste) antiseptic composition would be positioned on the proximal (wrist) region of the glove. In some embodiments of the present invention, the additional reservoir(s) may each store only small quanities of the antiseptic composition; for example at most 0.1 milliliters of non-liquid antiseptic composition. For other embodiments of the present invention, the additional reservoir(s) may retain up to about 25 milliliters of non-liquid antiseptic composition. A reservoir may be of a semi-spherical (dome) shape, an annular shape, a semi-annular design or of any useful shape provided that it can provide a manually-accessible reservoir of non-liquid antiseptic composition upon demand as needed for the hand and for a hand wound should one occur. In the event of hand wounding, the reservoir(s) may be massaged, pushed, rolled forward, forced down on a firm surface, or pressurized by any other means to expell the non-liquid antiseptic composition from each reservoir into the compartment(s) of the glove wall and from there to the hand wound site. Any means of resevoir massage would be also useful. Any conceivable reservoir design may be acceptable, including a design that incorporates a reinforced area within the glove to withstand the internal and external pressures that may arise during reservoir massage. There may be a conduit(s) with a one-way or "flapper" valve between the reservoir(s) and compartment 4 of the glove; useful to maintain the massage pressure gradients arising in the glove to help to direct and maintain the outward expulsion of the non-liquid antiseptic composition from the glove; the object of the additional reservoir(s) is to provide additional means for increasing the expulsion of non-liquid antiseptic composition from compartment 4 of the glove when the glove wall has been punctured, so that sufficient antiseptic can be tranferred to wherever it is thought to be needed on the hand.

The embodiments of the present invention that are illustrated below may include details for making the non-liquid antiseptic composition on a small scale and use glass beaker containers. Metal or porcelain containers may be used instead of glass beakers when the present invention is mass produced. Furthermore, the order of the combination of substances used to produce the present invention is not limited to methods or order of manufacture described herein. The illustrated embodiments are therefore not limiting examples and only provide an illustration of useful methods for producing the present invention.

The antiseptic composition stored within the glove wall compartment(s) or subcompartments may be a non-liquid, or the antiseptic composition may be capable of forming a non-liquid antiseptic composition when an object punctures a glove wall of the present invention. In the latter case, the components of the complete non-liquid antiseptic composition may be designed to become suitably mixed together during a glove wall puncture by an object. In this latter case, the components can be liquid(s) or non-liquid(s) or mixtures thereof.

Automatic assembly of the components of the antiseptic composition into a non-liquid mixture during or following glove puncture is a useful object for some embodiments of the present invention. The non-liquid antiseptic components may be assembled to form a suitable non-liquid mixture on a portion of a surface of the glove-puncturing object, around the glove wall puncture hole, on the hand underneath the glove wall puncture hole, or in a hand wound should a wound occur. The mixture can help to provide a non-liquid antiseptic composition capable of helping to destroy infectious pathogens that the glove-puncturing object may have been carried to the glove, hand or hand wound.

Many embodiments of the present invention are envisioned. In general, flexible protective medical gloves of the present invention can be designed to help to provide specific protection from a particular infectious pathogen or can be designed to help to provide a broad spectrum of antiseptic activity against infectious pathogens. Gloves of varying size, wall thickness, compartmentation and flexibility can be designed for specific or general glove wear needs.

In another embodiment of the present invention, a glove in accordance with the present invention contains a non-liquid antiseptic composition which comprises:
(a) about 0.02 to about 25 parts of povidone-iodine;
(b) about 0.02 to about 2.5 parts of methylparaben;
(c) about 0.01 to about 1.5 parts of propylparaben;
(d) about 5 to about 15 parts sodium lauryl sulfate;
(e) about 20 to 120 parts of propylene glycol;

(f) about 100 to 300 parts of stearyl alcohol;
(g) about 100 to 300 parts of a petrolatum;
(h) about 100 to 400 parts of sterile water; and
(i) about 25 to about 250 parts of an alcohol selected from the group consisting of ethanol, isopropanol, propanol, butanol, sec-butanol, tert-butanol, benzyl alcohol, methanol, cetyl alcohol, and mixtures thereof.

To make the above composition in a non-liquid state, first the stearyl alcohol and petrolatum can be heated in a glass beaker on a steam bath to about 75° C. The other ingredients previously dissolved in the water, can then be added with mixing at a temperature of 75° C. One or more milliliters of the composition may be added to fill a glove compartment before the composition congeals.

In another embodiment of the present invention a glove in accordance with the present invention contains a non-liquid antiseptic composition which comprises:
(a) about 0.02 to about 20 parts of povidone-iodine;
(b) about 0.1 to about 90 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight; and
(e) about 0.1 to about 90 parts of an alcohol, the alcohol selected from the group consisting of ethanol, isopropanol, propanol, n-butanol, sec-butanol, tert-butanol, benzyl alcohol, methanol, cetyl alcohol, stearyl alcohol, and mixtures thereof.

To make the above composition in a congealing form, the two polyoxyethylene glycole can be heated in a glass beaker on a steam bath to about 65° C. The other ingredients and antiseptic can then be added with mixing, previously dissolved in the water and at a temperature of 65° C. One or more milliliters of the composition may be added to fill a glove compartment before the composition congeals.

In another embodiment of the present invention a glove in accordance with the present invention contains a non-liquid antiseptic composition which comprises:
(a) about 0.02 to about 20 parts of povidone-iodine;
(b) about 0.1 to about 90 parts of water;
(c) about 0.05 to about 30 parts of cholesterol;
(d) about 0.05 to about 30 parts of stearyl alcohol;
(e) about 10 to 100 parts of a wax;
(f) about 500 to about 1000 parts petrolatum; and
(g) about 0.1 to about 300 parts of an alcohol selected from the group consisting of ethanol, isopropanol, propanol, n-butanol, sec-butanol, tert-butanol, benzyl alcohol, methanol, cetyl alcohol, and mixtures thereof.

To form the above composition, the stearyl alcohol, wax, and petrolatum can be melted on a steam bath and the cholesterol can then be added. The remaining ingredients can be combined and heated on a steam bath and then added with mixing. One or more milliliters of the composition may be added to fill a glove compartment before the composition congeals.

In another embodiment of the present invention a glove in accordance with the present invention contains a non-liquid antiseptic composition which comprises:
(a) about 0.02 to about 20 parts of povidone-iodine;
(b) about 0.1 to about 90 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight;
(e) about 1 to about 5 parts of sorbitan monopalmitate (SPAN 40); and
(f) about 0.1 to about 90 parts of an alcohol, the alcohol selected from the group consisting of ethanol, isopropanol, propanol, n-butanol, sec-butanol, tert-butanol, benzyl alcohol, methanol, and mixtures thereof.

To form the above composition, the polyoxyethylene glycols and SPAN 40 together in a glass beaker water can be warmed in a water bath at 70° C. After combining the remaining ingredients with the water and heating them to 70° C., the ingredients may then be added to the polyoxyethylene mixture with mixing. One or more milliliters of the composition may then be used to fill a glove compartment before the composition congeals.

In another embodiment of the present invention a glove in accordance with the present invention contains a non-liquid antiseptic composition which comprises:
(a) about 0.02 to about 20 parts of povidone-iodine;
(b) about 0.1 to about 90 parts of cetyl alchol;
(c) about 1 to 10 parts of a wax;
(d) about 5 to about 20 parts of propylene glycol;
(e) about 0.1 to about 4 parts of sodium lauryl sulfate; and
(e) about 10 to 80 parts of sterile water.

To make the above composition, the cetyl alcohol and wax in the propylene glycol in a glass beaker can be melted on a water bath heated to 65° C. The sodium lauryl sulfate can be dissolved in the water and povidone-iodine in a glass beaker which is heated to 65° C. The oily liquid may then be added slowly to the water while the water is being well stirred. Stir the mixture for an additional 15 minutes or until good mixing has been achieved. One or more milliliters of the composition may be added to fill a glove compartment before the composition congeals.

In another embodiment of the present invention a glove in accordance with the present invention contains a non-liquid antiseptic composition which comprises:
(a) about 0.02 to about 20 parts of povidone-iodine;
(b) about 0.1 to about 45 parts of cetyl alcohol;
(c) about 1 to about 40 parts of mineral oil;
(d) about 3 to about 27 parts of a petrolatum;
(e) about 0.1 to about 5 parts of sodium lauryl sulfate; and
(f) about 7 to about 60 parts of sterile water.

To make the above composition, the cetyl alcohol can be melted in a beaker over a water bath, and then the sodium lauryl sulfate can be added while mixing well. The petrolatum and mineral oil can be added while heating so that the mixture melts completely and allow to cool to 23° C. Combine the water and povidone-iodine to make a solution at 23° C. in a beaker and then this aqueous solution can be added slowly with constant mixing to the cooled petrolatum composition. One or more milliliters of the composition may be added to fill a glove compartment.

In another embodiment of the present invention a glove in accordance with the present invention contains a non-liquid antiseptic composition which comprises:
(a) about 0.02 to about 20 parts of povidone-iodine;
(b) about 0.1 to about 60 parts of water;
(c) about 0.05 to about 40 parts of a polyoxyethylene glycol of between about 150 to about 1540 molecular weight;

(d) about 0.05 to about 40 parts of a polyoxyethylene glycol of between about 1540 to about 6000 molecular weight;
(e) about 5 to about 20 parts of 1,2,6-hexanetriol; and
(f) about 0.1 to about 20 parts of an alcohol, the alcohol selected from the group consisting of ethanol, isopropanol, propanol, n-butanol, sec-butanol, tert-butanol, benzyl alcohol, methanol, cetyl alcohol, stearyl alcohol, and mixtures thereof.

To make the above composition, the higher molecular weight polyoxyethylene can be heated with the 1,2,6-hexanetriol in a glass beaker on a water bath to between 60° C. and about 75° C. When they are melted, then the lower molecular weight polyoxyethylene glycol can be added with strong mixing. Then the water, alcohol(s) and povidone-iodine can be combined in a glass beaker and heated to 65° C. using a steam bath. Then slowly this solution should be added with vigorous mixing to the polyoxyethylene glycol/hexanetriol mixture. One or more milliliters of the composition may be added to fill a glove compartment before the composition congeals.

In another embodiment of the present invention a glove in accordance with the present invention contains a non-liquid antiseptic composition which comprises:
(a) about 0.02 to about 20 parts of povidone-iodine;
(b) about 0.1 to about 90 parts of water;
(c) about 1 to about 50 parts of glycerol monostearate;
(d) about 1 to about 100 parts of glycerin;
(e) about 0.1 to about 10 parts of bentonite; and
(f) about 0.1 to about 90 parts of an alcohol, the alcohol selected from the Group consisting of ethanol, isopropanol, propanol, n-butanol, sec-butanol, tert-butanol, benzyl alcohol, methanol, cetyl alcohol, stearyl alcohol, and mixtures thereof.

To make the above composition, one may dissolve the povidone-iodine in the half of the water and half of the alcohol(s) (by volume) in a glass beaker and then carefully lay the bentonite on the water's surface to allow it to self-wet. One may then stir the mixture until a uniform magma is produced. Melt the glycerol monostearate in the glycerin in another beaker on a steam bath. Heat the bentonite magma to the same temperature as the glycerols, and combine the two liquids with stirring. One may then add the remaining water and alcohol while stirring. One or more milliliters of the composition may be added to fill a glove compartment before the composition congeals.

In another embodiment of the present invention a glove in accordance with the present invention contains a non-liquid antiseptic composition which comprises:
(a) about 0.02 to about 20 parts of povidone-iodine;
(b) about 0.1 to about 90 parts of water;
(c) about 0.1 to 5 parts of a methylcellulose (such as for example, a hydroxypropylmethyl cellulose such as Methocel 60 HG, Methocel 70 HG, Methocel 90 HG and the like—available for example from Dow Corning Chemical Co.) or a hydroxyethyl cellulose (such as for example, Cellosize—available from The Carbide & Carbon Chemicals Corp.);
(d) about 0.01 to about 3 parts of Carbopol 934—available from B.F. Goodrich Chemical Co. and/or the like polymers;
(e) about 0.01 to about 2 parts of methylparaben (or another paraben); and
(f) 0.1 to about 20 parts of propylene glycol.

To make the above composition, the methyl- or hydroxyethyl- or hydroxypropylmethyl-cellulose and the povidone-iodine can be added to half of the water to be used in the composition (previously heated to between about 80° C. to about 90° C.) in a first glass beaker. The mixture can be mixed for 10 minutes, cooled to 10° C., and then rested for between about 6 to about 30 hours. In a second glass beaker, the Carbopol 934 can be dissolved in the remainder of the water and the pH of the Carbopol 934 can be adjusted to between pH 6.5 and 7.5 using a dilute hydroxide base solution or other base (metal or organic). In a third glass beaker, the methylparaben can be dissolved in the propylene glycol. The contents of the three glass beakers may then be combined but avoid whipping air into the mixture. One or more milliliters of the composition may be added to fill a glove compartment before the composition congeals.

In another embodiment of the present invention, a glove in accordance with the present invention contains a non-liquid antiseptic composition which comprises:
(a) about 1 to about 20 parts of an antiseptic;
(b) about 1 to about 5 parts of the viscosity-modifying agent hydroxyethylcellulose;
(c) sodium hydroxide or acetic acid added to titrate the composition pH to pH 4 to pH 8 as desired;
(d) about 1 to about 70 parts of glycerin as a liquid solvent; and
(e) about 1 to about 25 parts of delta gluconolactate as a latent acid catalyst to neutralize the hydroxyethylcellulose.

To make the above composition, the hydroxyethylcellulose can be added to the antiseptic and the glycerin (previously heated to between about 50° C. to about 90° C.) in a glass beaker. The antiseptics which may be used in this composition include but are not limited to the following: chlorhexidine gluconate, nonoxynol-9, and other antiseptics that are compatible with cellulose polymers. The liquified mixture can be mixed for 20 minutes and the pH adjusted to a pH between about 4 and about 8; preferably to about pH 4 to about 6; most preferably to a pH of about 4.5. After 30 minutes of mixing, the delta gluconolactone may be added. After an additional 30 minutes, the hot liquid mixture pH can be adjusted further if needed. One or mope millilters of the composition may be added to fill a glove compartment before the composition congeals at lower tempertaures. This gel composition can be useful in latex gloves when rubber wall softening or weakening may be a design concern.

In another embodiment of the present invention a glove in accordance with the present invention contains a non-liquid antiseptic composition which comprises:
(a) about 0.02 to about 20 parts of povidone-iodine;
(b) about 0.1 to about 90 parts of water;
(c) about 1 to about 50 parts of glycerol monostearate;
(d) about 1 to about 100 parts of glycerin;
(e) about 0.1 to about 10 parts of bentonite; and
(e) about 0.1 to about 90 parts of an alcohol, the alcohol selected from the group consisting of ethanol, isopropanol, propanol, n-butanol, sec-butanol, tert-butanol, benzyl alcohol, methanol, cetyl alcohol, stearyl alcohol, and mixtures thereof.

The bentonite can be sprinkled on top of about two-thirds of the water heated to about 60° C. and allowed to become wet. With mixing a uniform magma can be made. The glycerol monostearate can be melted at about 60° C. in the glycerin heated on a water bath and then added to the magma at preferably the same temperature. The mixture can be stirred as it cools and the remainder of the water can be added. One or more milliliters of the composition may be added to fill a glove compartment before the composition has congealed.

In another embodiment of the present invention a glove in accordance with the present invention contains a non-liquid antiseptic composition which comprises:
(a) about 0.02 to about 20 parts of povidone-iodine;
(b) about 0.1 to about 40 parts of water;
(c) about 0.05 to about 30 parts of a polyoxyethylene glycol of between about 150 to about 1540 molecular weight;
(d) about 5 to about 40 parts of a polyoxyethylene glycol of between about 1540 to about 6000 molecular weight; and
(e) about 0.1 to about 90 parts of cetyl alcohol or stearyl alcohol and mixtures thereof.

To make the above composition in a congealing form, the two polyoxyethylene glycols can be heated in a glass beaker on a steam bath to about 75° C. The other ingredients can then be added with mixing, previously dissolved in the water and at a temperature of 65° C. One or more milliliters of the composition may be added to fill a glove compartment before the composition congeals. It is possible to incorporate water or aqueous solutions to the extent of 20% or alcoholic solutions not exceeeding 5% of the total formula. The inclusion of a small percentage of cetyl alcohol or stearyl alcohol tends to inhibit the solubilizing effects of water, alcohol, or organic acids on the carbowax-polyethylene glycol mixtures. (See Remington's Pharmaceutical Sciences, 13th edition (1965) page 533–534.)

In another embodiment of the present invention a glove in accordance with the present invention contains a non-liquid antiseptic composition which comprises:
(a) about 0.02 to about 20 parts of povidone-iodine;
(b) about 0.1 to about 10 parts of water;
(c) about 0.05 to about 30 parts of a polyoxyethylene glycol of between about 150 to about 1540 molecular weight;
(d) about 5 to about 40 parts of a polyoxyethylene glycol of between about 1540 to about 6000 molecular weight; and
(e) about 0.1 to about 30 parts of polyethylene glycol 400 monostearate.

To make the above composition in a congealing form, the two polyoxyethylene glycols can be melted together in a glass beaker on a steam bath to about 70° C. and mixed while allowing the mixture to cool to about 45° C. In a second container, the polyethylene glycol 400 monostearate can be melted at about 45° C. and the other ingredients can then be added with mixing till a smooth mixture is obtained. The two mixtures can then be combined at about 45° C. and stirred until an ointment is obtained. One or more milliliters of the composition may be added to fill a glove compartment before the composition congeals.

In another embodiment of the present invention a glove in accordance with the present invention contains a non-liquid antiseptic composition which comprises:
(a) about 0.1 to about 20 parts of povidone-iodine;
(b) about 0.01 to about 0.1 parts of calcium citrate;
(c) about 1 to about 6 parts of sodium alginate;
(d) about 0.01 to about 1 part of methylparaben;
(e) about 1 to about 60 parts of glycerin;
(f) about 1 to about 50 parts of water; and
(g) about 1 to about 50 parts of an alcohol selected from the group consisting of methanol, ethanol, isopropanol, propanol, and mixtures thereof.

The calcium citrate can be dissolved with the methylparaben in the water. The glycerin and alcohol can be mixed with the sodium alginate to form a smooth paste. The aqueous solution can be mixed into the paste and stirred till stiffening begins. One or more milliliters of the composition may be added to fill a glove compartment before the composition fully stiffens. Stiffening may take several hours.

Instead of using the antiseptic povidone-iodine in the above formulated embodiments of the present invention, another antiseptic may be used above in its place or optionally, a combination of two or more antiseptics may be used instead of povidone-iodine in the above formulated embodiments of the present invention. Optionally the same antiseptic parts range as provided above may be used. Futhermore, optionally, the above embodiments of the present invention may be made and used without including an alcohol in the antiseptic composition.

In another embodiment of the present invention a glove in accordance with the present invention contains a non-liquid antiseptic composition which comprises:
(a) about 0.1 to about 25 parts of sodium hypochlorite;
(b) about 50 to 99 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight; and
(e) about 0.1 to about 90 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof.

To make the above composition in a congealing form, the two polyoxyethylene glycols can be heated in a glass beaker on a steam bath to about 65° C. The other ingredients and antiseptic can then be added with mixing, previously dissolved in the water and at a temperature of 85° C. One or more milliliters of the composition may be added to fill a glove compartment before the composition congeals.

In another embodiment of the present invention a glove in accordance with the present invention contains a non-liquid antiseptic composition which comprises:
(a) about 0.1 to about 25 parts of chlorhexidine gluconate;
(b) about 0.1 to about 90 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight; and
(e) about 0.1 to about 90 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof.

To make the above composition in a congealing form, the two polyoxyethylene glycols can be heated in a glass beaker on a steam bath to about 65° C. The other ingredients and antiseptic can then be added with mixing, previously dissolved in the water and at a temperature of 65° C. One or more milliliters of the composition may be added to fill a glove compartment before the composition congeals.

In another embodiment of the present invention a glove in accordance with the present invention contains a non-liquid antiseptic composition which comprises:
(a) about 0.1 to about 50 parts of nonoxynol-9;
(b) about 0.1 to about 95 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight; and
(e) about 0.1 to about 90 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof.

To make the above composition in a congealing form, the two polyoxyethylene glycols can be heated in a glass beaker on a steam bath to about 65° C. The other ingredients and antiseptic can then be added with mixing, previously dissolved in the water and at a temperature of 65° C. One or more milliliters of the composition may be added to fill a glove compartment before the composition congeals.

The preferred embodiment of the present invention is a glove in accordance with the present invention which contains a non-liquid antiseptic composition which comprises:
(a) about 0.1 to about 16 parts of elemental iodine;
(b) about 0.1 to about 16 parts of potassium iodide;
(c) about 0.1 to about 25 parts of water;
(d) about 0.05 to about 30 parts of a polyoxyethylene glycol of between about 150 to about 1540 molecular weight;
(e) about 0.05 to about 30 parts of a polyoxyethylene glycol of between about 1540 to about 6000 molecular weight;
(f) about 0.1 to about 50 parts of glycerin; and
(g) about 0.1 to about 75 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof.

To make the above composition in a congealing form, the two polyoxyethylene glycols can be heated in a glass beaker on a steam bath to about 65° C. The other ingredients and antiseptic can then be added with mixing, previously dissolved in the water and at a temperature of 65° C. One or more milliliters of the composition may be added to fill a glove compartment before the composition congeals.

In another embodiment of the present invention a glove in accordance with the present invention contains a non-liquid antiseptic composition which comprises:
(a) about 0.1 to about 16 parts of elemental iodine;
(b) about 0.1 to about 16 parts of potassium iodide;
(c) about 0.1 to about 30 parts of yellow wax;
(d) about 0.1 to about 22 parts of wool fat;
(e) about 5 to about 80 parts of petrolatum;
(f) about 0.1 to about 50 parts of Glycerin; and
(g) about 0.1 to about 40 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof.

To make the above composition in a congealed form, the yellow wax, wool fat and petrolatum may be melted together on a steam bath and then allowed begin to congeal into an ointment base. The iodine and potassium iodine are dissolved in the glycerin and alcohol at a temperature below 70° C. and then cooled to the same temperature as the ointment. The antiseptic solution is then mixed into the ointment base using a slow speed (10–120 revolutions per minute mechanical paddle) and then allowed to cool slowly. One or more milliliters of the composition may be added to fill a glove compartment before the composition congeals.

In another embodiment of the present invention a glove in accordance with the present invention contains a non-liquid antiseptic composition which comprises:
(a) about 0.1 to about 10 parts of mecuric red oxide;
(b) about 0.1 to about 8 parts of petrolatum;
(c) about 0.1 to about 40 parts of wool fat; and
(d) about 0.05 to about 23 parts of yellow wax.

To make the above composition in a congealing form, the mecuric red oxide antiseptic can be blended in the petrolatum after it has been melted on a steam bath. During continued heating and stirring, the wool fat and yellow wax are then added until a smooth blend is obtained. One or more milliliters of the composition may be added to fill a glove compartment before the composition congeals.

In another embodiment of the present invention a glove in accordance with the present invention has at least two compartments in parallel to the glove wall, wherein at least one of the compartments parallel to the glove wall, called compartment A, contains an acidic solution which comprises:
(a) about 0.1 to about 50 parts of a 1 to 30 percent aqueous solution of a mineral acid, organic acid, or of a buffered mixture of relatively acidic salts;
(b) about 0.1 to about 90 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof;
(c) about 0.05 to 5 parts of a surface-active agent or a detergent;

and wherein at least one of the other compartments, called compartment B, that is parallel to the glove wall and to compartment A, contains an antiseptic composition which comprises:
(a) about 0.1 to about 50 parts of an antiseptic, other than an organic acid, a mineral acid, or a buffered mixture of relatively acidic salts;
(b) about 0.1 to about 95 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight; and
(e) about 0.1 to about 90 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof;
(f) about 0.05 to about 10 parts of a surface-active agent or a detergent;
(g) about 0.1 to about 50 parts of a bicarbonate salt or a carbonate salt capable of releasing some carbon dioxide gas upon exposure of the salt to an acid, or about 0.1 to about 50 parts of a fine metal powder, including for example magnesium, zinc, or another suitable metal that is capable of producing some hydrogen gas upon contact of the metal powder grains with an acid;

and wherein contact between the acidic solution and the antiseptic composition, which may arise as a result of a glove wall puncture by an object, can provide at least some combinational mixing of the substances of compartments A and B of the glove, the mixture capable of forming some expanding non-liquid antiseptic composition, which can appear to be foamy or creamy, the expanding property of the composition rendering the composition to be capable of some self-expulsion from a glove wall puncture and some transfer onto the hand or into a hand wound should a wound be caused by the object during the glove wall puncture.

The acidic substances used in compartment A can be mixed together at room temperature and may be poured into compartment A which can be sealed to prevent its leakage. To prepare the antiseptic composition for compartment B, the two polyoxyethylene glycols can be heated in a glass beaker on a steam bath to about 65° C. In a second container the other ingredients and antiseptic(s) are dissolved in the water, heated to a temperature of 65° C., and then can be added with mixing to the liquified mixture of polyoxyethylene glycols. While the complete compartment B composition is still liquified, it is added to compartment B. At the same time or after cooling to room temperature, compartment B should be sealed to avoid leakage.

Contact between the compartment A and compartment B compositions during glove manufacture should be avoided to avoid premature formation of the expandable non-liquid antiseptic composition. In addition, when halogen-containing antiseptics or a halide salt are used in the above embodiment of the present invention, contact between acid from compartment A and a halogen-containing antiseptic or halide salt from compartment B may produce a halogen gas. For example, if compartment B contains a hypochlorite salt such as sodium hypochlorite and it is contacted by an acid such as hydrochloric acid, then some chlorine gas will evolve. For some embodiments of the present invention, suitable small amounts of halogen gas can be provided by the present invention at the glove puncture site; useful as a mobile gaseous antiseptic capable of diffusing as a gas from the glove puncture to the hand and into a hand wound. The capability to produce hydrogen gas from metal-acid reactions should be avoided in a glove that can also produce a halogen gas. Hydrogen-halogen reactions may be dangerous and can rapidly consume the halogen gas.

A hand wound may be caused by a glove puncturing object or may already exist on a hand wearing the present invention. In either situation, it may be beneficial to treat the hand wound, the hand wound perimeter and the hand with an antiseptic composition by an automatic means without undue delay. Some embodiments of the present invention when worn on a hand can automatically help to provide a treatment of a non-liquid antiseptic composition to the hand and a hand wound near the glove puncture site without undue delay. The antiseptic can help to prevent contamination of the hand or hand wound with an infectious pathogen that may have preexisted on the glove-puncturing object.

In another embodiment of the present invention a glove in accordance with the present invention has at least two compartments in parallel to the glove wall, wherein at least one of the compartments parallel to the glove wall, called compartment One, contains a catalytic solution which comprises:

(a) about 0.1 to about 30 parts of a peroxide compound;
(b) about 1 to about 40 parts of deionized water;
(c) about 0.1 to about 10 parts of a multivalent cation complexation agent such as EDTA, HEDTA, EGTA or the like;
(d) about 0.05 to about 10 parts of a pH buffer to adjust the pH of the composition in compartment C pH to between pH 7 and 8 or to a pH range where a metal complexation agent is soluble;
(e) about 0.05 to 5 parts of a surface-active agent or detergent;

and wherein at least one of the other compartments, called compartment Two, that is parallel to the glove wall and to compartment One, contains an antiseptic composition which comprises:

(a) about 0.1 to about 50 parts of an antiseptic other than a peroxide;
(b) about 0.1 to about 95 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight; and
(e) about 0.1 to about 90 parts of an alcohol, the alcohol selected from the group consisting of ethanol, isopropanol, propanol, n-butanol, sec-butanol, tert-butanol, benzyl alcohol, methanol, stearyl alcohol, cetyl alcohol, and mixtures thereof;
(f) about 0.05 to about 10 parts of a surface-active agent or a detergent;
(g) about 0.1 to about 20 parts of a peroxide catalyst such as a powdered catalytic metal or a catalytic metal compound such as a metal oxide like for example maganese dioxide; useful becuase the peroxide catalyst is capable of releasing oxygen gas from a peroxide compound;
(h) optionally about 1 to 25 parts of an organic acid, a mineral acid, or a buffered mixture of relatively acidic salts or a mixture thereof, useful to inactivate the cation complexation agent which may be present when the some of the contents from compartments One and Two mix together during glove puncture;

and wherein contact between the substances of compartment One and Two can provide a mixture, the mixture capable of forming an expanding non-liquid antiseptic composition capable of some self-expulsion from the glove wall puncture and some transfer onto the hand or into a hand wound should a wound be caused by the object.

The substances used in compartment One can be mixed together at room temperature and poured into compartment One which should then be suitably sealed to prevent its leakage.

To make the composition for compartment Two, the two polyoxyethylene glycols can be heated in a glass beaker on a steam bath to about 65° C. The other ingredients and antiseptic(s) can then be added with mixing, previously dissolved in the water and at a temperature of 65° C. While the mixture is still liquified, compartment Two should be filled. At the same time or after cooling to room temperature, compartment Two should be sealed to prevent its leakage.

Contact between the compartment One and compartment Two compositions during glove manufacture must be avoided to avoid premature formation of an expanding non-liquid antiseptic composition. The capability to produce hydrogen gas from metal-acid reactions should be avoided in a glove that is also capable of producing a halogen to avoid hydrogen-halogen reactions.

In another embodiment of the present invention a glove in accordance with the present invention contains a non-liquid antiseptic composition which comprises:
(a) about 0.1 to about 50 parts of an antiseptic;
(b) about 0.1 to about 95 parts of water;
(c) about 0.05 to about 30 parts of a polyoxyethylene glycol of between about 150 to about 1540 molecular weight;
(d) about 0.05 to about 30 parts of a polyoxyethylene glycol of between about 1540 to about 6000 molecular weight; and
(e) about 0.1 to about 90 parts of an alcohol and mixtures thereof.

To make the above antiseptic composition, the two polyoxyethylene glycols can be heated in a glass beaker on a steam bath to about 65° C. The other ingredients and antiseptic can then be added with mixing, having been previously dissolved in the water at a temperature of 65° C. About one to twenty parts of the 65° C. liquified antiseptic composition can be combined with about one to thirty parts of a liquified glove wall structural composition. Preferably the structural wall composition and the antiseptic composition are selected to form a composite mixture in which the non-liquid antiseptic composition and the structural wall composition are poorly soluble within each other. Structural wall materials may be comprised of one or mope of the following: rubber materials, plastic materials, plant materials, mineral materials, and/or animal materials.

Before a mixture of wall structural elements and antiseptic composition is permited to cool and become semi-solid, some properties of the eventual glove wall subcompartments storing the non-liquid antiseptic composition can be varied; their heterogeneity, their volume, and the degree of their interconnections of the subcompartments can be varied by adjusting the agitation, the viscosity, and the ambient pressure of the mixture. Increasing the agitation of the mixture can be used to shear subcompartments into smaller volumes and alter their interconnections. Addition of a viscosity modifying substance or using less liquids with the solids in the composite mixture can be used to increase the viscosity of the mixture and tends to stabilize the subcompartmentation and interconnections between subcompartments. A glove in accordance with the present invention can be made for example by first making a thin rubber or thin plastic glove on a hand mold. Then this inner glove wall is coated by any means with a layer of the composite mixture of antiseptic composition and structural wall composition while it is still warm or liquified. Increased pressure can be used to reduce the size of the compartments and reduce air bubble size in the composite mixture layer until the layer has cooled or congealed or until the structural materials in the mixture have attained their final solid form. The solidified layer of composite mixture may comprise a porous spongy layer of non-liquid antiseptic composition. The porous exterior of the spongy layer of the glove is preferably sealed so that it is liquid-impermeable by applying a thin film of a rubber, plastic or combination of structural materials over the glove exterior by spraycoating, by dipping or by other means.

In another embodiment of the present invention a glove in accordance with the present invention contains a non-liquid antiseptic composition which comprises:
(a) about 0.1 to about 50 parts of an antiseptic; and
(b) about 0.1 to about 50 parts of petrolatum jelly.

The above non-liquid antiseptic composition can be formulated in a number of ways:
(a) the antiseptic can be dispersed as an insoluble suspension in the petrolatum jelly;
(b) the antiseptic can be dissolved in petrolatum jelly;
(c) the antiseptic can be dissolved in a substance which can be dissolved in the petrolatum jelly; or
(d) the antiseptic can be dissolved in a substance which is insoluble in the petrolatum jelly;
(d) the antiseptic can be dissolved in a substance which can form a simple water-oil emulsion, a simple oil-water emulsion, or a complex multiple phase emulsion which is then mixed to form a non-liquid with the petrolatum jelly;
(e) or mixtures thereof.

In another embodiment of the present invention a glove in accordance with the present invention contains a non-liquid antiseptic composition which comprises:
(a) about 0.1 to about 50 parts of an antiseptic; and
(b) about 0.1 to about 50 parts of a non-liquid medium which comprises: one or more materials or substances capable of forming a hydrated gel, an organic solvent hydrated gel, another gel, a foam, a paste, an ointment, a grease, a putty, a viscous cream, a viscous oil-water emulsion, a viscous water-oil emulsion, a multiphasic emulsion, another non-liquid medium, or mixtures thereof.

The above non-liquid antiseptic composition can be formulated in a number of ways in the non-liquid medium:
(a) the antiseptic can be dispersed as an insoluble suspension in the non-liquid medium; or
(b) the antiseptic can be dissolved in the non-liquid medium; or
(c) the antiseptic can be dissolved in a substance which is then dissolved in the non-liquid medium; or
(d) the antiseptic can be dissolved in a substance which is insoluble in the non-liquid medium; or
(e) or mixtures thereof can be formulated; or
(f) the antiseptic composition of (a), (b), (c), (d) or (e) can be capable of being combined with a gas provided by the glove as a result of a glove wall puncture, the gas-liquid or gas-liquid-solid emulsion capable of providing a foam or a viscous non-liquid composition.

In general, no particular order or method of producing the above non-liquid antiseptic composition is necessary.

The preferred embodiment (See Example 1 below) of the present invention is a flexible protective glove which comprises: an inner layer 3 of polyethylene plastic which is about 1 mil in thickness; an outer layer 2 of neoprene rubber which is about 4 mils in thickness; and a compartment 4 containing by volume approximately 10 milliliters of a non-liquid gelatinous antiseptic composition comprising: 30 parts of elemental iodine, 30 parts of potassium iodide, 50 parts of ethanol, 50 parts of distilled sterile water, 0.01 parts of FD&C red dye No. 40 (#40), 60 parts of polyoxyethylene glycol of about 1540 grams per mole molecular weight, 60 parts of polyethylene glycol of about 4000 grams per mole molecular weight, 30 parts of glycerin, and 10 parts of stearyl alcohol; wherein compartment 4 has a preferred thickness ranging between about 1 mil (one-thousandth of an inch) to about 250 mils and is closed to prevent evaporation. Note here that the term "parts" is a measure used in the present invention that means a measure of parts by weight and not a parts by volume.

The following Examples illustrate the present invention.

EXAMPLE 1

Example 1 describes how the preferred embodiment of the present invention is made. 60 grams of polyethylene glycol 1540 molecular weight (PEG 1540) and 60 grams of polyethylene glycol 4000 molecular weight (PEG 4000) are heated to 65° C. in a glass beaker A sitting in a hot water bath until the PEG 1540 and PEG 4000 has melted and are evenly mixed. 50 grams of ethanol, 80 grams of glycerin, 10 grams of stearyl alcohol and 50 grams of distilled sterile water, 30 grams of elemental iodine, 80 grams of potassium iodide, and 10 milligrams of FD&C Red Dye #40 are mixed in a second glass beaker B heated at 65° C. in a water bath until the mixture appears homogeneous. The contents of beaker A and beaker B are combined and then the hot antiseptic composition is stirred for 120 minutes while maintaining the temperature of the composition at 65° C. The stirring rate is adjusted to minimize the addition of air into the mixture. An inner glove layer of 1 mil thick polyethylene plastic (second material) is formed and cured until dry on a first hand mold. A slightly larger outer glove layer of 4 mil thick white neoprene rubber (first material) is formed and cured until dry on a second hand mold. The interior surface of the rubber outer glove layer is evenly coated with about 9 milliliters of the warm liquified antiseptic composition. While it is still warm, the outer glove layer is then slipped over the inner glove layer on the first hand mold. The glove is then allowed to cool to 23° C. during which time the antiseptic composition between the glove layer can gel. The end of compartment 4 of the glove is then sealed using a silicone containing glue (Archer Brand Silicone Rubber Cement, Radio Shack, Fort Worth, Tex., 76102) containing methyltriacetoxy-silane (CAS 004253343), ethyltriacetoxy-silane (CAS 017689779), polydimethylsiloxane, and silica (CAS 007631869).

EXAMPLE 2

200 grams of stearyl alcohol and 200 grams of petrolatum are heated in a glass beaker on a steam bath to melt them. To a second glass beaker on a steam bath, 1.3 grams of methylparaben, 0.8 grams of propylparaben, 10 grams of lauryl sulfate, 70 grams of propylene glycol, 120 grams of distilled sterile water, 120 grams of ethanol and 25 grams of povidone-iodine are added and mixed until the solution appears to have become well mixed at about 70° C. The contents of the second beaker are then added gradually to the first beaker while mixing well to make the antiseptic composition. An inner glove layer of 5 mil thick polyethylene plastic (second material) is formed and cured until dry on a first hand mold. A slightly larger outer glove layer of 5 mil thick white neoprene rubber (first material) is formed and cured until dry on a second hand mold, and then is evenly filled with the about 10 milliliters of the hot liquified antiseptic composition. The outer glove layer is then slipped over the inner glove layer on the first hand mold. After the glove has cooled to room temperature and the antiseptic composition has gelled, the end of compartment 4 of the glove is sealed using a silicone containing glue mixture.

REMAINING EXAMPLES

Note: For the remaining Examples, similar methods and quantities of materials are used to combine the substances in the formulation of the non-liquid antiseptic composition unless specified further or otherwise in each Example. Each non-liquid antiseptic composition in a hot liquified state is put in a compartment in a glove in accordance with the glove design of Example 1 of the present invention, unless specified further in each Example. If a dye is used in an Example then the dye is FD&C #40 unless specified.

EXAMPLE 3

The gloves for Example 3 use a portion of a non-liquid antiseptic composition containing 90 grams of povidone-iodine, 405 grams of distilled sterile water and 45 grams of isopropyl alcohol which is suspended in 130 grams of polyoxyethylene glycol 1540 molecular weight and 120 grams of polyoxyethylene glycol 4000 molecular weight to form a gel.

EXAMPLE 4

The gloves for Example 4 are elongated in length compared to the other Glove Examples of the present invention from a length of 12 inches to a length of 30 inches) to include a protective arm portion that could be extended to the shoulder and arm pit. The non-liquid antiseptic composition contain 50 grams of elemental iodine, 50 grams of sodium iodide, 80 grams of distilled sterile water, 100 grams of polyoxyethylene glycol 1540 molecular weight, 100 grams of polyoxyethylene glycol 4000 molecular weight, 270 grams of isopropanol. The antiseptic composition is kept at 60° C. until added to the glove compartment. An inner glove layer of 5 mil thick polyethylene plastic (second material) is formed and cured until dry on a long-armed first hand mold. A slightly larger outer glove layer of 8 mil thick white neoprene rubber (first material) is formed and cured until dry on a long-armed second hand mold, and is then evenly filled with the about 100 milliliters of the hot antiseptic composition. The outer glove layer is then slipped over the inner glove layer on the first hand mold and the temperature of the antiseptic composition is allowed to cool so that the composition gels. The shoulder arm end of compartment 4 of the glove is then sealed using a silicone containing glue.

EXAMPLE 5

The gloves for Example 5 are made using a non-liquid antiseptic composition containing 30 grams of elemental iodine, 30 grams of sodium iodide, 50 grams of distilled sterile water, 60 grams of polyoxyethylene glycol 1540 molecular weight, 60 grams of polyoxyethylene glycol 4000 molecular weight, 0.01 grams of FD&C red dye No. 40, and 50 grams of ethanol. An inner glove layer of 4 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 6

The gloves for Example 6 are made using a non-liquid antiseptic composition containing 20 grams of povidone-iodine, 45 grams of distilled sterile water, 15 grams of cholesterol, 15 grams of stearyl alcohol, 50 grams of white wax, 750 grams of petrolatum, 0.01 grams of FD&C red dye No. 40, and 150 grams of cetyl alcohol, and 10 milligrams of bradykinin. An inner glove layer of 4 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 7

The gloves for Example 7 are made using a non-liquid antiseptic composition containing 6.0 grams of sodium hypochlorite, 45 grams of cetyl alcohol, 10 grams of white wax, 15 grams of propylene glycol, 2 grams of sodium lauryl sulfate, 40 grams of distilled sterile water, 0.01 grams of FD&C red dye No. 40, and 0.5 grams of titanium dioxide. An inner glove layer of 4 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to liquid state. The outer glove layer is then slipped over the inner glove layer on the first hand mold, and after the antiseptic composition gels, the end of compartment 4 of the glove is sealed using a silicone containing glue.

EXAMPLE 8

The gloves for Example 8 are made using a non-liquid antiseptic composition containing 6.0 grams of potassium hypochlorite, 35 grams of cetyl alcohol, 20 grams of mineral oil, 25 grams of petrolatum, 4 grams of sodium lauryl sulfate, 20 grams of distilled sterile water, 0.01 grams of FD&C red dye No. 40, and 1 gram of titanium dioxide. An inner glove layer of 1 mil thick polyethylene plastic (second material) is formed and cured until dry on a first hand mold. A slightly larger outer glove layer of 5 mil thick white neoprene rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 9

The gloves for Example 9 are made using a non-liquid antiseptic composition containing 30 grams of potassium iodide, 30 grams of elemental iodide, 90 grams of distilled sterile water, 60 grams of polyoxyethylene glycol 1540, 60 grams of polyoxyethylene glycol 4000, 45 grams of 1,2,6-hexanetriol, 40 grams of isopropanol, 0.01 grams of FD&C red dye No. 40, and 0.5 grams of titanium dioxide. An inner glove layer of 1 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 10

The gloves for Example 10 are made using a non-liquid antiseptic composition containing 10 grams of povidone-iodine, 45 grams of distilled sterile water, 25 grams of glycerol monostearate, 50 grams of glycerin, 5 grams of bentonite, 45 grams of ethanol, 0.01 grams of FD&C red dye No. 40, and 0.5 grams of titanium dioxide. An inner glove layer of 1 mil thick polyethylene plastic (second material) is formed and cured until dry on a first hand mold. A slightly larger outer glove layer of 3 mil thick white polyethylene plastic (first material). is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 11

The gloves for Example 11 are made using a non-liquid antiseptic composition containing 10 grams of povidone-iodine, 45 grams of distilled sterile water, 2 grams of methylcellulose, 2 grams of Carbopol 934, 1 gram of methylparaben, 10 grams of propylene glycol, 0.01 grams of FD&C red dye No. 40, and 0.5 grams of titanium dioxide. An inner glove layer of 1 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 12

The gloves for Example 12 are made using a non-liquid antiseptic composition containing 10 grams of povidone-iodine, 45 grams of distilled sterile water, 2 grams of hydroxypropylmethylcellulose, 2 grams of Carbopol 934, 1 gram of methylparaben, 10 grams of propylene glycol, 0.01 grams of FD&C red dye No. 40, and 0.5 grams of titanium dioxide. An inner glove layer of 1 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 13

The gloves for Example 13 are made using a non-liquid antiseptic composition containing 20 grams of povidone-iodine, 10 grams of distilled sterile water, 30 grams of polyoxyethylene glycol of 1540 molecular weight, 35 grams of polyoxyethylene glycol of 4000 molecular weight, 45 grams of stearyl alcohol, 0.01 grams of FD&C red dye No. 40, and 0.5 grams of titanium dioxide. An inner glove layer of 1 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 14

The gloves for Example 14 are made using a non-liquid antiseptic composition containing 25 grams of iodine, 30 grams of polyoxyethylene glycol of 1540 molecular weight, 30 grams of polyoxyethylene glycol of 4000 molecular weight, 25 grams of polyethylene glycol 400 monostearate, 0.01 grams of FD&C red dye No. 40, and 0.5 grams of titanium dioxide. An inner glove layer of 1 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 15

The gloves for Example 15 are made using a non-liquid antiseptic composition containing 25 grams of 20 percent strength aqueous hydrogen peroxide, 0.1 grams of calcium citrate, 5 grams of sodium alginate, 0.5 grams of methylparaben, 30 grams of glycerin, 15 grams of distilled sterile water, 5 grams of isopropanol, 0.01 grams of FD&C red dye No. 40, and 0.5 grams of titanium dioxide. An inner glove layer of 3 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment & of the glove is sealed using a silicone containing glue.

EXAMPLE 16

The gloves for Example 18 are made using a non-liquid antiseptic composition containing 25 grams of sodium hypochlorite, 45 grams of distilled sterile water, 25 grams of polyoxyethylene glycol of 400 molecular weight, 25 grams of polyoxyethylene glycol of 6000 molecular weight, 10 grams of n-butanol, 30 grams of ethanol, 0.01 grams of FD&C red dye No. 40, and 0.5 grams of titanium dioxide. An inner glove layer of 3 mil thick polyethylene plastic (second material) is formed and cured until dry on a first hand mold. A slightly larger outer glove layer of 4 mil thick white neoprene rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 17

The gloves for Example 17 are made using a non-liquid antiseptic composition containing 25 grams of chlorhexidine gluconate, 45 grams of distilled sterile water, 15 grams of polyoxyethylene glycol of 1540 molecular weight, 15 grams of polyoxyethylene glycol of 4000 molecular weight, 30 grams of benzyl alcohol, 0.01 grams of FD&C red dye No. 40, and 0.5 grams of titanium dioxide. An inner glove layer of 3 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 18

The gloves for Example 18 are made using a non-liquid antiseptic composition containing 10 grams of dry powdered chlorhexidine gluconate mixed with 1 gram of dry powdered gum arabic and 1 gram of dry powdered potassium chloride. An inner glove layer of 1 mil thick polyethylene plastic (second material) is formed and cured until dry on a first hand mold. A thin elastic hand glove made of a fine nylon stocking mesh (comparable in thickness to a sheer woman's leg stocking) is placed over the innner glove on the hand mold. The pores of the nylon stocking are loaded with about 8 grams of the dry powdered antiseptic composition and serve as subcompartments for the antiseptic composition. A slightly larger outer glove layer of 4 mil thick white latex rubber (first material) is formed and cured until dry on a second hand mold, and then is slipped over the powdered antiseptic composition-loaded nylon mesh glove on the first hand mold.

EXAMPLE 19

The gloves for Example 19 are made using a non-liquid antiseptic composition containing 25 grams of chlorhexidine gluconate, 15 grams of yellow wax, 17 grams of wool fat, 40 grams of petrolatum, 22 grams of glycerin, 15 grams of distilled sterile water, 30 grams of ethanol, 0.01 grams of FD&C red dye No. 40, and 0.5 grams of zinc sulfate. An inner glove layer of 3 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 20

The gloves for Example 20 are made using a non-liquid antiseptic composition containing 25 grams of nonoxynol-9, 10 grams of cholesterol, 10 grams of stearyl alcohol, 25 grams of white wax, and 300 grams of white petrolatum. An inner glove layer of 3 mil thick polyethylene plastic (second material) is formed and cured until dry on a first hand mold. A slightly larger outer glove layer of 4 mil vinyl plastic (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 21

The gloves for Example 21 are made using a non-liquid antiseptic composition containing 25 grams of sodium dichloroisocyanurate, 10 grams of cholesterol, 10 grams of stearyl alcohol, 25 grams of white wax, and 300 grams of white petrolatum. An inner glove layer of 3 mil thick polyethylene plastic (second material) is formed and cured until dry on a first hand mold. A slightly larger outer glove layer of 2 mil thick saran plastic with a 3 mil thick coating of white latex rubber (first material composite) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 22

The gloves for Example 22 are made using a non-liquid antiseptic composition containing 25 grams of hexachlorophene, 5 grams of elemental iodine, 5 grams of creosote, 10 grams of pine oil NF, 5 grams of phenol, 5 grams of potassium hypochlorite, 0.25 grams of methyparaben, 10 grams of sodium lauryl sulfate, 80 grams of propylene glycol, 200 grams of stearyl alcohol, 250 grams of white petrolatum and 300 grams of distilled sterile water and 0.5 grams of peppermint oil. An inner glove layer of about 30 mils thick polyethylene plastic (second material) is formed and cured until dry on a first hand mold. A slightly larger outer glove layer of 40 mils thick white neoprene rubber (first material) is formed and cured until dry on a second hand mold, and then is evenly filled with the about 25 milliliters of the antiseptic composition in a hot liquified state. The outer glove layer is then slipped over the inner glove layer on the first hand mold and the glove is allowed to cool so that the composition gels. The end of compartment 4 of the glove is sealed using a silicone containing glue. The thicker glove layers of this embodiment of the present invention are designed to provide a strong physical barrier and still provide a glove with suitable flexiblity for some gloved workers: including for example law enforcement workers, prison workers, psychiatric hospital workers, sanitation workers, and the like workers whose hands do not generally need to perform delicate maual tasks. This glove design is not optimally worn by a person who would perform medical surgery, draw blood, or dental work where a thinner glove must be used.

EXAMPLE 23

The gloves for Example 23 are made using a non-liquid antiseptic composition containing 15 grams of sodium perborate NF, 15 grams of cetyl alcohol, 1 gram of white wax, 10 grams of propylene glycol, 2 grams of sodium lauryl sulfate, 10 grams of white petrolatum and 40 grams of distilled sterile water. An inner glove layer of 1 mil thick polyethylene plastic (second material) is formed and cured until dry on a first hand mold. A slightly larger outer glove layer of 5 mil thick white neoprene rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 24

The gloves for Example 24 are made using a non-liquid antiseptic composition containing 25 grams of potassium dichloroisocyanurate, 15 grams of cetyl alcohol, 1 gram of white wax, 10 grams of propylene glycol, 2 grams of sodium lauryl sulfate, 15 grams of mineral oil, and 50 grams of distilled sterile water. An inner glove layer of 3 mil thick polyethylene plastic (second material) is formed and cured until dry on a first hand mold. A slightly larger outer glove layer of 2 mil thick white polyethylene plastic (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 25

The gloves for Example 25 are made using a non-liquid antiseptic composition containing 5 grams of bacitracin, 5 grams of norfloxacin, and 2 grams of polymixin B sulfate, 10 grams of calcium carbonate, 10 grams of potassium bicarbonate, 15 grams of cetyl alcohol, 1 gram of white wax, 30 grams of white petrolatum, 5 grams of propylene glycol, 1 gram of menthol, I gram of sodium lauryl sulfate, and 55 grams of distilled sterile water. An inner glove layer of 2 mil thick polyethylene plastic (second material) is formed and cured until dry on a first hand mold. A slightly larger outer glove layer of 3 mil thick white polyethylene plastic (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 26

The gloves for Example 26 are made using a non-liquid antiseptic composition containing 55 grams of 37 percent by weight formaldehyde solution (Formalin solution), 20 grams of potassium iodide, 5 grams of stearyl alcohol, 5 grams of cetyl alcohol, 1 gram of white wax, 1.5 grams of sodium lauryl sulfate, 15 grams of white petrolatum and 15 grams of mineral oil. An inner glove layer of 3 mil thick polyethylene plastic (second material) is formed and cured until dry on a first hand mold. A slightly larger outer glove layer of 3 mil thick polyethylene plastic (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 27

The gloves for Example 27 are made using a non-liquid antiseptic composition containing 2 grams of potassium permanganate in 75 grams of distilled sterile water, 1 gram of white wax, and 55 grams of white petrolatum. An inner glove layer of 3 mil thick polyethylene plastic (second material) is formed and cured until dry on a first hand mold. A slightly larger outer glove layer of 1 mil thick polyethylene plastic coated with a 4 mil thick white latex rubber layer (first material composite) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 28

The gloves for Example 28 are made using a two compartment system whose partial mixture as a result of a glove wall puncture can increase the release of formaldehyde gas vapor from a glove puncture site. The two compartments are provided in parallel with the glove wall so that the glove puncturing object can cause some mixture formation from the two compartments to form a potent gaseous antiseptic that can readily diffuse to the hand and a hand wound should one occur, to provide an antiseptic treatment. The composition for the outer glove compartment contains 5 grams of 37 percent formaldehyde solution emulsified in 10 grams of white petrolatum with 0.01 grams of red iron oxide as a colorant. The composition for the inner compartment contains 0.5 grams of potassium permanganate dissolved in 10 grams of distilled sterile water that has been emulsified in 3 grams of decane dissolved in 5 grams of white petrolatum and 0.5 grams of white wax.

An inner glove layer of 2 mil thick polyethylene plastic (second material) is formed and cured until dry on a first hand mold. This is coated with about 8 grams of the permanganate emulsion composition while it is still warm and liquified. After this emulsion gels with cooling, the emulsion is spray coated with a 1.5 mil plastic film which is allowed to dry. This intermediate plastic film layer is then dip-coated with about 8 grams of the formaldehyde emulsion formulation while it is still warm and liquified. Over the gelled formaldehyde emulsion, an outer glove layer of 1 mil thick polyethylene plastic is spray-coated with a layer of 4 mil thick white latex rubber (first material) and allowed to harden. Care is taken not prevent contamination of the two compartments, and the ends of the inner and outer compartments of the glove are sealed using a silicone containing glue.

EXAMPLE 29

The gloves for Example 29 are made using a two compartment system whose partial mixture as a result of a glove wall puncture can produce small amounts of chlorine gas vapor from a glove puncture site. The two compartments are provided in parallel with the glove wall so that the glove puncturing object can cause some mixture formation from the two compartments to form a potent gaseous antiseptic that can readily diffuse to the hand and a hand wound should one occur, to provide an antiseptic treatment. The outer glove compartment contains 2 grams of concentrated hydrochloric acid solution emulsified in 10 grams of white petrolatum with 1 gram of ferric chloride as a colorant. The inner compartment contains 0.5 grams of potassium permanganate dissolved in 10 grams of distilled sterile water that has been emulsified in 3 grams of decane dissolved in 5 grams of white petrolatum and 0.5 grams of white wax.

An inner glove layer of 2 mil thick polyethylene plastic (second material) is formed and cured until dry on a first hand mold. This is coated with about 8 grams of the permanganate emulsion composition while it is still warm and liquified. After this emulsion gels with cooling, the emulsion is spray coated with a 0.5 mil plastic film which is allowed to dry. This intermediate plastic film layer is then dip-coated with about 8 grams of the formaldehyde emulsion formulation while it is still warm and liquified. An outer glove layer of 4 mil thick white neoprene rubber (first material) is spray-coated over the galled formaldehyde emulsion and allowed to harden. Care is taken not prevent contamination of the two compartments, and the ends of the inner and outer compartments of the glove are sealed using a silicone containing glue.

EXAMPLE 30

The gloves for Example 30 are made using a non-liquid antiseptic composition containing 25 grams of 20 percent hydrogen peroxide solution, 48 grams of polyoxyethylene glycol 400 molecular weight, 48 grams of polyoxyethylene glycol 4000 molecular weight, and 10 grams of stearyl alcohol. An inner glove layer of a 3 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 31

The gloves for Example 31 are made using a non-liquid antiseptic composition containing 25 grams of 20 percent hydrogen peroxide solution, 48 grams of polyoxyethylene glycol 400 molecular weight, 48 grams of polyoxyethylene glycol 1540 molecular weight, and 10 grams of stearyl alcohol. An inner glove layer of 0.3 mil thick polyethylene plastic (second material) is formed and cured until dry on a first hand mold. A slightly larger outer glove layer of 5 mil thick white neoprene rubber (first material) is formed and cured until dry on a second hand mold, and then is evenly filled with the about 6 milliliters of the antiseptic composition heated to a liquid state. The latex rubber whitener (colorant) is zinc oxide. The outer glove layer is then slipped over the inner glove layer on the first hand mold, and after the antiseptic composition gels, the end of compartment 4 of the glove is sealed using a silicone glue.

EXAMPLE 32

The gloves for Example 32 are made using a non-liquid antiseptic composition containing 10 grams of sodium hypochlorite, 15 grams of polyoxyethylene glycol 4000 molecular weight, 10 grams of cetyl alcohol, 10 grams of stearyl alcohol, 17 grams of glycerin, 0.7 grams of sodium lauryl sulfate, and 50 grams of distilled sterile water. An inner glove layer of 4 mil thick latex rubber (second material) is formed and cured until dry on a first hand mold. A slightly larger outer glove layer of 4 mil thick case-hardened black latex rubber (first material) is formed and cured until dry on a second hand mold, and then is evenly filled with the about 10 milliliters of the antiseptic composition heated to a liquid state. The black colorant is powdered sterile charcoal. The outer glove layer is then slipped over the inner glove layer on the first hand mold, and after the antiseptic composition gels, the end of compartment 4 of the glove is sealed using a silicone containing glue.

EXAMPLE 33

The gloves for Example 33 are made using a non-liquid antiseptic composition containing 10 grams of sodium hypochlorite, 40 grams of distilled sterile water, 32 grams of 1,2,6-hexanetriol, 47 grams of polyoxyethylene glycol 400 molecular weight, and 58 grams of polyoxyethylene glycol 4000. An inner glove layer of 0.6 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 34

The gloves for Example 34 are made using a non-liquid antiseptic composition containing 2 grams of elemental iodine, 3 grams of sodium iodide, 0.5 grams of iodoform, 10 grams of distilled sterile water, 1 gram of sorbitan monopalmitate, 40 grams of polyoxyethylene glycol 400 molecular weight, and 50 grams of polyoxyethylene glycol 4000. An inner glove layer of 2 mil thick polyethylene plastic (second material) is formed and cured until dry on a first hand mold. A slightly larger outer glove layer of 6 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 35

The gloves for Example 35 are made using a non-liquid antiseptic composition containing 8 grams of nonoxynol-9, 5 grams of octoxynol, 2 grams of sodium tetradecyl sulfate, 24 grams of distilled sterile water, 4 grams of sorbitan monopalmitate, 40 grams of polyoxyethylene glycol 400 molecular weight, 40 grams of polyoxyethylene glycol 4000 and 10 grams of glycerin. An inner glove layer of 1 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 36

The gloves for Example 36 are made using a non-liquid antiseptic composition containing 15 grams of 50% by weight concentrated trichloroacetic acid, 10 grams of cholesterol, 10 grams of stearyl alcohol, 25 grams of white wax, and 300 grams of white petrolatum. An inner glove layer of 3 mil thick polyethylene plastic (second material) is formed and cured until dry on a first hand mold. A slightly larger outer glove layer of 4 mil thick white neoprene rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 37

The gloves for Example 37 are made using a non-liquid antiseptic composition containing 5 grams of eucalyptus oil, 4 grams of phenyl salicylate, 3 grams of pine oil NF, 5 grams of povidone-iodine, and 3 grams of o-phenylphenol, 10 grams of cholesterol, 10 grams of stearyl alcohol, 25 grams of white wax, and 300 grams of white petrolatum. An inner glove layer of 3 mil thick polyethylene plastic (second material) is formed and cured until dry on a first hand mold. A slightly larger outer glove layer of 5 mil thick neoprene latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 38

The gloves for Example 38 are made using a non-liquid antiseptic composition containing 10 grams of poloxamer 188, and 10 grams of cetylpyridinium chloride, 50 grams of distilled sterile water, 10 grams of cetyl alcohol, 5 grams of glycerin, 40 grams of polyoxyethylene glycol 400 molecular weight and 38 grams of polyoxyethylene glycol 4000 molecular weight. An inner glove layer of 2 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 39

The gloves for Example 39 are made using a non-liquid antiseptic composition containing 22 grams of methylbenzethonium chloride, 50 grams of distilled sterile water, 10 grams of cetyl alcohol, 5 grams of glycerin, 40 grams of polyoxyethylene glycol 400 molecular weight and 38 grams of polyoxyethylene glycol 4000 molecular weight. An inner glove layer of 2 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 40

The gloves for Example 40 are made using a two compartment system whose partial mixture as a result of a glove wall puncture can increase the release of glutaraldehyde gas vapor from a glove puncture site. The two compartments are provided in parallel with the glove wall so that the glove puncturing object can cause some mixture formation from the two compartments to form a potent gaseous antiseptic that can readily diffuse to the hand and a hand wound should one occur, to provide an antiseptic treatment. The outer glove compartment contains 5 grams of 25 percent glutaraldehyde solution emulsified in 10 grams of white petrolatum with 0.01 grams of red iron oxide as a colorant. The inner compartment contains 0.5 grams of potassium permanganate dissolved in 10 grams of distilled sterile water that has been emulsified in 3 grams of decane dissolved in 5 grams of white petrolatum and 0.5 grams of white wax.

An inner glove layer of 3 mil thick polyethylene plastic (second material) is formed and cured until dry on a first hand mold. This is coated with about 8 grams of the permanganate emulsion composition while it is still warm and liquified. After this emulsion gels with cooling, the emulsion is spray coated with a 0.5 mil plastic film which is allowed to dry. This intermediate plastic film layer is then dip-coated with about 8 grams of the glutaraldehyde emulsion formulation while it is still warm and liquified. An outer glove layer of 4 mil thick white neoprene rubber (first material) is spray-coated over the gelled glutaraldehyde emulsion and allowed to harden. Care is taken not prevent contamination of the two compartments, and the ends of the inner and outer compartments of the glove are sealed using a silicone containing glue.

EXAMPLE 41

The gloves for Example 41 are made using a two compartment system whose partial mixture as a result of a glove wall puncture can produce carbon dioxide gas bubbles in the mixture which helps to expand the mixture which comprises the non-liquid antiseptic composition from the glove puncture site. The two compartments are provided in parallel with the glove wall so that the glove puncturing object can cause some mixture formation from the two compartments. The outer glove compartment contains 1 gram of elemental iodine, 5 grams of potassium iodide, 1 gram of peppermint oil, and 5 grams of 50% concentrated hydrochloric acid emulsified in 10 grams of white petrolatum, 2 grams of red iron oxide, and 5 grams of glycerin. The inner compartment contains 5 grams of sodium bicarbonate dissolved in 10 grams of distilled sterile water that has been emulsified in 5 grams of white petrolatum, 0.5 grams of white wax and 5 grams of polyoxyethylene glycol 400 molecular weight.

An inner glove layer of 0.3 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 4 mil thick white latex rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 42

The gloves for Example 42 are made using a two compartment system whose partial mixture as a result of a glove wall puncture can produce carbon dioxide gas bubbles in the mixture which helps to expand the mixture which comprises the non-liquid antiseptic composition from the glove puncture site. The two compartments are provided in parallel with the glove wall so that the glove puncturing object can cause some mixture formation from the two compartments. The composition for the outer glove compartment contains 1 gram of elemental iodine, 5 grams of potassium iodide, and 5 grams of 50% concentrated hydrochloric acid emulsified in 10 grams of white petrolatum and 5 grams of glycerin. The composition for the inner compartment contains 5 grams of calcium carbonate dissolved in 10 grams of distilled sterile water that has been emulsified in 5 grams of white petrolatum, 0.5 grams of white wax and 5 grams of polyoxyethylene glycol 400 molecular weight.

An inner glove layer of 0.3 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 4 mil thick white latex rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 43

The gloves for Example 43 are made using a two compartment system whose partial mixture as a result of a glove wall puncture can produce carbon dioxide gas bubbles in the mixture which helps to expand the mixture which comprises the non-liquid antiseptic composition from the glove puncture site. The two compartments are provided in parallel with the glove wall so that the glove puncturing object can cause some mixture formation from the two compartments. The composition for the outer glove compartment contains 8 grams of nonoxynol-9, and 5 grams of 50% concentrated trichloroacetic acid emulsified in 10 grams of white petrolatum and 5 grams of propylene glycol. The composition for the inner compartment contains 5 grams of sodium bicarbonate dissolved in 10 grams of distilled sterile water that has been emulsified in 5 grams of white petrolatum, 0.5 grams of white wax and 5 grams of polyoxyethylene glycol 400 molecular weight.

An inner glove layer of 0.3 mil thick polyethylene plastic (second material)is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 4 mil thick white neoprene rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 44

The gloves for Example 44 are made using a two compartment system whose partial mixture as a result of a glove wall puncture can produce carbon dioxide gas bubbles in the mixture which helps to expand the mixture which comprises the non-liquid antiseptic composition from the glove puncture site. The two compartments are provided in parallel with the glove wall so that the glove puncturing object can cause some mixture formation from the two compartments. The composition for the outer glove compartment contains 10 grams of chlorhexidine hydrochloride, and 5 grams of 50% concentrated hydrochloric acid emulsified in 7 grams of white petrolatum and 5 grams of propylene glycol. The composition for the inner compartment contains 5 grams of sodium bicarbonate dissolved in 10 grams of distilled sterile water that has been emulsified in 6 grams of white petrolatum, and 5 grams of polyoxyethylene glycol 400 molecular weight.

An inner glove layer of 0.3 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 4 mil thick white latex rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 45

The gloves for Example 45 are made using a two compartment system whose partial mixture as a result of a glove wall puncture can produce carbon dioxide gas bubbles in the mixture which helps to expand the mixture which comprises the non-liquid antiseptic composition from the glove puncture site. The two compartments are provided in parallel with the glove wall so that the glove puncturing object can cause some mixture formation from the two compartments. The composition for the outer glove compartment contains 10 grams of povidone-iodine, and 5 grams of 50% concentrated hydrochloric acid emulsified in 7 grams of white petrolatum and 5 grams of glycerin. The composition for the inner compartment contains 5 grams of sodium bicarbonate dissolved in 10 grams of distilled sterile water that has been emulsified in 6 grams of white petrolatum, and 5 grams of polyoxyethylene glycol 400 molecular weight.

An inner glove layer of 0.3 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 4 mil thick white neoprene rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 46

The gloves for Example 46 are made using a two compartment system whose partial mixture as a result of a glove wall puncture can produce carbon dioxide gas bubbles in the mixture which helps to expand the non-liquid antiseptic composition mixture, partially in the form of a foam and partially in the form of a viscous cream base, from the glove puncture site. The two compartments are provided in parallel with the glove wall so that the glove puncturing object can cause some mixture formation from the two compartments. The composition for the outer glove compartment contains 25 grams of methanol, and 15 grams of 50% concentrated hydrochloric acid emulsified in 12 grams of white petrolatum and 5 grams of glycerin. The composition for the inner compartment contains 5 grams of sodium bicarbonate dissolved in 10 grams of distilled sterile water that has been emulsified in 6 grams of white petrolatum, and 5 grams of polyoxyethylene glycol 400 molecular weight.

An inner glove layer of 1 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 5 mil thick white neoprene rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 47

The gloves for Example 47 are made using a two compartment system whose partial mixture as a result of a glove wall puncture can produce carbon dioxide gas bubbles in the mixture which helps to expand the non-liquid antiseptic composition mixture, partially in the form of a foam and partially in the form of a viscous cream base, from the glove puncture site. The two compartments are provided in parallel with the glove wall so that the glove puncturing object can cause some mixture formation from the two compartments. The composition for the outer glove compartment contains 15 grams of 50% concentrated hydrochloric acid emulsified in 12 grams of white petrolatum and 5 grams of glycerin. The composition for the inner compartment contains 15 grams of sodium hypochlorite and 5 grams of sodium bicarbonate dissolved in 10 grams of distilled sterile water that has been emulsified in 6 grams of white petrolatum, and 5 grams of polyoxyethylene glycol 400 molecular weight.

An inner glove layer of 1 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. Over the gelled acidic emulsion an outer glove layer of 2 mil thick polyethylene plastic is then spray-coated with a 3 mil thick layer of white latex rubber (first material composite) and allowed to harden. Care is taken not prevent contamination of the two compartments, and the ends of the inner and outer compartments of the glove are sealed using a silicone containing glue.

EXAMPLE 48

The gloves for Example 48 are made using a two compartment system whose partial mixture as a result of a glove wall puncture can produce oxygen gas bubbles in the mixture which helps to expand the non-liquid antiseptic composition mixture, partially in the form of a foam and partially in the form of a viscous cream base, from the glove puncture site. The two compartments are provided in parallel with the glove wall so that the glove puncturing object can cause some mixture formation from the two compartments. The composition for the outer glove compartment contains 15 grams of 20% hydrogen peroxide solution emulsified in 12 grams of white petrolatum and 5 grams of glycerin. The composition for the inner compartment contains 2 grams of finely dispersed catalytic manganese dioxide powder in 20 grams of distilled sterile water that has been emulsified in 6 grams of white petrolatum, and 5 grams of polyoxyethylene glycol 400 molecular weight.

An inner glove layer of 1 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 5 mil thick white neoprene rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 49

The gloves for Example 49 are made using a two compartment system whose partial mixture as a result of a glove wall puncture can produce some carbon dioxide gas bubbles in the mixture which helps to expand the non-liquid antiseptic composition mixture, partially in the form of a foam and partially in the form of a viscous cream base, from the glove puncture site. The two compartments are provided in parallel with the glove wall so that the glove puncturing object can cause some mixture formation from the two compartments. The composition for the outer glove compartment contains 15 grams of 50% concentrated hydrochloric acid emulsified in 12 grams of white petrolatum and 5 grams of glycerin. The composition for the inner compartment contains 15 grams of sodium iodide, 5 grams of sodium bicarbonate, and 2 grams of finely dispersed catalytic manganese dioxide powder in 25 grams of distilled sterile water that has been emulsified in 6 grams of white petrolatum, and 5 grams of polyoxyethylene glycol 400 molecular weight.

An inner glove layer of 1 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 5 mil thick white neoprene rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 50

The gloves for Example 50 are made using a two compartment system whose partial mixture as a result of a glove wall puncture can produce oxygen gas bubbles in the mixture which helps to expand the non-liquid antiseptic composition mixture, partially in the form of a foam and partially in the form of a viscous cream base, from the glove puncture site. The two compartments are provided in parallel with the glove wall so that the glove puncturing object can cause some mixture formation from the two compartments. The composition for the outer glove compartment contains 15 grams of 20% benzoyl peroxide solution emulsified in 12 grams of white petrolatum and 5 grams of glycerin. The composition for the inner compartment contains 2 grams of finely dispersed catalytic manganese dioxide powder in 20 grams of distilled sterile water that has been emulsified in 6 grams of white petrolatum, and 5 grams of polyoxyethylene glycol 400 molecular weight.

An inner glove layer of 1 mil thick polyethylene plastic (second material) is formed and cured until dry on a first hand mold. This is coated with about 8 grams of the bicarbonate-containing emulsion composition while it is still warm and liquified. After this emulsion gels with cooling, the emulsion is spray coated with a 0.5 mil plastic film which is allowed to dry. This intermediate plastic film layer is then dip-coated with about 8 grams of the acidic emulsion formulation while it is still warm and liquified. An outer glove layer of 5 mil thick white neoprene rubber (first material) is spray-coated over the gelled acidic emulsion and allowed to harden. Care is taken not prevent contamination of the two compartments, and the ends of the inner and outer compartments of the glove are sealed using a silicone containing glue.

EXAMPLE 51

The gloves for Example 51 are made using a non-liquid antiseptic composition containing 10 grams of benzoyl peroxide, 40 grams of distilled sterile water, 32 grams of 1,2,6-hexanetriol, 47 grams of polyoxyethylene glycol 400 molecular weight, and 58 grams of polyoxyethylene glycol 4000. An inner glove layer of 0.6 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 52

The gloves for Example 52 are made using a non-liquid antiseptic composition containing 10 grams of zinc peroxide, 20 grams of 70% by volume isopropanol in distilled sterile water, 32 grams of 1,2,6-hexanetriol, 47 grams of polyoxyethylene glycol 400 molecular weight, and 58 grams of polyoxyethylene glycol 4000. An inner glove layer of 2 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 53

The gloves for Example 53 are made using a non-liquid antiseptic composition containing 10 grams of hydrogen peroxide, 20 grams of ethanol, 32 grams of 1,2,6-hexanetriol, 47 grams of polyoxyethylene glycol 400 molecular weight, and 58 grams of polyoxyethylene Glycol 4000. An inner glove layer of 2 mil thick polyethylene plastic (second material) is formed and cured until dry on a first hand mold. A slightly larger outer glove layer of 5 mil thick white latex rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition Gels, the end of compartment 4 of the glove is sealed using a silicone containing glue.

EXAMPLE 54

The gloves for Example 54 are made using a non-liquid antiseptic composition containing 5 grams of chlorhexidine gluconate in 20 grams of isopropanol, 10 grams of distilled sterile water, 20 grams of glycerine, 42 grams of polyoxyethylene glycol 1540 molecular weight, and 5 grams of sodium oleate. An inner glove layer of 2 mil thick polyethylene plastic (second material) is formed and cured until dry on a first hand mold. A slightly larger outer glove layer of 2 mil thick white polyethylene plastic (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 55

The gloves for Example 55 are made using a non-liquid antiseptic composition containing 5 grams of elemental iodine, 5 grams of potassium iodide, 30 grams of isopropanol, 2 grams of 50 percent strength glacial acetic acid diluted by weight with distilled sterile water, 1 gram of sodium acetate, 25 grams of polyoxyethylene glycol 1540 molecular weight, 2 grams of cetyl alcohol, and 5 grams of propylene glycol. An inner glove layer of 0.6 mil thick polyethylene plastic (second material) is formed and cured until dry on a first hand mold. A slightly larger outer glove layer of 6 mil thick white neoprene rubber (first material) is formed and cured until dry on a second hand mold, and then is evenly filled with the about 10 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

EXAMPLE 56

The gloves for Example 56 are made using a non-liquid antiseptic composition containing 50 grams of denatured ethanol and 15 grams of polyoxyethylene glycol 1540 molecular weight. An inner glove layer of 1 mil thick polyethylene plastic (second material) is formed and cured until dry on a first hand mold. A slightly larger outer glove layer of 4 mil thick white latex rubber (first material) is formed and cured until dry on a second hand mold, and then is evenly filled with the about 6 milliliters of the antiseptic composition heated to a liquid state. The outer glove layer is then slipped over the inner glove layer on the first hand mold, and after the antiseptic composition gels, the end of compartment 4 of the glove is sealed using a silicone containing glue.

While we have shown and described a number of embodiments of our invention, it will be apparent to those skilled in the art that many changes and modifications may be made without departing from our present invention in its broader aspects. We therefore intend the appended claims to cover all such changes and modifications as fall within the true spirit and scope of our present invention.

We claim:

1. A flexible protective glove with a liquid-impermeable wall having the capability to provide a non-liquid antiseptic composition treatment to a hand and to a hand wound should the wound occur underneath the glove while the glove is being worn when a wall of the glove is punctured by an object that may be contaminated with an infectious pathogen, comprising:

(a) a glove wall with a liquid-impermeable outer layer comprised of a first material having a thickness of about 1 mil to about 40 mils and a liquid-impermeable less elastic inner layer composed of a second material having a thickness of about 0.3 mils to about 30 mils wherein the first material and the second material form the walls of a compartment capable of providing a non-liquid antiseptic composition;

(b) wherein the non-liquid antiseptic composition in the compartment comprises an antiseptic or a number of substances that can form the non-liquid antiseptic composition when the object punctures the glove wall and causes a combination of a portion of the substances, wherein at least a portion of the glove wall contains the non-liquid antiseptic composition when the glove wall is punctured by the object;

(c) the glove wall capable of providing a physical barrier as a means of protection to the hand while the glove is being worn by an individual until a portion of the glove wall is punctured by an object;

(d) the glove wall capable of being punctured by the object while the glove is being worn on the hand;

(e) the glove wall having the flexibility to allow the hand of an individual in need of wearing the glove to easily and adequately perform delicate, dexterous and complex work including the work performed by a surgeon, a medical doctor, a dentist, a laboratory worker, a health care worker, a law enforcement worker, and a hospital worker;

(f) the glove having the capability to provide a coating to at least a portion of the object puncturing the glove wall; the coating comprising the non-liquid antiseptic composition; the coating on the object providing a means for immediately transferring some of the non-liquid antiseptic composition onto the hand and into the hand wound by the object puncturing the glove wall while the glove is being worn; the non-liquid antiseptic composition transferred to the hand and to the hand wound having the capability to provide an immediate non-liquid antiseptic composition treatment to the hand and hand wound;

(g) the glove having the additional capability to transfer some of the non-liquid antiseptic composition from a section of the glove wall having a hole resulting from the object puncturing the glove wall; the hole in the inner glove layer is relatively larger than the hole in the outer glove layer and may be used to help to direct a relatively larger transfer of non-liquid antiseptic composition from the glove to the hand and to the hand wound than from the glove to the outer surface of the glove; and (h) the glove having the capability of treating the hand and the hand wound with the non-liquid antiseptic composition when the object punctures the glove wall, when the object contacts the hand, when the object may wound the hand, and when the object may contaminate the hand and the hand would with the infectious pathogen; wherein the non-liquid antiseptic composition transferred to the hand and the hand wound can help to protect the hand, the hand wound, and the systemic circulation of the individual by killing, inactivating, and otherwise destroying the infectious pathogen that may be contaminating the hand and the hand wound.

2. The glove according to claim 1, wherein the non-liquid antiseptic composition is capable of being redistributed within the compartment of the glove by massaging the glove to force the non-liquid antiseptic composition in the compartment to accumulate near the glove wall having the hole or is capable of being automatically or manually expelled from the wall having the hole onto the hand and into the hand wound providing additional non-liquid antiseptic composition to treat the skin and the hand wound resulting in additional protection of the skin and hand would from the infectious pathogen that may be contaminating the skin and the hand wound.

3. A glove according to claim 1, wherein the first material and the second material comprise:

a structural material selected from the group consisting of latex rubber, cis-1,4-polyisoprene, cis-polybutadiene, neoprene rubber, nitrile rubber, silicone rubber, case-hardened rubber, isobutylene-isoprene 1. butyl rubber, butadieneacrylonitrile 1. nitrile rubber, styrene-butadiene rubber, ethylene-propylene copolymer, ethylene-propylene diene terpolymer, polyisobutylene, chlorosulphonated polyeten, ester-type urethan rubber, polychlormethyloxyran epichlorhydrin rubber, epichlorhydrin copolymer with ethyleneoxydichlormethyloxyran copolymer cellulose acetate plastic, vinyl plastic, polyethylene plastic, polypropylene plastic, polyvinyl chloride plastic, polyvinyl acetate plastic, polystyrene plastic, polymethyl methyl-acrylate plastic, polyacrylonitrile plastic, vinyllite plastic, saran plastic, polytetrafluoroethylene plastic, polytrifluorochloroethylene plastic, polycaprolactam plastic, polyester plastic, urea formaldehyde plastic, polyurethane plastic, isotactic polypropylene plastic, nylon plastic, rayon plastic, polyamide plastic, phenolic plastic, silicone plastic, silk fiber, cotton fiber, cellulose fiber, wool fiber, animal skin, animal intestinal tissue, animal connective tissue, metallic fiber, mineral fiber and mixtures thereof.

4. A glove according to claim 3, wherein the first material comprises: a structural material selected from the group consisting of latex rubber, cis-1,4-polyisoprene rubber, cis-polybutadiene rubber, neoprene rubber, and nitrile rubber, silicone rubber case-hardened rubber, isobutylene-isoprene 1. butyl rubber, butadieneacrylonitrile 1. nitrile rubber, styrene-butadiene rubber, ethylene-propylene copolymer, ethylene-propylene diene terpolymer, polyisobutylene, chlorosulphonated polyeten, ester-type urethan rubber, polychlormethyloxyran epichlorhydrin rubber, epichlorhydrin copolymer with ethyleneoxydichlormethyloxyran copolymer, and mixtures thereof; and wherein the second material comprises: a structural material selected from the group consisting of cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polycaprolactam plastic, rayon plastic, polytrifluorochloroethylene plastic, nylon plastic, polyester plastic, urea formaldehyde plastic, polyurethane plastic, isostactic polypropylene plastic, polyamide plastic, phenolic plastic, silicone plastic, silk fiber, cotton fiber, plant fiber, wool fiber, animal skin, animal intestinal tissue, animal connective tissue, metallic fiber, mineral fiber, and mixtures thereof.

5. A glove according to claim 1, wherein the antiseptic is selected from the group consisting of chlorhexidine gluconate, chlorhexidine acetate, chlorhexidine hydrochloride, octoxynol, nonoxynol-9, methanol, ethanol, isopropanol, allyl alcohol, rubbing alcohol NF, sodium hypochlorite, potassium hypochlorite, calcium hypochlorite, magnesium hypochlorite, sodium dichloroisocyanurate, sodium perborate NF, sodium hydroxide, potassium hydroxide, magnesium hydroxide, calcium hydroxide, ammonia, ammonium hydroxide, lithium hydroxide, barium hydroxide, silver hydroxide, sodium tetradecyl sulfate, sulfur dioxide, pentationic acid, colloidal sulfur, sulfur, sulfurated potash, sublimed tyrothricin, hexachlorophene, hypochlorous acid, acetic acid, hydrochloric acid, sulfuric acid, sodium acetate, aluminum acetate, acetarsone, aluminum subacetate, cadmium sulfide, selenium sulfide, bacitracin, coilstin, chloramphenicol, tetracycline, erythromycin, gentamycin, tobramycin, mafenide acetate, neomycin sulfate, sulfisoxazole diolamine, sulfacetamide sodium, gentamycin sulfate, amphotericin B, calomel, chiniofon, creosote, diiodohydroxyquin, eucalyptol, eucalyptus oil, glycobiarsol, gramicidin, hexyl resorcinol, methylene blue, peppermint oil, phenylethyl alcohol, phenyl salicylate, methyl salicylate, pine tar, pine oil NF, alpha-terpineol, borneol, fenchyl alcohol, o-methylchavicol, polymixin B sulfate, salicylic acid, trichloroacetic acid, benzoic acid, pyrogallol NF X, pyrogallic acid, sodium benzoate, boric acid, sodium borate, lactic acid, sodium lactate, ohiofamine, chloramine T, silver nitrate, ammoniacal silver nitrate solution, eugenol, elemental iodine, sodium iodide, potassium iodide, calcium iodide, ammonium iodide, silver iodide, colloidal silver iodide in gelatin, silver lactate, ferrous iodide, mecuric iodide red, mecuric oxide red, strontium iodide, lithium iodide, magnesium iodide, zinc iodide, silver iodide, selenium iodide, thymol iodide NF X, dithymol diiodide, povidone-iodine, iodoform, iodol, iodopyrrol, chlorinated lime, potassium bromide, sodium bromide, merbromin NF, sodium fluoride, potassium fluoride, phenyl mercuric acetate, potassium mecuric iodide, proflavine hemisulfate, 3,6-diaminoacridine bisulfate, formaldehyde, glutaraldehyde, paraformaldehyde, butyl hydroxybenzoate, mercurous chloride, iodochlorhydroxyquin, zinc nitrate, zinc sulfate, cadmium sulfate, thimerosal NF, zinc oxide, zinc acetate, zinc chloride, silver nitrate, silver sulfadiazine, hydrogen peroxide, urea hydrogen peroxide, hydrogen peroxide carbamide, benzoyl peroxide, calcium peroxide, magnesium peroxide, barium peroxide, strontium peroxide, sodium peroxide, potassium perchlorite, sodium perchlorite, calcium perchlorite, magnesium perchlorite, zinc perchlorite, zinc peroxide, zinc carbonate, zinc hydroxide, zinc sulfate, succinyl peroxide, succinchlorimide NF IX, N-Chlorosuccinimide, potassium permanganate, sodium chlorate, potassium chlorate, phenol, camphorated phenol, phenol glycerin, chloroxylenol, 4-chloro-3,5-xylenol, sodium phenolate, domiphen bromide, salicylic acid, bismuth-formic-iodide, bismuth subgallate, bacitracin zinc, sodium lauryl sulfate, carbamide peroxide, oleic acid-iodine, pipetonyl butoxide, sodium peroxyborate monohydrate, ammonium ichthosulfonate, eucalyptol, menthol, Witch Hazel, camphor, tannic acid, chloroquinaldol, nalidixic acid, zinc phenolsulfonate, zinc sulfocarbolate, hydroxynalidixic acid, pipemidic acid, norfloxacin, norfloxacin hydrochloride, 8-hydroxyquinoline sulfate, sodium phenolate, thyme oil, o-cresol, m-cresol, metacresylacetate, p-cresol, cresol NF, 4-chloro-m-cresol, 4-chloro-3,5-xylenol, saponified cresol solution NF, methylphenol, ethyl phenol, other alkyl phenols, o-phenyl phenol, other aryl phenols, bisphenols, phenyl-mecuric chloride, phenylmecuric borate, resorcinol, resorcinol monoactetate NF, orthophenylphenol, chloroxylenol, hexylresorcinol, parachlorophenol, paratertiary-amylphenol, thymol, chlorothymol NF, butylparaban, ethylparaben, methylparaben, propylparaben, triclosan, bithionol NF, o-benzyl-p-chlorophenol, hexachlorophene, poloxamer 188, a benzalkonium chloride wherein the alkyl groups attached to the nitrogen represent an alkyl from $CH_3$ to $C_{18}H_{37}$, triclobisonium chloride, undecoylium chlorideiodine, coal tar solution, furazolidone, nifuroxime, nitrofurazone NF, nitromersol NF, oxychlorosene, sodium oxychlorosene, parachlorophenol NF, camphorated parachlorophenol NF, phenylmercuric nitrate NF, gentian violet USP, hexamethylpara-rosaniline chloride, rosaniline chloride, pentamethylpararosaniline chloride, methylrosaniline chloride, tetramethylpararosaniline chloride, nonylphenoxypolyethoxyethanol, methoxypolyoxyetheneglycol 550 laurate, oxyquinoline benzoate, p-triisopropylphenoxypolyethoxy-ethanol, halazone NF, dichloramine-T, benzethonium chloride, econazole, cetylpyridinium chloride, methylbenzethonium chloride, cetyldimethylbenzylammontum chloride, dichlorobenzalkonium chloride, domiphen bromide, triclocarban, clotrimazole, ciclopirox olamine, undecylenic acid, miconazole, tolnaftate, acriflavine, euflavine, 3,6-diamino-10-methylacridium chloride, 3,6-diamino-acridine, acid acr]flavine, 5-aminoacridine hydrochloride monohydrate, malachite green G, dodecyltrimethylammonium bromide, tetradecyltrimethyl-ammonium bromide, dequalinium chloride BP, dibromopropamidine isethionite, hexadecyltrimethylammmonium bromide, chloroazodin NF X, N-chloro-p-toluenesulfonamidosodium, 4-[(dichloroamino)sulfonyl]-benzoic acid, methenamine, methenamine mandelate, methenamine hippurate, octoxynol 9, phenazopyridine hydrochloride, 9-aminoacridine hydrochloride, bismuth tribromophenate, p-tert-butylphenol, cetyldimethylethylammonium bromide, chlorothymol, cloflucaban, clorophene, cloroxine, 8-hydroxyquinoline, merbromin, mercuric oxide yellow, ammoniated mercury, p-tert-pentylphenol, phenylmercuric acetate, phenylmercuric nitrate, propylene oxide, zinc pyrithione, triclocarban, zinc bacitracin, chlortetracycline hydrochloride, calcium chlortetracycline, oxytetracycline hydrochloride, beta-propiolactone, acyclovir, acyclovir sodium, amantadine hydrochloride, cytarabine, idoxuridine, interferon, gamma interferon, ribaviron, rifampin, suramin, trifluridine, vidarabine, zidovudine, methisazone, tumor necrosis factor, ampligen, ansamycin, (E)-5-(2-bromovinyl-2'-deoxyuridine, butylated hydroxytoluene, castamospermine, dextran sulfate, dideoxycytidine, dideoxyadenosine, dideoxylnosine, Peptide-T, dihydromethylpyridinylcarbonyloxyazidodideoxythymidine, ganciclovir, 2'-fluoro-2'-deoxy-5-iodo-ara C, phosphonoformate, rimantadine hydrochloride and mixtures thereof.

6. A glove according to claim 1, wherein the non-liquid antiseptic composition contains a liquid component selected from the group consisting of water, methanol, ethanol, isopropanol, propanol, allyl alcohol, butanol, isobutanol, sec-butanol, tert-butanol, benzyl alcohol, 2-methoxyethanol, 2-ethoxyethanol, 2-octyl dodecanol, nonoxynol-9, n-octyl alchol, glycerol, propylene glycol, a polyethylene glycol of about 150 to about 700 molecular weight, urea, acetone, methyl ethyl ketone, ethyl ketone, methyl isopropyl ketone, 2-pentanone, ethyl acetate, 2-methoxyethyl acetate, ethyl propionate, ethyl butyrate, ethyl valerate, methyl acetate, propyl acetate, isopropyl acetate, 2-ethoxyethyl acetate, buryl acetate, sec-butyl acetate, tert-butyl acetate, amyl acetate, pentyl acetate, isopentyl acetate, benzyl acetate, mineral oil, silicone oil, hexamethyl disiloxane, glycerol trioctanoate, decyl oleate, cetearyl isononanoate, dimethicone, perfluropolymethyisopropyl ether of about 1500 to about 8800 molecular weight, olive oil, cottonseed oil, corn oil, soybean oil, wheat germ oil, linseed oil, pine oil, almond oil, macadamia oil, coconut oil, jojoba oil, peanut oil, persia oil, castor oil, cod liver oil, shark liver oil, mink oil, squalene and mixtures thereof.

7. A glove according to claim 1, wherein the non-liquid antiseptic composition contains a surface-active agent to facilitate the coating of the object with the non-liquid antiseptic composition, the surface active agent selected from the group consisting of dodecyldimethylamine oxide, lauryldimethylamine oxide, stearic acid, dibutyl adipate, octyl stearate, sodium cetearyl stearate, isopropyl myristrate, palmitic acid, stearyl alcohol, cetyl alcohol, colloidal magnesium aluminum silicate, caprylic triglyceride, captic triglyceride, cetostearyl alcohol, decyl-beta-D-glucopyranoside, nonyl-beta-D-glucopyranoside, octyl-beta-D-glucopyranoside, triethanolamine stearate, heptyl-beta-D-glucopyranoside, hexyl-beta-D-glucopyranoside, dodecyl-beta-D-maltoside, decyl-beta-D-maltoside, sodium dodecylsulfate, sodium oleate, potassium laurate, sodium laurate, sodium lauryl sulfate, glycerol monostearate, propylene glycol monostearate, bis(2-ethylhexyl)-sodium sulfosuccinate, N-octylsulfobetaine, propylene glycol monolaurate, N-dodecylsulfatobetaine, octyl-beta-D-thioglucopyranoside, heptyl-beta-D-thioglucopyranoside, N-dodecyl-N,N-dimethylglycine, cetyl alcohol, N-decylsulfatobetaine, digitonin, N-hexyldecylsulfatobetaine, N-tetradecylsulfatobetaine, dioctyl sodium sulfosuccinate, N,N,bis(3-D-gluconamidopropyl)-cholamide, sodium deoxycholate, N,N,bis(3-D-gluconamidopropyl)-deoxycholamide, glycerol monostearate, sodium taurodeoxycholate, sodium cholate, sodium taurocholate, sodium glycocholate, cetyltrimethylammonium bromide, 3-[(3-cholamidopropyl)dimethylammonio]-1-propanesulfonate, 3-[(3-cholamidopropyl)dimethylammonio]-2-hydroxypropane-1-sulfonate, octanoyl-N-methylglucamide, nonanoyl-N-methylglucamide, decanoyl-N-methylglucamide, nonyl-N-methylglucamide, lecithin, lysolecithin, nonaethylene glycol monododecyl ether, nonaethylene glycol octylphenol ether, nonaethylene glycol octylcyclohexyl ether, heptaethylene glycol octylphenyl ether, heptaethylene glycol octylcyclohexyl ether, polyoxyethylene (10) monolauryl ether, polyoxyethylene (8) isotridecyl ether, polyoxyethylene (10) isotridecyl ether, polyoxyethylene (15) isotridecyl ether, polyoxyethylene (9) lauryl ether, polyoxyethylene (23) lauryl ether, octaethylene glycol monododecyl ether, nonaethylene glycol monododecyl ether, polyethylene polypropylene glycol, sorbitan monopalmitate, sorbitan monooleate, sorbitan monostearate, polyoxyethylene sorbitan monolaurate, polyoxyethylene sorbitan monooleate, polyoxyethylene-4-lauryl ether, a polyethylene glycol of about 150 to about 600 molecular weight, polyoxyethylene glycol 400 molecular weight, polyoxyethylene glycol 1540 molecular weight, polyoxyethylene glycol 4000 molecular weight, polyoxyethylene glycol 8000 molecular weight, polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-sorbitan monolaurate, polyoxyethylene-40-stearate, dimethicone, simethicone, dimethylpolysiloxane, sorbitan trioleate, sorbitan tristreate, propylene glycol monostearate, sorbitan sesquioleate, diphenylmethylsilicone, lauryldimethylbenzylammonium chloride, a perfluoropolymethylisopropyl ether of about 1500 to about 6600 molecular weight, acacia, type A gelatin, type B Gelatin, egg yolk phospholipids, soybean phospholipids, cholesterol, colloidal aluminum silicate, colloidal magnesium hydroxide, and mixtures thereof.

8. A glove according to claim 1, wherein the non-liquid antiseptic composition contains an algesic agent to increase the pain sensation perceived from the hand, to alert the individual when the hand has been wounded, the algesic agent selected from the group consisting of formic acid, acetic acid, hydrochloric acid, phosphoric acid, sodium hydrogen phosphate, sodium phosphate, potassium hydrogen phosphate, potassium phosphate, citric acid, sodium hydrogen citrate, sodium citrate, sulfuric acid, sodium hydrogen sulfate, sodium sulfate, sodium hypochlorite, potassium hypochlorite, bradykinin, substance P, bee venom, wasp venom, ant venom, potassium chloride, potassium citrate, potassium sulfate, potassium phosphate, potassium carbonate, potassium bromide, potassium iodide, potassium fluoride, potassium hydroxide, potassium nitrate, and mixtures thereof.

9. A glove according to claim 1, wherein the non-liquid antiseptic composition further contains a colorant as a means for providing a colored visual signal to the individual when and where the glove wall has been punctured by the object, the colorant selected from the group consisting of a dye, an iron oxide, titanium dioxide, and mixtures thereof.

10. A glove according to claim 1, wherein the non-liquid antiseptic composition further contains a vasoconstricting agent in a concentration of about 1 vasoconstricting agent part in 200,000 parts of the non-liquid antiseptic composition to about 1 vasoconstricting agent part in 2,000 parts of the liquid antiseptic composition as a means for reducing blood flow in the hand wound as a means for reducing a systemic spreading of the infectious pathogen in the individual, the vasoconstricting agent selected from the group consisting of epinephrine, norepinephrine, phenylephrine, ephedrine, metaraminol, methoxamine, and mixtures thereof.

11. A glove according to claim 1, wherein the non-liquid antiseptic composition further contains a viscosity-modifying polymer as a means for increasing the viscosity of the non-liquid antiseptic composition, the viscosity-modifying polymer selected from the group consisting of gum arabic, xantham gum, gum acacia, gum tragacanth, agar, glycyrrhiza, sodium alginate, bentonire, cellulose, methyl cellulose, carboxymethyl cellulose sodium, glycerol, propylene glycol, pyroxylin, polyoxyethylene glycols of about 150 to about 6000 molecular weight, gelatin, dimethicone of about 100 to about 3000 centistokes viscosity, simethicone, dimethylpolysiloxane, perfluropolymethyl-isopropyl ether of about 1500 to about 6600 molecular weight, starch, and mixtures thereof.

12. A glove according to claim 1, wherein a structural connection is made by using a third material to connect the first material to the second material, the third material comprising: a structural material selected from the group consisting of latex rubber, cis-1,4-polyisoprene rubber, cis-polybutadiene rubber, neoprene rubber, nitrile rubber, silicone rubber, case-hardened latex rubber, isobutylene-isoprene 1. butyl rubber, butadieneacrylonitrile 1. nitrile rubber, styrene-butadiene rubber, ethylene-propylene copolymer, ethylene-propylene diene terpolymer, polyisobutylene, chlorosulphonated polyeten, ester-type urethan rubber, polychlormethyloxyran epichlorhydrin rubber, epichlorhydrin copolymer with ethyleneoxydichlormethyloxyran copolymer, cellulose acetate plastic, vinyl plastic, polyethylene plastic, polypropylene plastic, polyvinyl chloride plastic, polyvinyl acetate plastic, polystyrene plastic, polymethyl methylacrylate plastic, polyacrylonitrile plastic, vinyllite plastic, saran plastic, polytetrafluoroethylene plastic, polytrifluorochloro-ethylene plastic, nylon plastic, rayon plastic, polycaprolactam plastic, polyester plastic, urea formaldehyde plastic, polyurethane plastic, isostactic polypropylene plastic, polyamide plastic, phenolic plastic, silicone plastic, silk fiber, cotton fiber, plant fiber, wool fiber, animal skin, animal intestinal tissue, animal connective tissue, metallic fiber, mineral fiber, a glue comprising at least one of the aforementioned structural materials, and mixtures thereof.

13. A glove according to claim 12, wherein the structural connection reconfigures the compartment storing the non-liquid antiseptic composition into a plurality of compartments capable of storing the non-liquid antiseptic composition.

14. A glove according to claim 1, capable of providing a non-liquid antiseptic composition, which comprises: a quantity of povidone-iodine in a non-liquid composition.

15. A glove according to claim 1, capable of providing a non-liquid antiseptic composition, which comprises: a quantity of elemental iodine in a non-liquid composition.

16. A glove according to claim 1, capable of providing a non-liquid antiseptic composition, which comprises: a quantity of a hypochlorite salt antiseptic in a non-liquid composition.

17. A glove according to claim 1, capable of providing a non-liquid antiseptic composition, which comprises: a quantity of chlorhexidine gluconate.

18. A glove according to claim 1, capable of providing a non-liquid antiseptic composition, which comprises: a quantity of nonoxynol-9.

19. A method of using a flexible protective glove with a liquid-impermeable wall containing a non-liquid antiseptic composition or storing a number of substances that can form a non-liquid antiseptic composition when the substances are combined, the wall comprising an inner layer and an outer layer wherein the inner layer has a lower elasticity than the outer layer on a hand of an individual to protect the hand in the event that an object contaminated with an infectious agent punctures the glove, may wound the hand and may contaminate the hand and the hand wound with the infectious pathogen, comprising the steps of:
(a) using the glove initially as a liquid-impermeable physical barrier to infectious pathogens; using the glove to permit the hand to perform a delicate, dexterous and complex type of work that includes the type of work performed by a surgeon, medical doctor, a dentist, a laboratory worker, a hospital health care worker, a law enforcement worker, and a hospital worker;
(b) using the object to puncture the wall so that the wall has a hole;
(c) bringing the object into contact with the non-liquid antiseptic composition or using the object to cause some combination of the substances in the wall so that some non-liquid antiseptic composition is formed when the substances are combined in some portion of the wall that has been punctured by the object;
(d) coating a portion of the object puncturing the glove wall with the non-liquid antiseptic composition when the object punctures the glove wall;
(e) using the object puncturing the glove as a means for transfering a portion of the coating of the non-liquid antiseptic composition on the object, to the hand and into the hand wound when the object contacts the hand or the hand wound;
(f) promoting a larger transfer of the non-liquid antiseptic composition from the glove wall to the hand and hand wound, than from the glove to the outer surface of the glove wall, when the non-liquid antiseptic composition is dispersed from the hole in the punctured glove wall, by providing a smaller hole in the outer layer than in the inner layer of the glove wall after the object has been removed from the glove wall, by selecting a material composition for the inner glove layer that has a lower elasticity than the material composition selected for the outer glove layer; and
(g) using the non-liquid antiseptic composition transferred from and dispersed from the glove to the hand or to the hand wound to kill, to inactivate, and to otherwise destroy the infectious pathogen that may have been transferred to the skin and into the hand wound by the object.

20. A flexible protective glove with a liquid-impermeable wall having the capability to provide a non-liquid antiseptic composition treatment to a hand and to a hand wound should the wound occur underneath the glove while the glove is being worn when a wall of the glove is punctured by an object that may be contaminated with an infectious pathogen, comprising:
(a) a glove wall with a liquid-impermeable outer layer comprised of a first material having a thickness of about 1 mil to about 40 mils and a liquid-impermable inner layer composed of a second material having a thickness of about 0.3 mils to about 30 mils wherein the first material and the second material form the walls of a compartment capable of providing a non-liquid antiseptic composition;

(b) wherein the non-liquid antiseptic composition in the compartment comprises an antiseptic and a vasoconstrictive agent, or a number of substances including a vasoconstrictive agent that can form the non-liquid antiseptic composition when the object punctures the glove wall and causes a combination of a portion of the substances, wherein at least a portion of the glove wall contains a non-liquid antiseptic composition when the glove wall is punctured by an object;

(c) the glove wall capable of providing a physical barrier as a means of protection to the hand while the glove is being worn by an individual until a portion of the glove wall is punctured by an object; the glove wall capable of being punctured by the object while the glove is being worn on the hand;

(d) the glove wall having the flexibility to allow the hand of an individual in need of wearing the glove to easily and adequately perform delicate, dexterous and complex work including the work performed by a surgeon, a medical doctor, a dentist, a laboratory worker, a health care worker, a law enforcement worker, and a hospital worker;

(e) the glove having the capability to provide a coating to at least a portion of the object puncturing the glove wall; the coating comprising the non-liquid antiseptic composition; the coating on the object providing a means for immediately transfering some of the non-liquid antiseptic composition onto the hand and into the hand wound contacted by the object; the non-liquid antiseptic composition transferred to the hand and to the hand wound having the capability to provide an immediate non-liquid antiseptic composition treatment to the hand and hand wound;

(f) the glove having the additional capability to disperse some of the non-liquid antiseptic composition from a section of the glove wall having a hole resulting from the object puncturing the glove wall; and (g) the glove having the capability to help treat the hand and the hand wound with the non-liquid antiseptic composition when the object punctures the glove wall, when the object may contact the hand, when the object may wound the hand, and when the object may contaminate the hand and the hand would with the infectious pathogen; wherein the non-liquid antiseptic composition transferred or dispersed to the hand and the hand wound has the capability to help to protect the hand, the hand wound, and the systemic circulation of the individual by killing, inactivating, and otherwise destroying the infectious pathogen that may contaminate the hand and the hand wound.

* * * * *